United States Patent
Lee et al.

(10) Patent No.: US 10,544,166 B2
(45) Date of Patent: Jan. 28, 2020

(54) COMPOUND AND COLOR CONVERSION FILM COMPRISING SAME

(71) Applicant: LG CHEM, LTD., Seoul (KR)

(72) Inventors: Hoyong Lee, Daejeon (KR); Duy Hieu Le, Daejeon (KR); Jiyeon Sung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/738,565

(22) PCT Filed: Oct. 10, 2016

(86) PCT No.: PCT/KR2016/011304
§ 371 (c)(1),
(2) Date: Dec. 20, 2017

(87) PCT Pub. No.: WO2017/073923
PCT Pub. Date: May 4, 2017

(65) Prior Publication Data
US 2018/0186817 A1    Jul. 5, 2018

(30) Foreign Application Priority Data

Oct. 27, 2015 (KR) .................. 10-2015-0149665
May 31, 2016 (KR) .................. 10-2016-0067503

(51) Int. Cl.
| | | |
|---|---|---|
| *C07F 5/02* | (2006.01) | |
| *G02B 5/22* | (2006.01) | |
| *C09K 11/06* | (2006.01) | |
| *F21K 9/64* | (2016.01) | |
| *G02F 1/13357* | (2006.01) | |
| *F21V 8/00* | (2006.01) | |

(52) U.S. Cl.
CPC ............. *C07F 5/022* (2013.01); *C09K 11/06* (2013.01); *F21K 9/64* (2016.08); *G02B 5/22* (2013.01); *C09K 2211/1033* (2013.01); *C09K 2211/1062* (2013.01); *C09K 2211/1088* (2013.01); *C09K 2211/1096* (2013.01); *G02B 6/0031* (2013.01); *G02B 6/0046* (2013.01); *G02B 6/0055* (2013.01); *G02B 6/0065* (2013.01); *G02F 1/133602* (2013.01)

(58) Field of Classification Search
None
See application file for complete search history.

(56) References Cited

U.S. PATENT DOCUMENTS

2004/0157231 A1*  8/2004  Meltola ............... G01N 33/533
                                                          435/6.13

FOREIGN PATENT DOCUMENTS

KR    10-1484748    1/2015

OTHER PUBLICATIONS

Esnal, I. et al., "Coumarin-BODIPY Hybrids by Heteroatom Linkage; Versatile, Turnable and Photostable Dye Lasers for UV Irradiation," Physical Chemistry Chemical Physics, 2015, vol. 17, pp. 8239-8247.
Cao, X. eet al., "Ratiometric Sensing of Fluoride Anions Based on a BODIPY-Coumarin Platform," Organic Letters, 2011, vol. 13, No. 22, pp. 6098-6101.
Bochkov, A. Y. et al., "NIR-fluorescent Coumarin-fused BODIPY Dyes with Large Stokes Shifts," Chemical Communications, 2013, vol. 49, pp. 11653-11655.
Qian, Y. et al., "A BODIPY-coumarin-based Selective Fluorescent Probe for Rapidly Detecting Hydrogen Sulfide in Blood Plasma and Living Cells," Sensors and Actuators B: Chemical, 2013, vol. 182, pp. 498-503.
Yun Zhao et al., "Through-bond energy transfer cassettes based on coumarin-Bodipy/distyryl Bodiby dyads with efficient energy efficiences and large pseudo-Stokes' shifts," J. Mater. Chem. 21:13168-13171 (2011).

* cited by examiner

*Primary Examiner* — Ana Z Muresan
(74) *Attorney, Agent, or Firm* — Dentons US LLP

(57) ABSTRACT

The present specification relates to a novel compound, and a color conversion film, a backlight unit and a display apparatus including the same.

19 Claims, 9 Drawing Sheets

【FIG. 1】
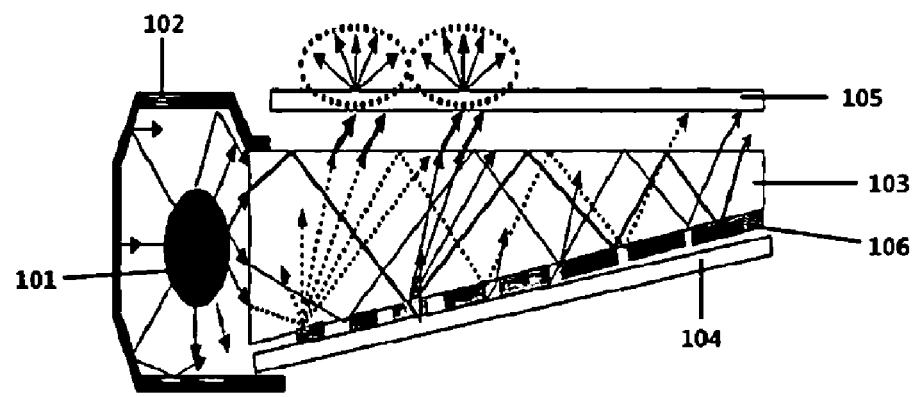
【FIG. 2】
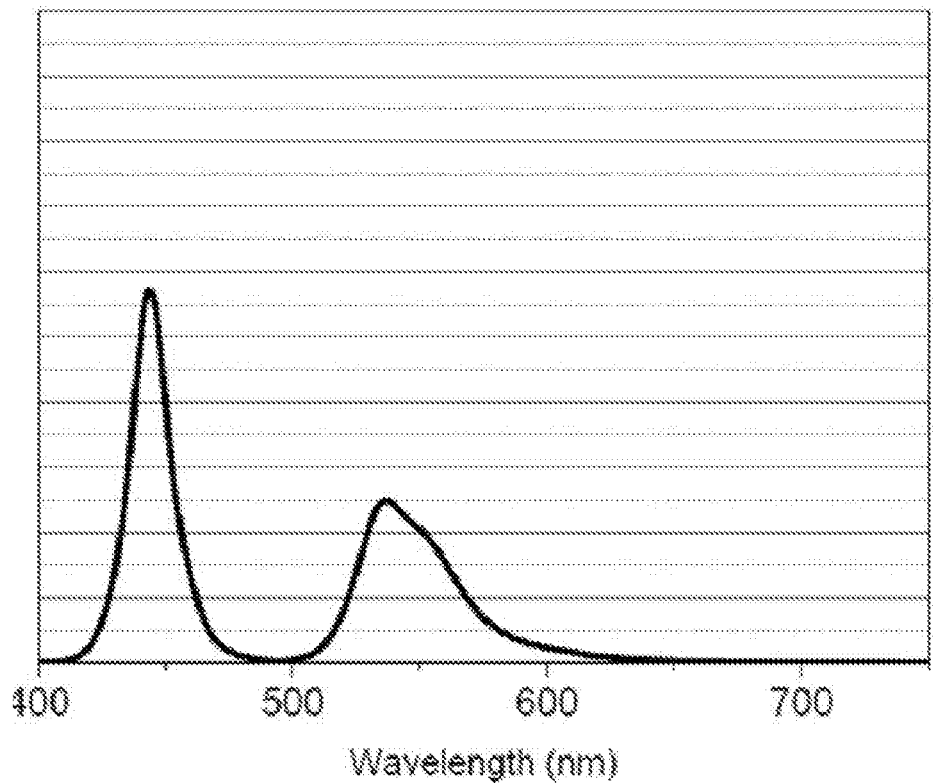

[FIG. 3]
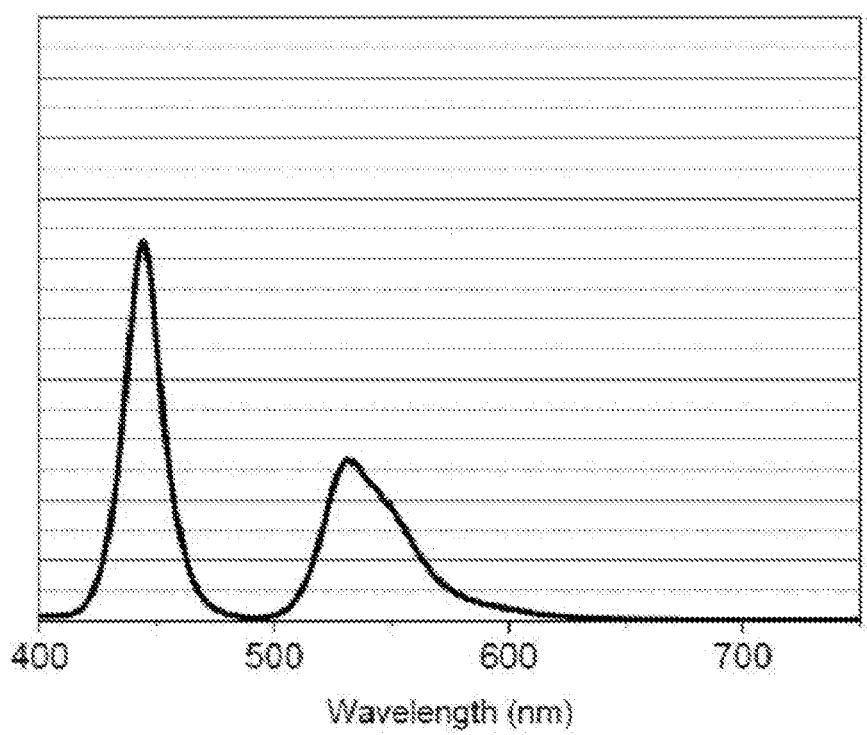

【FIG. 4】
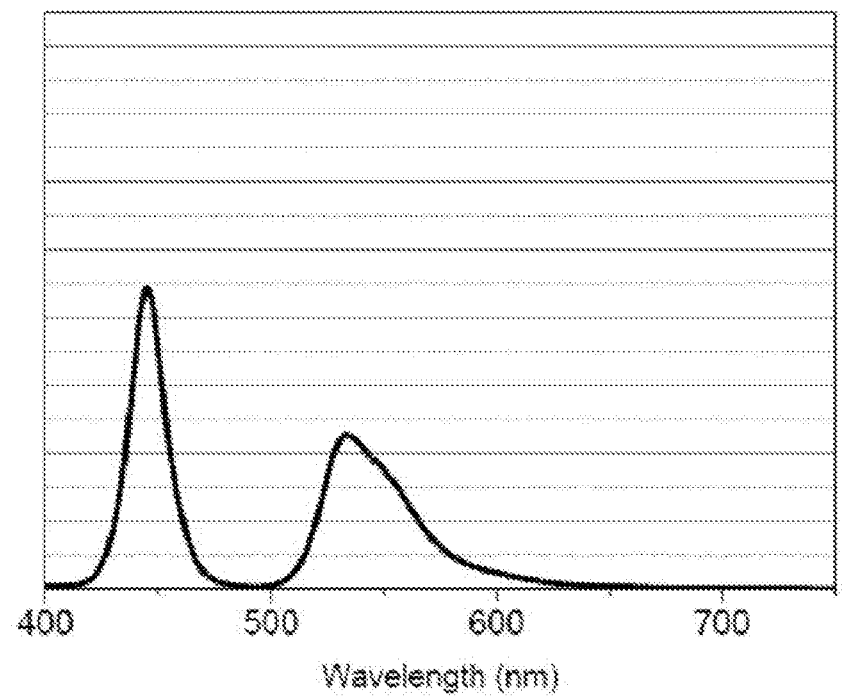

[FIG. 5]
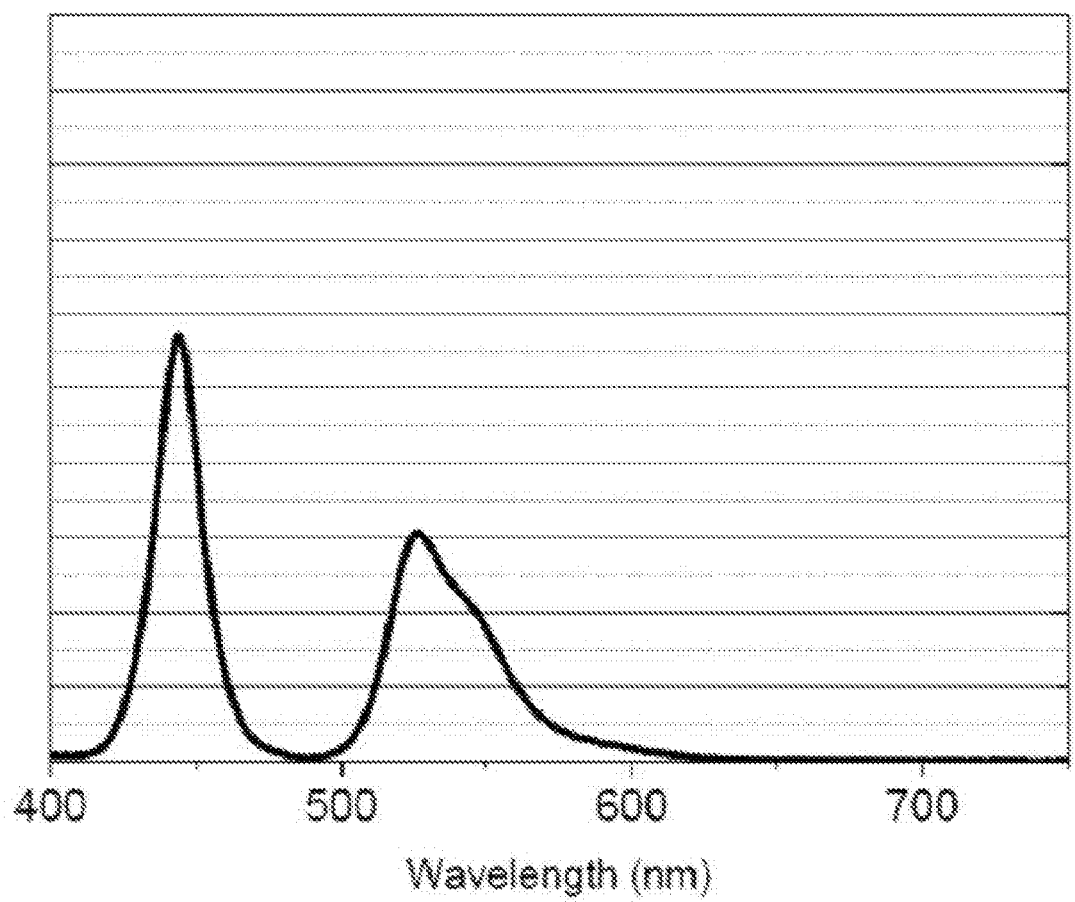

【FIG. 6】
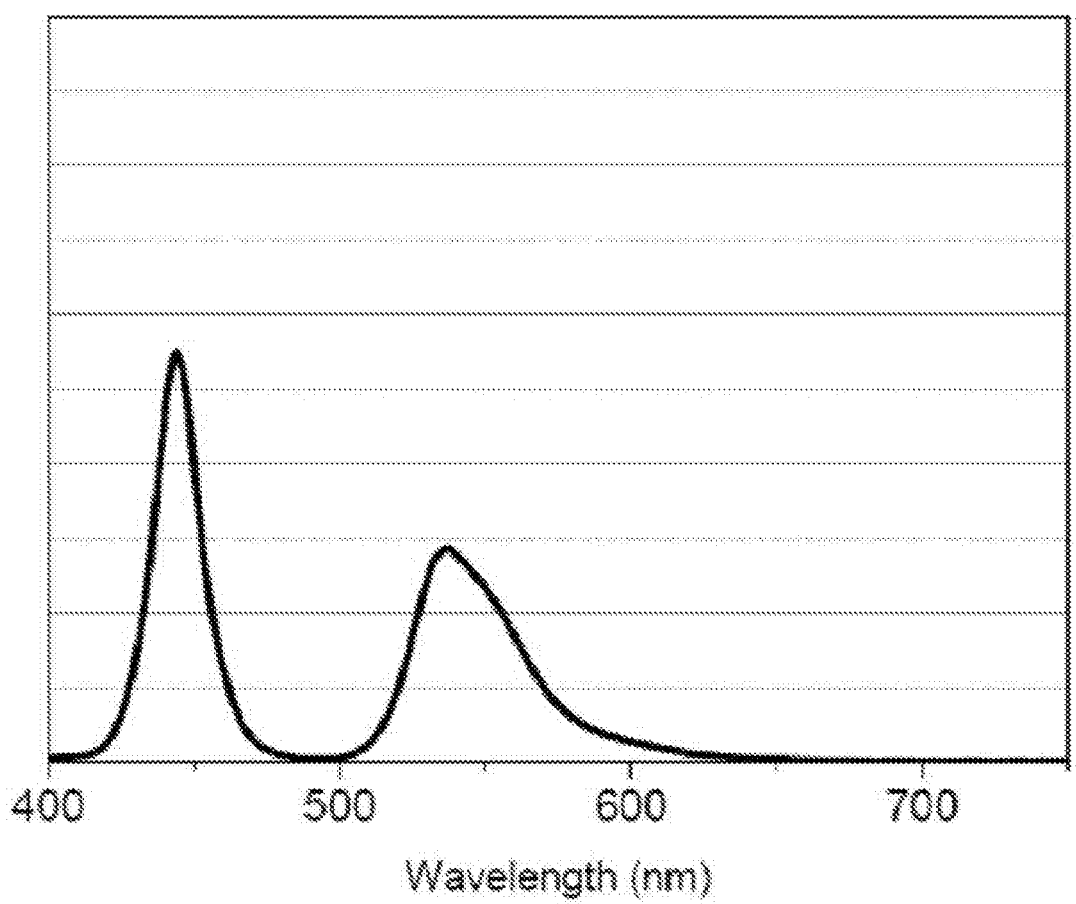

[FIG. 7]
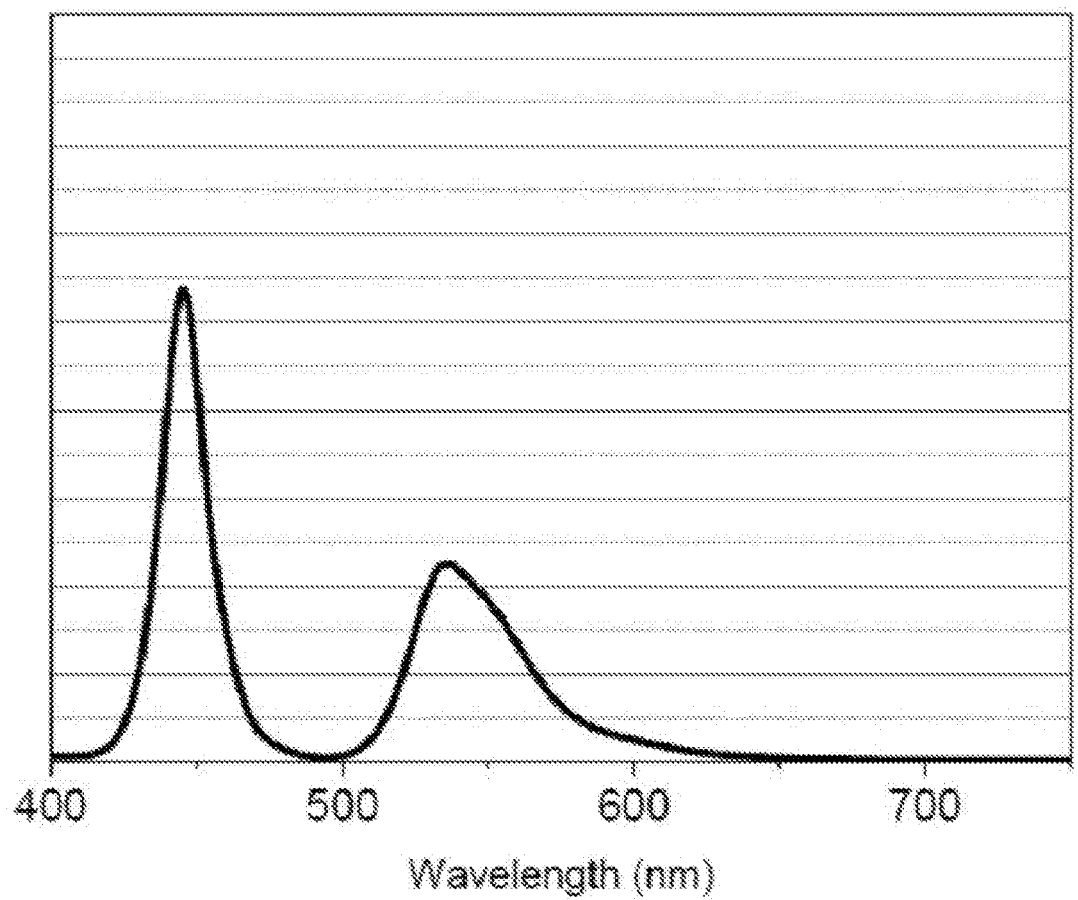

[FIG. 8]
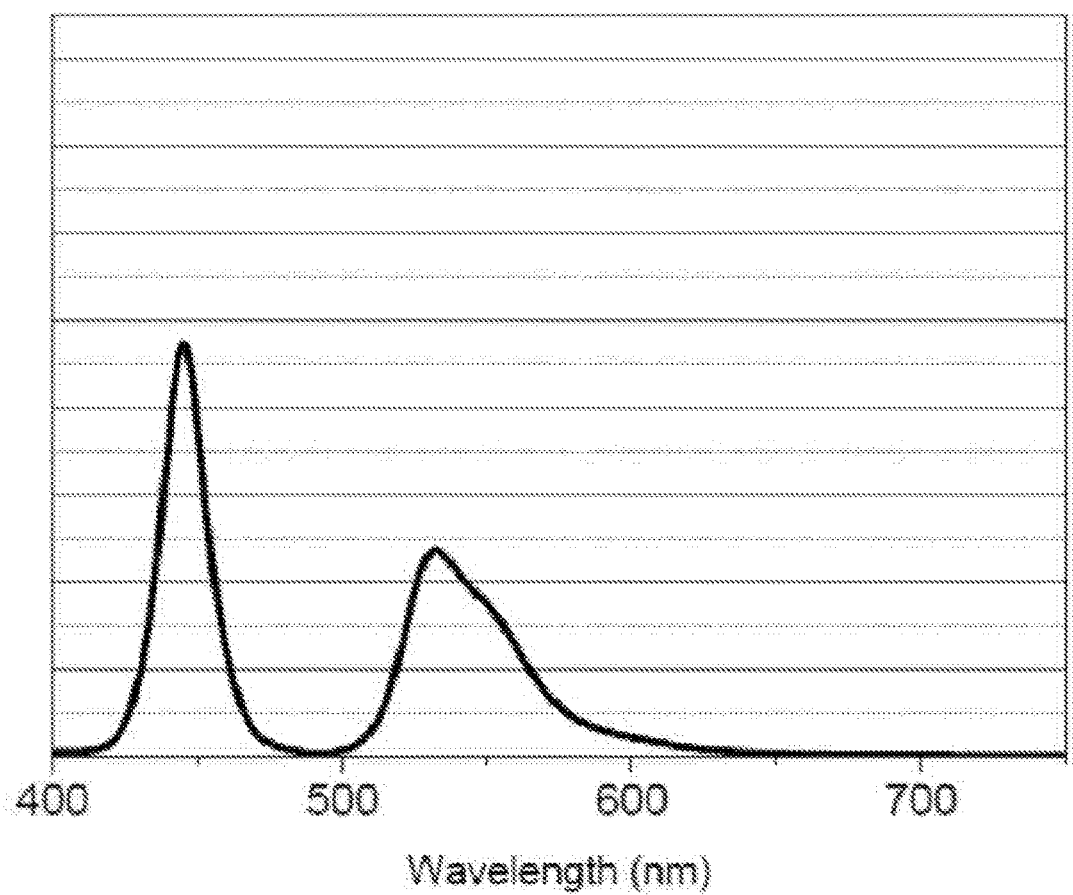

[FIG. 9]
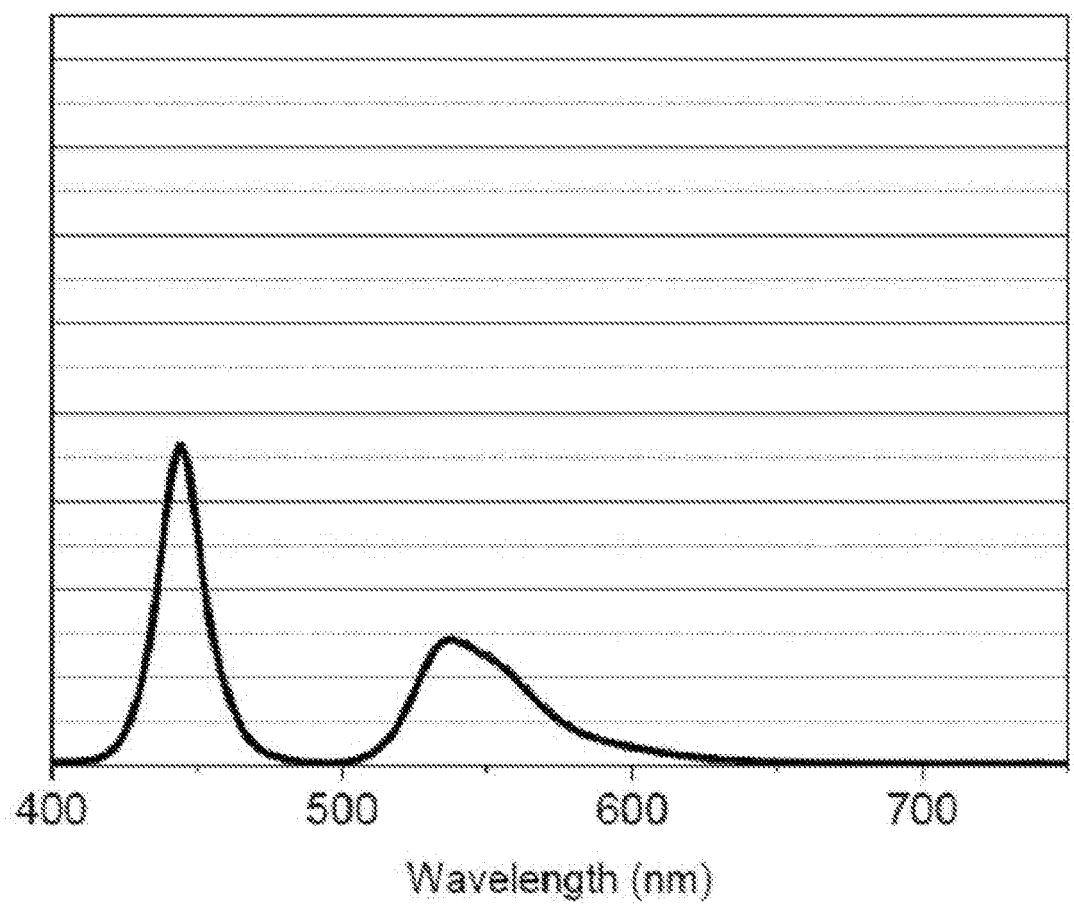

[FIG. 10]
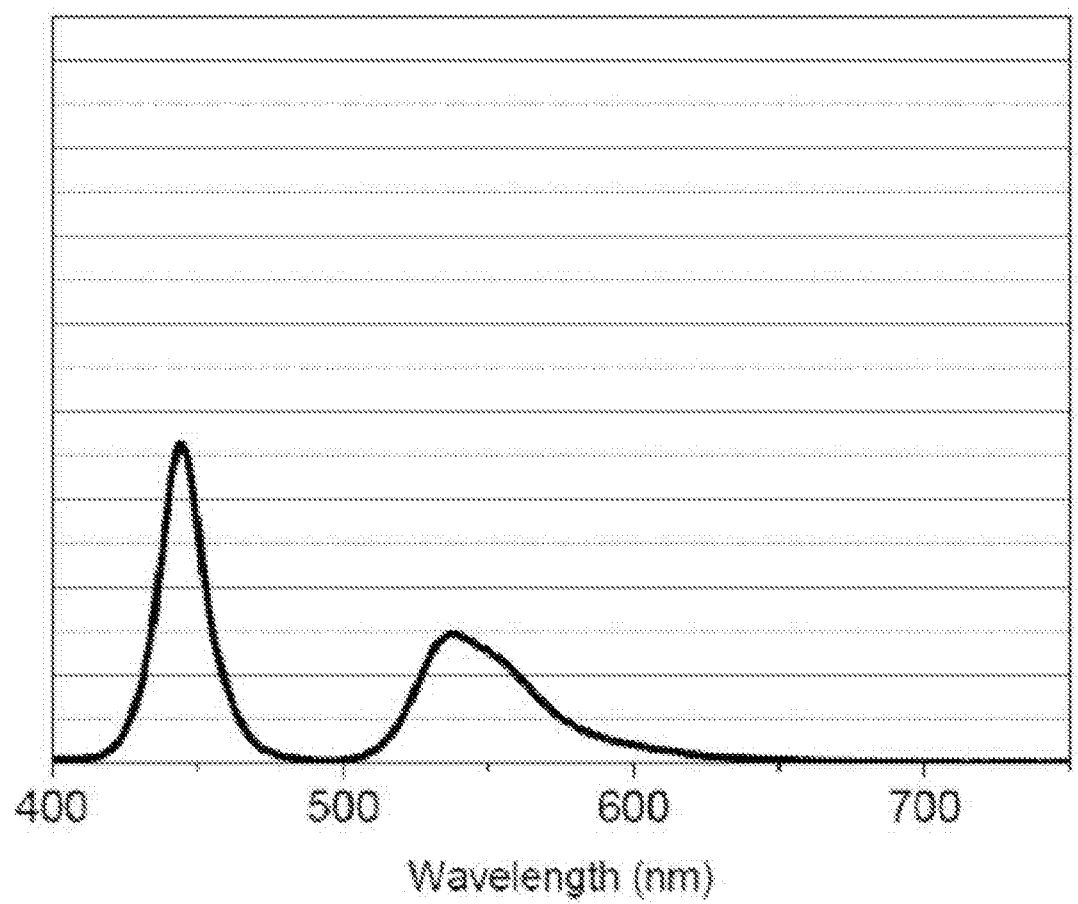

COMPOUND AND COLOR CONVERSION FILM COMPRISING SAME

TECHNICAL FIELD

This application is a National Stage Application of International Application No. PCT/KR2016/011304 filed on Oct. 10, 2016, which claims priority to and the benefit of Korean Patent Application No. 10-2015-0149665, filed with the Korean Intellectual Property Office on Oct. 27, 2015, and Korean Patent Application No. 10-2016-0067503, filed with the Korean Intellectual Property Office on May 31, 2016, all of which are incorporated herein in their entirety by reference for all purposes as if fully set forth herein.

The present specification relates to a novel compound, and a color conversion film, a backlight unit and a display apparatus including the same.

BACKGROUND ART

Existing light emitting diodes (LED) are obtained by mixing a green phosphorescent substance and a red phosphorescent substance to a blue light emitting diode, or mixing a yellow phosphorescent substance and a blue-green phosphorescent substance to a UV light emitting diode. However, with such a method, it is difficult to control colors, and therefore, color rendering is not favorable. Accordingly, color gamut declines.

In order to overcome such color gamut decline and reduce production costs, methods of obtaining green and red in a manner of filming quantum dots and binding the dots to a blue LED have been recently tried. However, cadmium series quantum dots have safety problems, and other quantum dots have significantly decreased efficiency compared to cadmium series quantum dots. In addition, quantum dots have reduced stability for oxygen and water, and have a disadvantage in that the performance is significantly degraded when aggregated. Furthermore, unit costs of production are high since, when producing quantum dots, maintaining the sizes is difficult.

PRIOR ART DOCUMENTS

Patent Documents

Korean Patent Application Laid-Open Publication No. 2000-0011622

DISCLOSURE

Technical Problem

The present specification provides a novel compound, and a color conversion film, a backlight unit and a display apparatus including the same.

Technical Solution

One embodiment of the present specification provides a compound represented by the following Chemical Formula 1.

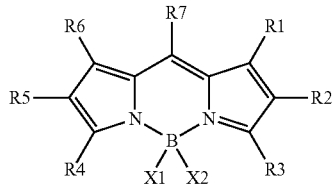

[Chemical Formula 1]

In Chemical Formula 1,

X1 and X2 are the same as or different from each other, and each independently a halogen group; a nitrile group; a substituted or unsubstituted alkyl group; a substituted or unsubstituted alkoxy group; —O(C=O)R; a substituted or unsubstituted alkenyl group; a substituted or unsubstituted alkynyl group; a substituted or unsubstituted aryl group; or a substituted or unsubstituted heteroaryl group, R is a substituted or unsubstituted alkyl group, at least one of R1 to R6 is represented by the following Chemical Formula 2, and the rest are the same as or different from each other and each independently a group represented by the following Chemical Formula 3; hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, R7 is represented by -(L)$_r$-A, L is a direct bond; —O—; —N(H)—; —OC(=O)—; a substituted or unsubstituted alkylene group; a substituted or unsubstituted arylene group; or a substituted or unsubstituted heteroarylene group, A is a group represented by the following Chemical Formula 3; hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, r is an integer of 1 to 10, when r is 2 or greater, 2 or more Ls are the same as or different from each other,

[Chemical Formula 2]

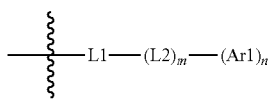

in Chemical Formula 2,

L1 is represented by any one of the following Chemical Formulae 4 to 6,

L2 is a direct bond; —O—; —N(H)—; —OC(=O)—; a substituted or unsubstituted alkylene group; a substituted or unsubstituted arylene group; or a substituted or unsubstituted heteroarylene group, Ar1 is represented by the following Chemical Formula 3, m is an integer of 1 to 5, n is an integer of 1 to 3, when m and n are each 2 or greater, the 2 or more structures in the parentheses are the same as or different from each other,

is a site bonding to at least one of R1 to R6 of Chemical Formula 1,

[Chemical Formula 3]

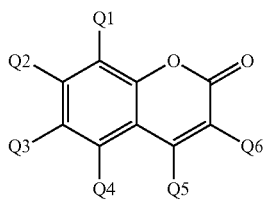

in Chemical Formula 3, at least one of Q1 to Q6 is a site bonding to L2 of Chemical Formula 2, or a site bonding to any one of R1 to R7 of Chemical Formula 1, and the rest are the same as or different from each other and each independently hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring,

[Chemical Formula 4]

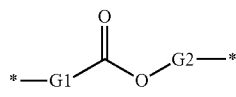

[Chemical Formula 5]

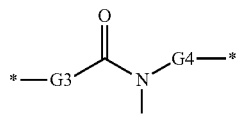

[Chemical Formula 6]

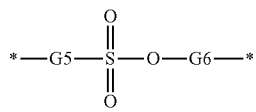

in Chemical Formulae 4 to 6,

* is a site bonding to at least one of R1 to R6 of Chemical Formula 1, or a site bonding to L2 of Chemical Formula 2, G1 to G6 are the same as or different from each other, and each independently a direct bond; —O—; —N(H)—; —OC(=O)—; a substituted or unsubstituted alkylene group; a substituted or unsubstituted arylene group; or a substituted or unsubstituted heteroarylene group, and M1 is hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

Another embodiment of the present specification provides a color conversion film including a resin matrix; and the compound represented by Chemical Formula 1 dispersed into the resin matrix.

Still another embodiment of the present specification provides a backlight unit including the color conversion film.

Yet another embodiment of the present specification provides a display apparatus including the backlight unit.

Advantageous Effects

Metal complexes according to one embodiment of the present specification, that is, compounds represented by Chemical Formula 1, are stable for water or oxygen as well as having high fluorescence efficiency, and have low unit costs of production compared to quantum dots. Accordingly, by using compounds represented by Chemical Formula 1 described in the present specification as a fluorescent material of a color conversion film, a color conversion film having excellent luminance and color gamut, and with simple manufacturing process and low manufacturing costs can be provided.

DESCRIPTION OF DRAWINGS

FIG. 1 is a mimetic diagram using a color conversion film according to one embodiment of the present specification in a backlight.

FIG. 2 is a diagram showing a luminance spectrum of Compound 1-1.

FIG. 3 is a diagram showing a luminance spectrum of Compound 1-23.

FIG. 4 is a diagram showing a luminance spectrum of Compound 1-25.

FIG. 5 is a diagram showing a luminance spectrum of Compound 1-71.

FIG. 6 is a diagram showing a luminance spectrum of Compound 1-79.

FIG. 7 is a diagram showing a luminance spectrum of Compound 1-80.

FIG. 8 is a diagram showing a luminance spectrum of Compound 1-82.

FIG. 9 is a diagram showing a luminance spectrum of Compound 1-83.

FIG. 10 is a diagram showing a luminance spectrum of Compound 1-84.

MODE FOR DISCLOSURE

Hereinafter, the present specification will be described in more detail.

A color conversion film according to one embodiment of the present specification provides a compound represented by Chemical Formula 1.

In the present specification, a certain part "including" certain constituents means capable of further including other constituents, and does not exclude other constituents unless particularly stated on the contrary.

In the present specification, one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; an ether group; a hydroxyl group; a substituted or unsubstituted coumarine group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures as below may be included, but the imide group is not limited thereto.

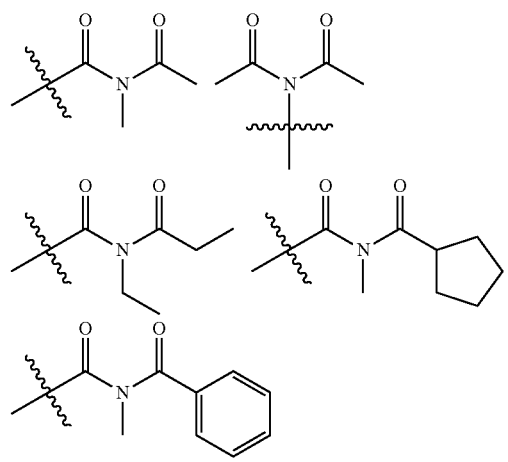

In the present specification, in the amide group, the nitrogen of the amide group may be substituted with hydrogen, a linear, branched or cyclic alkyl group having 1 to 30 carbon atoms or an aryl group having 6 to 30 carbon atoms. Specifically, compounds having the following structural formulae may be included, but the amide group is not limited thereto.

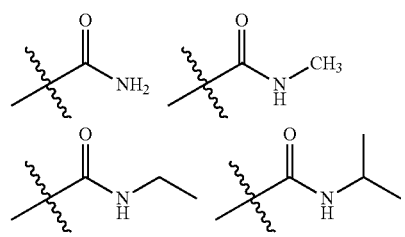

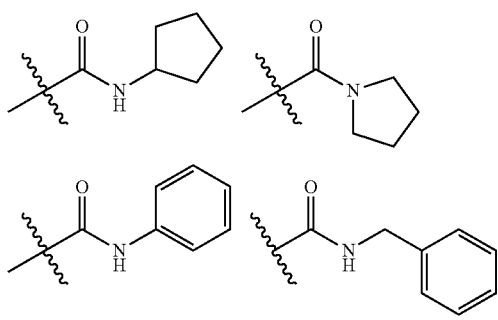

In the present specification, the number of carbon atoms of the carbonyl group is not particularly limited, but is preferably from 1 to 30. Specifically, compounds having structures as below may be included, but the carbonyl group is not limited thereto.

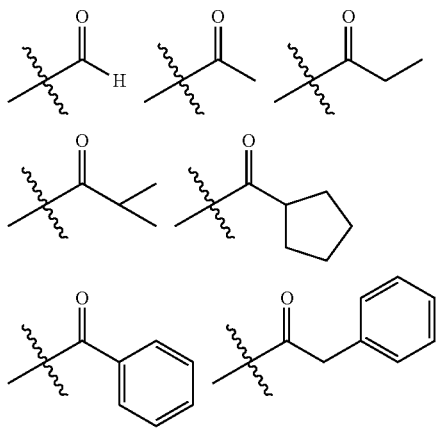

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, but the ester group is not limited thereto.

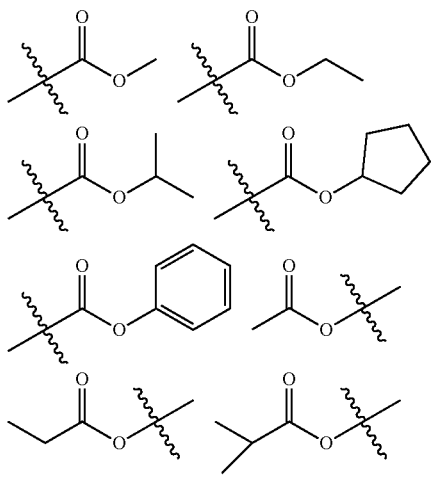

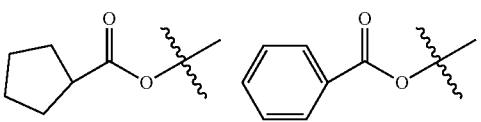

In the present specification, in the ether group, the oxygen of the ether group may be substituted with a linear, branched or cyclic alkyl group having 1 to 25 carbon atoms or an aryl group having 6 to 30 carbon atoms. Specifically, compounds having the following structural formulae may be included, but the ether group is not limited thereto.

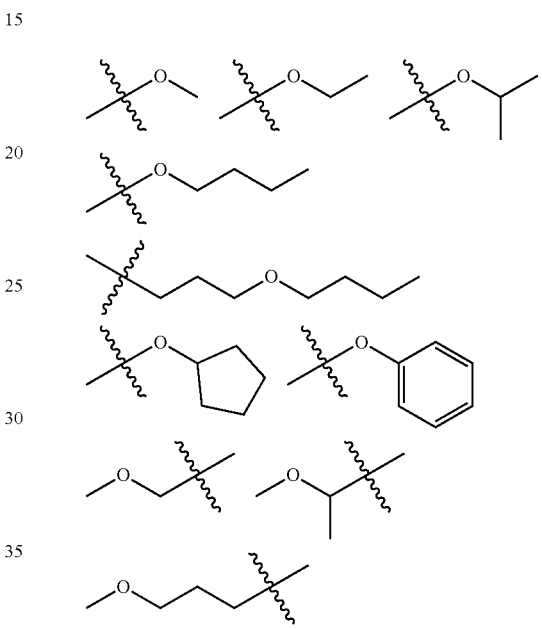

In the present specification, in the coumarine group, the carbon of the coumarine group may be substituted with a halogen group, a nitrile group, a linear, branched or cyclic alkyl group having 1 to 25 carbon atoms; an amine group; a linear or branched alkoxy group having 1 to 25 carbon atoms; or an aryl group having 6 to 30 carbon atoms. Specifically, compounds having the following structural formulae may be included, but the coumarine group is not limited thereto.

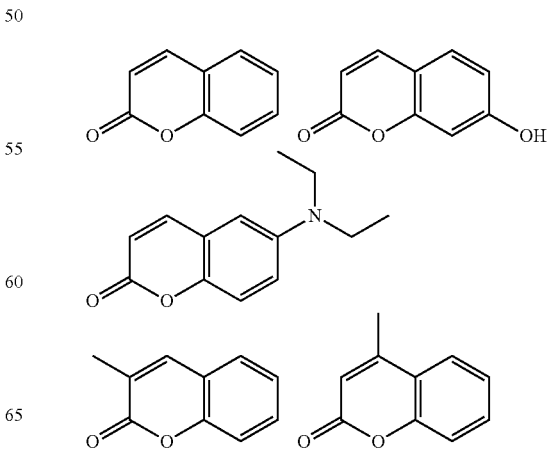

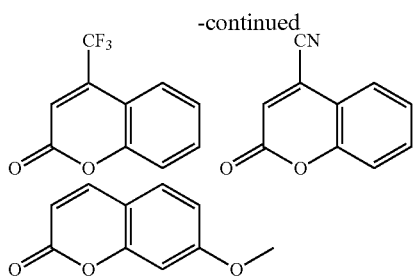

In the present specification, the alkyl group may be linear or branched, and the number of carbon atoms is not particularly limited, but is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

In the present specification, the amine group may be selected from the group consisting of —$NH_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and the number of carbon atoms is, although not particularly limited thereto, preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group. In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group may include a methylthioxy group, an ethylthioxy group, a tert-butylthioxy group, a hexylthioxy group, an octylthioxy group and the like, and the alkylsulfoxy group may include mesyl, an ethylsulfoxy group, a propylsulfoxy group, a butylsulfoxy group and the like, however, the examples are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —$BR_{100}R_{101}$, and $R_{100}$ and $R_{101}$ are the same as or different from each other and may be each independently selected from the group consisting of hydrogen; deuterium; a halogen group; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group, a dinaphthylphosphine oxide group and the like, but are not limited thereto.

In the present specification, the aryl group is not particularly limited, but preferably has 6 to 30 carbon atoms, and the aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted,

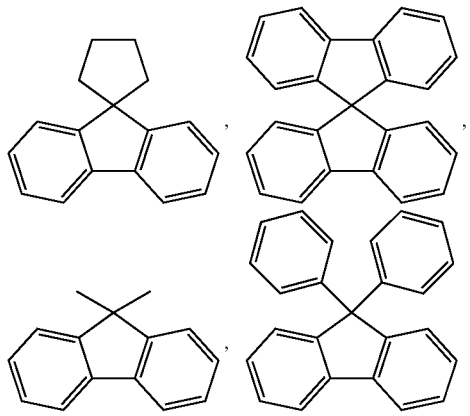

and the like may be included. However, the compound is not limited thereto.

In the present specification, an "adjacent" group may mean a substituent substituting an atom directly linking to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the aryloxy group, the arylthioxy group, the arylsulfoxy group, the N-alkylarylamine group, the N-arylheteroarylamine group and the arylphosphine group may be same as the examples of the aryl group described above. Specific examples of the aryloxy group may include a phenoxy group, a p-tolyloxy group, a m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the examples are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from the examples of the aryl group described above.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is favorably from 2 to 30, and the heteroaryl group may be monocyclic or multicyclic. Examples of the heterocyclic group may include a thiophene group, a furanyl group, a pyrrole group, an imidazolyl group, a thiazolyl group, an oxazolyl group, an oxadiazolyl group, a pyridyl group, a bipyridyl group, a pyrimidyl group, triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group may include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from the examples of the heteroraryl group described above.

In the present specification, examples of the heteroaryl group in the N-arylheteroarylamine group and the N-alkylheteroarylamine group are the same as the examples of the heteroaryl group described above.

In the present specification, in the substituted or unsubstituted ring formed by adjacent groups bonding to each other, the "ring" means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from the examples of the cycloalkyl group or the aryl group except for those that are not monovalent.

In the present specification, the aromatic ring may be monocyclic or multicyclic, and may be selected from the examples of the aryl group except for those that are not monovalent.

In the present specification, the heteroring is a ring including one or more atoms that are not carbon, that is, heteroatoms, and specifically, the heteroatom may include one or more atoms selected from the group consisting of O, N, Se, S and the like. The heteroring may be monocyclic or multicyclic, may be aromatic, aliphatic or a fused ring of aromatic and aliphatic, and may be selected from the examples of the heteroaryl group except for those that are not monovalent.

According to one embodiment of the present specification, in Chemical Formula 1, at least one of R2 and R5 is represented by Chemical Formula 2.

According to one embodiment of the present specification, in Chemical Formula 1, R2 is represented by Chemical Formula 2.

According to one embodiment of the present specification, in Chemical Formula 1, R5 is represented by Chemical Formula 2.

According to one embodiment of the present specification, in Chemical Formula 1, R2 and R5 are represented by Chemical Formula 2.

According to one embodiment of the present specification, Chemical Formula 1 is represented by the following Chemical Formula 1-1 or 1-2.

[Chemical Formula 1-1]

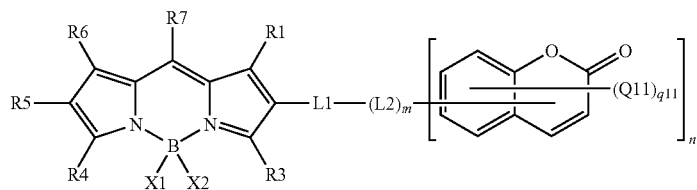

[Chemical Formula 1-2]

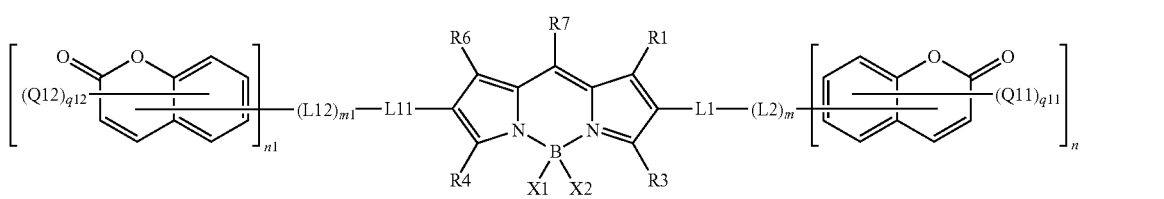

In Chemical Formulae 1-1 and 1-2, definitions of R1 to R7, and X1 and X2 are the same as in Chemical Formula 1, definitions of L1, L2, m and n are the same as in Chemical Formula 2, Q11 and Q12 are the same as or different from each other, and each independently hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring, L11 is represented by any one of Chemical Formulae 4 to 6, L12 is a direct bond; —O—; —N(H)—; —OC(=O)—; a substituted or unsubstituted alkylene group; a substituted or unsubstituted arylene group; or a substituted or unsubstituted heteroarylene group, q11, q12 and m1 are each an integer of 1 to 5, n1 is an integer of 1 to 3, and when q11, q12, m1 and n1 are each 2 or greater, the 2 or more structures in the parentheses are the same as or different from each other.

According to one embodiment of the present specification, Chemical Formula 1 is represented by any one of the following Chemical Formulae 1-3 to 1-8.

[Chemical Formula 1-3]

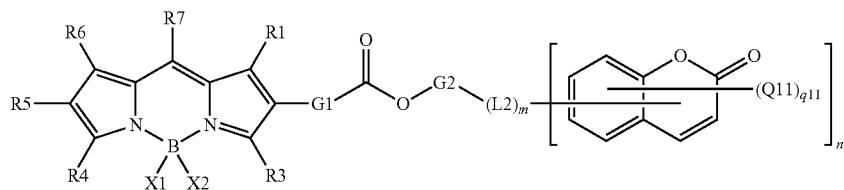

[Chemical Formula 1-4]

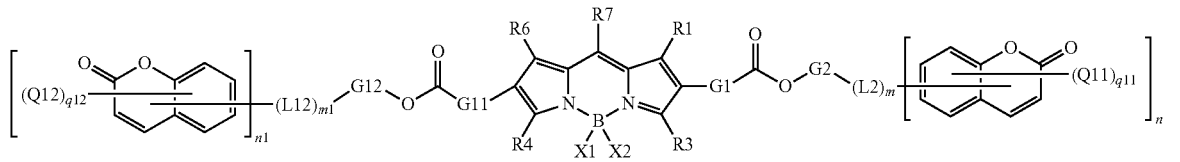

[Chemical Formula 1-5]

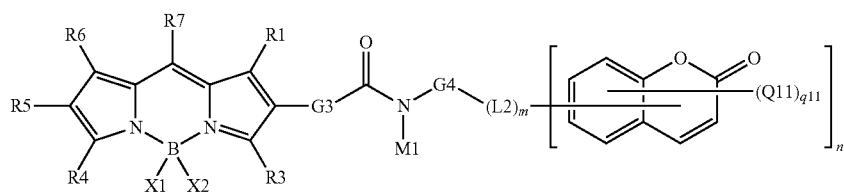

[Chemical Formula 1-6]

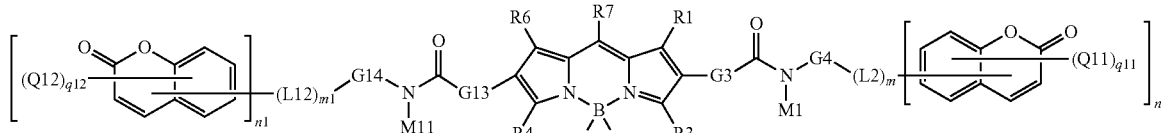

[Chemical Formula 1-7]

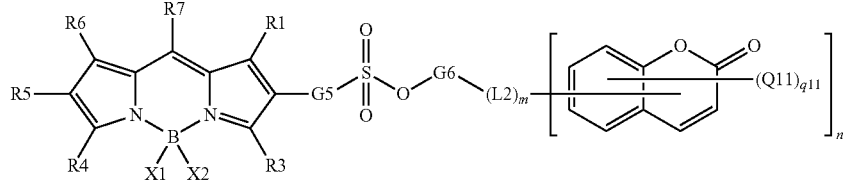

[Chemical Formula 1-8]

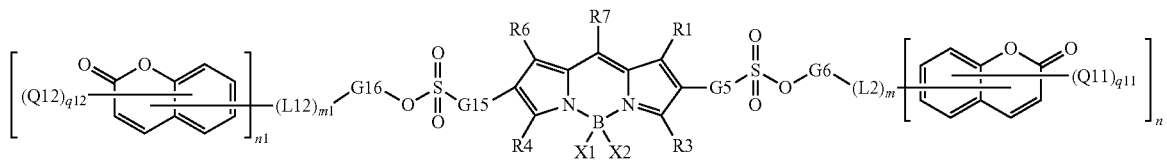

In Chemical Formulae 1-3 to 1-8, definitions of R1 to R7, and X1 and X2 are the same as in Chemical Formula 1, definitions of L1, L2, m and n are the same as in Chemical Formula 2, definitions of G1 and G2 are the same as in Chemical Formula 4, definitions of G3 and G4 are the same as in Chemical Formula 5, definitions of G5 and G6 are the same as in Chemical Formula 6, Q11 and Q12 are the same as or different from each other, and each independently hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring, L11 is represented by any one of Chemical Formulae 4 to 6, L12, and G11 to G16 are the same as or different from each other, and each independently a direct bond; —O—; —N(H)—; —OC(=O)—; a substituted or unsubstituted alkylene group; a substituted or unsubstituted arylene group; or a substituted or unsubstituted heteroarylene group, q11, q12 and m1 are each an integer of 1 to 5, n1 is an integer of 1 to 3, and when q11, q12, m1 and n1 are each 2 or greater, the 2 or more structures in the parentheses are the same as or different from each other.

According to one embodiment of the present specification, in Chemical Formula 1, X1 and X2 are the same as or different from each other, and each independently a halogen group; a nitrile group; a substituted or unsubstituted alkoxy group; —O(C=O)R; a substituted or unsubstituted alkynyl group; or a substituted or unsubstituted aryl group.

According to one embodiment of the present specification, in Chemical Formula 1, X1 and X2 are the same as or different from each other, and each independently a halogen group; a nitrile group; an alkoxy group unsubstituted or substituted with a halogen group; —O(C=O)R; an alkynyl group unsubstituted or substituted with a silyl group substituted with an alkyl group, an aryl group unsubstituted or substituted with an alkyl group, the group represented by Chemical Formula 3 or a heteroaryl group; or an aryl group unsubstituted or substituted with a halogen group, an alkyl group unsubstituted or substituted with a halogen group, an aryl group or a heteroaryl group.

According to one embodiment of the present specification, in Chemical Formula 1, X1 and X2 are the same as or different from each other, and each independently a halogen group; a nitrile group; a methoxy group; an n-butoxy group substituted with a halogen group; —O(C=O)R; an ethynyl group unsubstituted or substituted with a silyl group substituted with an alkyl group, an aryl group unsubstituted or substituted with an alkyl group, the group represented by Chemical Formula 3 or a heteroaryl group; a phenyl group unsubstituted or substituted with a halogen group, an alkyl group unsubstituted or substituted with a halogen group, an aryl group or a heteroaryl group; or a fluorenyl group unsubstituted or substituted with an alkyl group.

According to another embodiment of the present specification, R is a substituted or unsubstituted alkyl group.

According to another embodiment of the present specification, R is an alkyl group unsubstituted or substituted with a halogen group.

According to another embodiment of the present specification, R is a methyl group unsubstituted or substituted with a halogen group.

According to one embodiment of the present specification, in Chemical Formula 1, X1 and X2 are the same as or different from each other, and each independently fluorine; a nitrile group; a methoxy group; an n-butoxy group substituted with fluorine; —O(C=O)CH$_3$; —O(C=O)CF$_3$; an ethynyl group unsubstituted or substituted with a silyl group substituted with a methyl group, a silyl group substituted with an isopropyl group, a phenyl group substituted with a t-butyl group, a pyrenyl group, a coumarine group or a dibenzofuran group; a phenyl group unsubstituted or substituted with fluorine, a methyl group unsubstituted or substituted with fluorine, a t-butyl group, a naphthyl group or a carbazolyl group; or a fluorenyl group unsubstituted or substituted with a methyl group.

According to one embodiment of the present specification, L is a direct bond; —O—; an alkylene group; an arylene group; or a heteroarylene group.

According to one embodiment of the present specification, L is a direct bond; —O—; a methylene group; an ethylene group; an n-propylene group; an n-butylene group; a phenylene group; a biphenylylene group; a terphenylene group or a triazolylene group.

According to one embodiment of the present specification, A is a halogen group; a nitrile group; an ester group; a carboxyl group (—COOH); an alkyl group unsubstituted or substituted with a halogen group; an alkoxy group; or the group represented by Chemical Formula 3.

According to one embodiment of the present specification, A is fluorine; a nitrile group; an alkylester group; a carboxyl group (—COOH); an alkyl group unsubstituted or substituted with fluorine; an alkoxy group; or the group represented by Chemical Formula 3.

According to one embodiment of the present specification, A is fluorine; a nitrile group; a methylester group; a carboxyl group (—COOH); a methyl group unsubstituted or substituted with fluorine; a t-butyl group; a methoxy group; a hexyloxy group, a coumarine group; or a coumarine group substituted with a methyl group substituted with fluorine.

According to one embodiment of the present specification, in Chemical Formula 1, at least one of R1 to R6 is represented by Chemical Formula 2, and the rest are the same as or different from each other and each independently hydrogen; an alkyl group unsubstituted or substituted with a halogen group; an aryl group unsubstituted or substituted with one or more selected from the group consisting of a halogen group, an alkyl group substituted with an aryl group, an alkyl group unsubstituted or substituted with a halogen group, the group represented by Chemical Formula 3, an alkoxy group, an aryl group, and a heteroaryl group unsubstituted or substituted with an aryl group; a heteroaryl group unsubstituted or substituted with an aryl group; or the group represented by Chemical Formula 3.

According to one embodiment of the present specification, in Chemical Formula 1, at least one of R1 to R6 is represented by Chemical Formula 2, and the rest are the same as or different from each other and each independently hydrogen; an alkyl group unsubstituted or substituted with a halogen group; a phenyl group unsubstituted or substituted with one or more selected from the group consisting of a halogen group, an alkyl group substituted with an aryl group, an alkyl group unsubstituted or substituted with a halogen group, the group represented by Chemical Formula 3, an alkoxy group, an aryl group, and a heteroaryl group unsubstituted or substituted with an aryl group; a naphthyl group; a pyrenyl group; a fluorenyl group substituted with an alkyl group; a carbazolyl group unsubstituted or substituted with an aryl group; a dibenzofuran group; or a coumarine group unsubstituted or substituted with an alkylamine group.

According to one embodiment of the present specification, in Chemical Formula 1, at least one of R1 to R6 is represented by Chemical Formula 2, and the rest are the same as or different from each other and each independently hydrogen; a methyl group unsubstituted or substituted with a halogen group; a phenyl group unsubstituted or substituted with one or more selected from the group consisting of a halogen group, an alkyl group substituted with an aryl group, an alkyl group unsubstituted or substituted with a halogen group, the group represented by Chemical Formula 3, an alkoxy group, an aryl group, and a heteroaryl group unsubstituted or substituted with an aryl group; a naphthyl group; a pyrenyl group; a fluorenyl group substituted with an alkyl group; a carbazolyl group unsubstituted or substituted with an aryl group; a dibenzofuran group; or a coumarine group unsubstituted or substituted with an alkylamine group.

According to one embodiment of the present specification, in Chemical Formula 1, at least one of R1 to R6 is represented by Chemical Formula 2, and the rest are the same as or different from each other and each independently hydrogen; a methyl group unsubstituted or substituted with fluorine; a phenyl group unsubstituted or substituted with one or more selected from the group consisting of fluorine, a t-butyl group, a methyl group substituted with a phenyl group, a methyl group substituted with fluorine, a methoxy group, a triazinyl group substituted with a phenyl group and a coumarine group; a naphthyl group; a pyrenyl group; a fluorenyl group substituted with a methyl group; a carbazolyl group unsubstituted or substituted with a phenyl group; a coumarine group unsubstituted or substituted with a dibenzofuran group or a diethylamine group.

According to one embodiment of the present specification, in Chemical Formula 2, L2 is a direct bond; —O—; —N(H)—; —OC(=O)—; an alkylene group; an arylene group; or a heteroarylene group.

According to one embodiment of the present specification, in Chemical Formula 2, L2 is a direct bond; —O—; —N(H)—; —OC(=O)—; a methylene group; an ethylene group; an n-propylene group; an isopropylene group; an n-butylene group; a t-butylene group; a hexylene group; a phenylene group; or a triazolylene group.

According to one embodiment of the present specification, in Chemical Formulae 4 to 6, G1 to G6 are the same as or different from each other, and each independently a direct bond; or an alkylene group.

According to one embodiment of the present specification, in Chemical Formulae 4 to 6, G1 to G6 are the same as or different from each other, and each independently a direct bond; a methylene group; or an ethylene group.

According to one embodiment of the present specification, in Chemical Formula 3, any one of Q1 to Q6 is a site bonding to L2 of Chemical Formula 2, or a site bonding to any one of R1 to R7 of Chemical Formula 1, and the rest are the same as or different from each other and each independently hydrogen; a halogen group; an alkyl group unsubstituted or substituted with a halogen group; or a dialkylamine group.

According to one embodiment of the present specification, in Chemical Formula 3, any one of Q1 to Q6 is a site bonding to L2 of Chemical Formula 2, or a site bonding to any one of R1 to R7 of Chemical Formula 1, and the rest are the same as or different from each other and each independently hydrogen; a halogen group; a methyl group unsubstituted or substituted with a halogen group; an ethyl group; a methoxy group; or a diethylamine group.

According to one embodiment of the present specification, in Chemical Formula 3, any one of Q1 to Q6 is a site bonding to L2 of Chemical Formula 2, or a site bonding to any one of R1 to R7 of Chemical Formula 1, and the rest are the same as or different from each other and each independently hydrogen; chlorine; a methyl group unsubstituted or substituted with fluorine; an ethyl group; a methoxy group; or a diethylamine group.

According to one embodiment of the present specification, in Chemical Formula 3, any one of Q1 to Q6 is a site bonding to L2 of Chemical Formula 2, or a site bonding to any one of R1 to R7 of Chemical Formula 1, and adjacent two or more groups of the rest bond to each other to form a substituted or unsubstituted heteroring.

According to one embodiment of the present specification, in Chemical Formula 3, any one of Q1 to Q6 is a site bonding to L2 of Chemical Formula 2, or a site bonding to any one of R1 to R7 of Chemical Formula 1, and adjacent two or more groups of the rest bond to each other to form a hexahydroquinolizine ring.

According to one embodiment of the present specification, in Chemical Formula 3, Q2, Q3 and Q4 bond to each other to form a hexahydroquinolizine ring.

According to one embodiment of the present specification, the compound represented by Chemical Formula 1 has a maximum light emission peak present in 500 nm to 550 nm in a film state. Such a compound emits green light.

According to one embodiment of the present specification, the compound represented by Chemical Formula 1 has a maximum light emission peak present in 500 nm to 550 nm in a film state, and the light emission peak has a full width at half maximum of 50 nm or less. Having such a small full width at half maximum may further increase color gamut. Herein, the compound represented by Chemical Formula 1 favorably has a light emission peak with a smaller full width at half maximum.

According to one embodiment of the present specification, the compound represented by Chemical Formula 1 has a maximum light emission peak present in 600 nm to 650 nm in a film state. Such a compound emits red light.

According to one embodiment of the present specification, the compound represented by Chemical Formula 1 has a maximum light emission peak present in 600 nm to 650 nm in a film state, and the light emission peak has a full width at half maximum of 60 nm or less. Having such a small full width at half maximum may further increase color gamut. Herein, the compound represented by Chemical Formula 1 may have a light emission peak with a full width at half maximum of 5 nm or greater.

According to one embodiment of the present specification, the compound represented by Chemical Formula 1 has quantum efficiency of 0.8 or greater.

In the present specification, the "film state" means, instead of a solution state, a state prepared to a film form with the compound represented by Chemical Formula 1 alone or by mixing the compound represented by Chemical Formula 1 with other components that do not affect full width at half maximum and quantum efficiency measurements.

In the present specification, the full width at half maximum means a width of a light emission peak at a half of the maximum height in a maximum light emission peak of the light emitting from the compound represented by Chemical Formula 1.

In the present specification, the quantum efficiency may be measured using methods known in the art, and for example, may be measured using an integrating sphere.

According to one embodiment of the present specification, Chemical Formula 1 is selected from among the following compounds.

compound 1-1

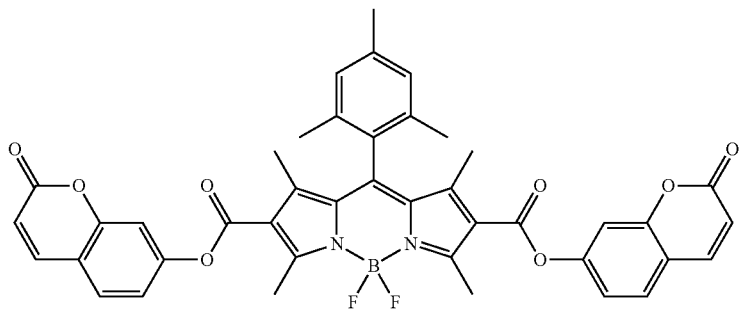

compound 1-2

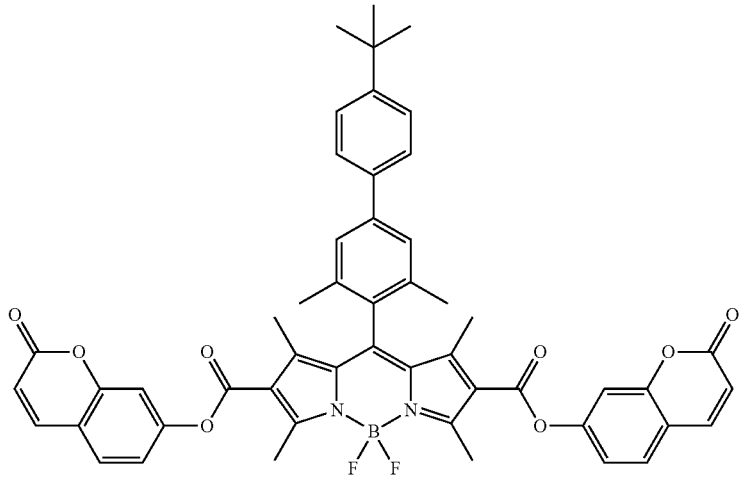

-continued
compound 1-3
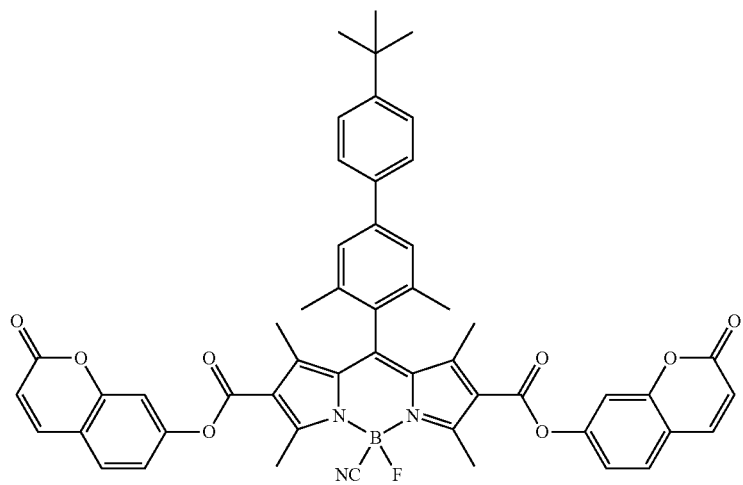
compound 1-4
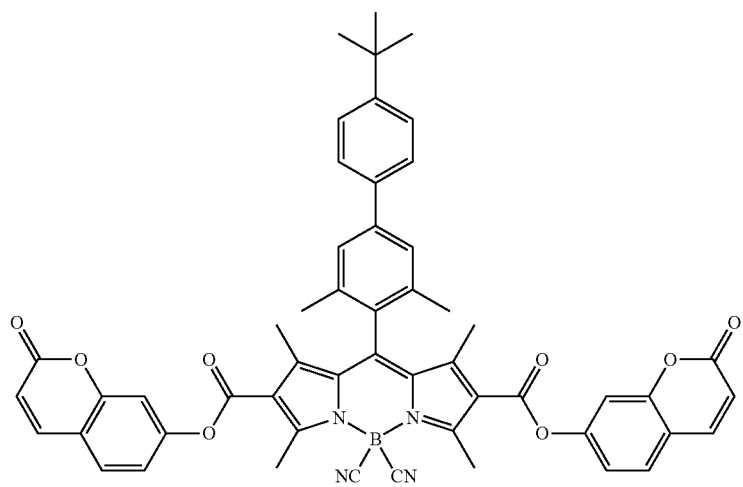
compound 1-5
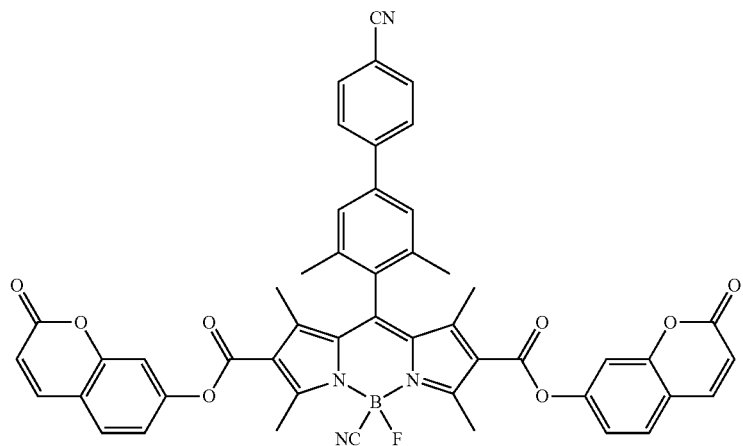

-continued
compound 1-6
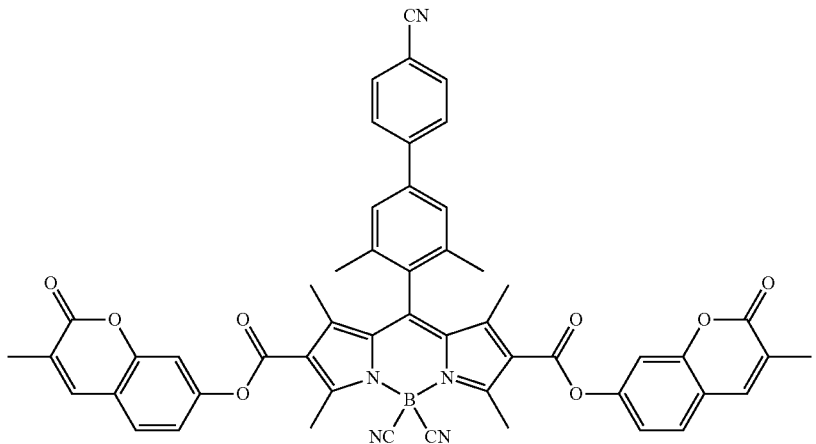
compound 1-7
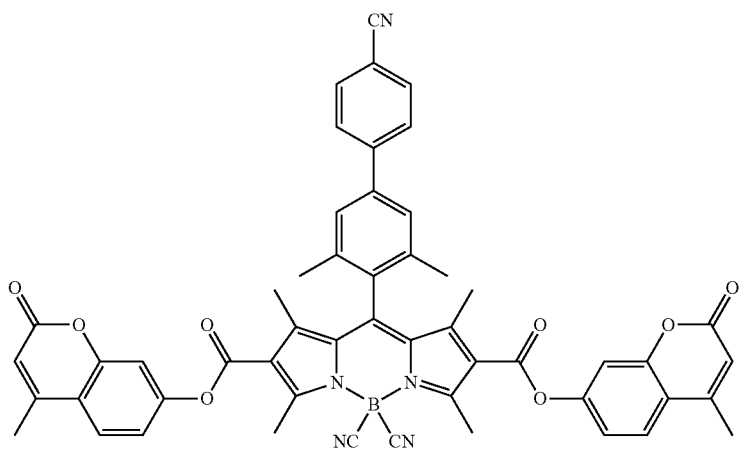
compound 1-8
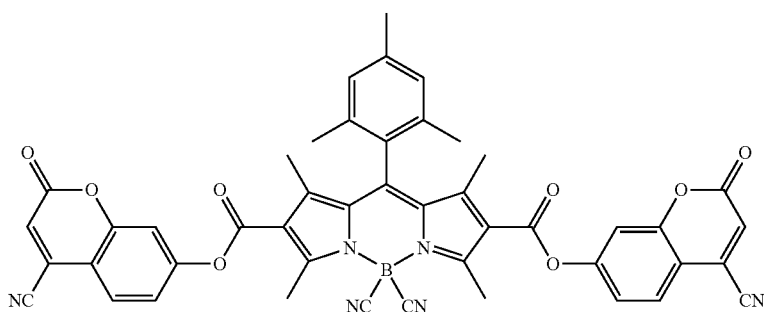

compound 1-9
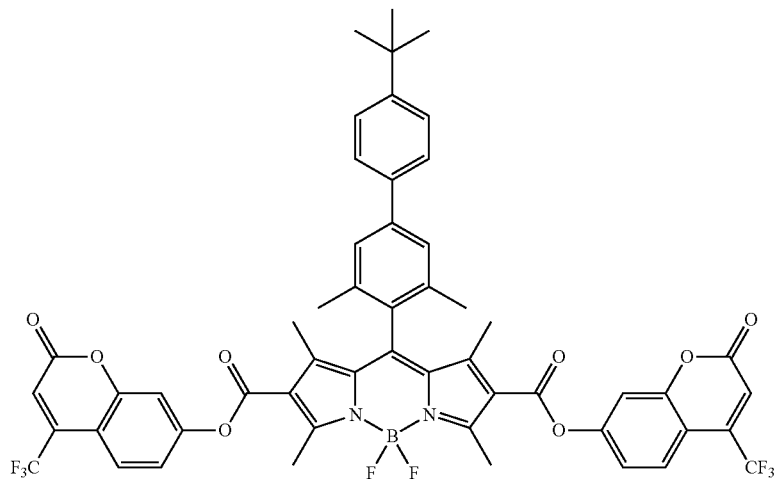
compound 1-10
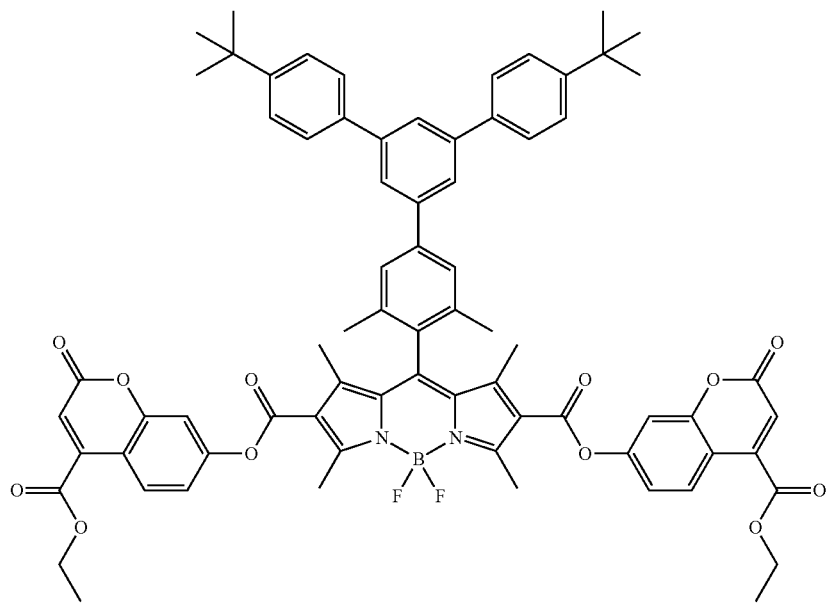
compound 1-11
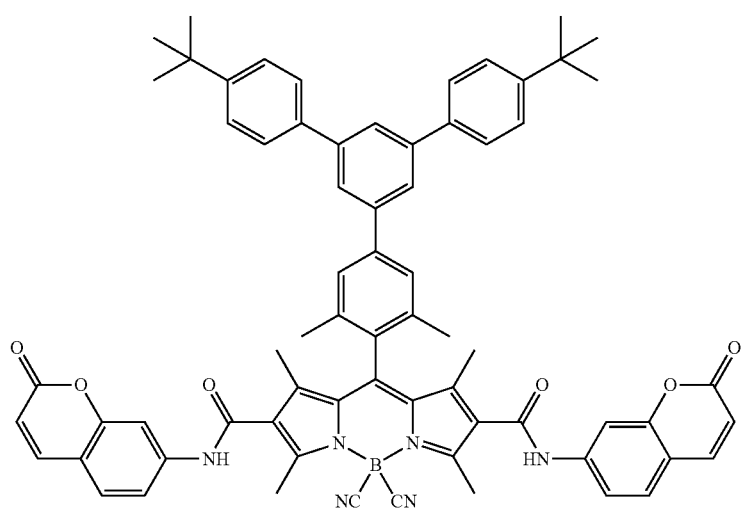

-continued
compound 1-12
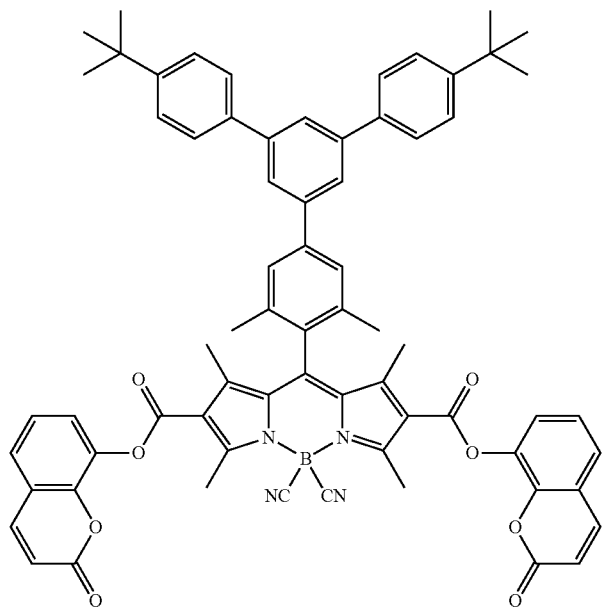
compound 1-13
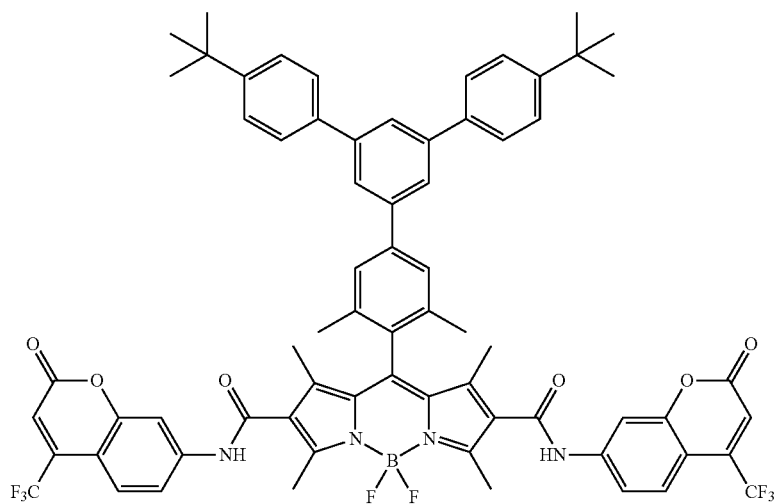
compound 1-14
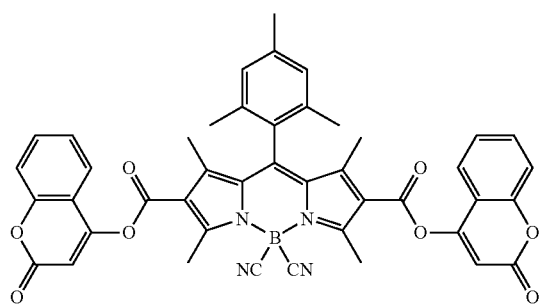
compound 1-15
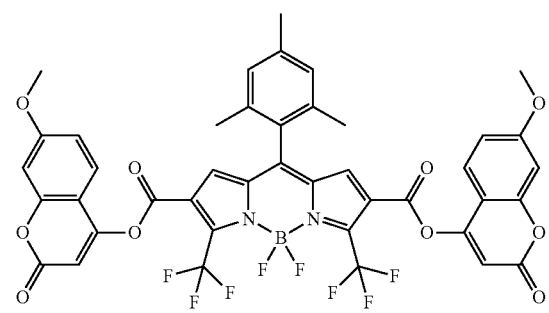

compound 1-16
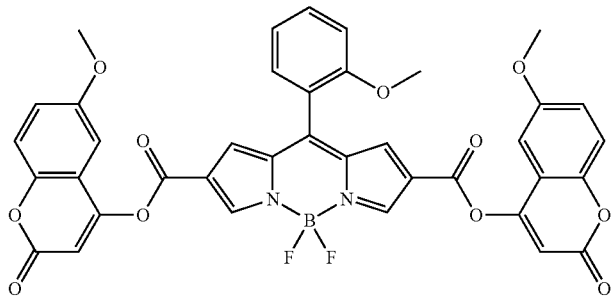
compound 1-17
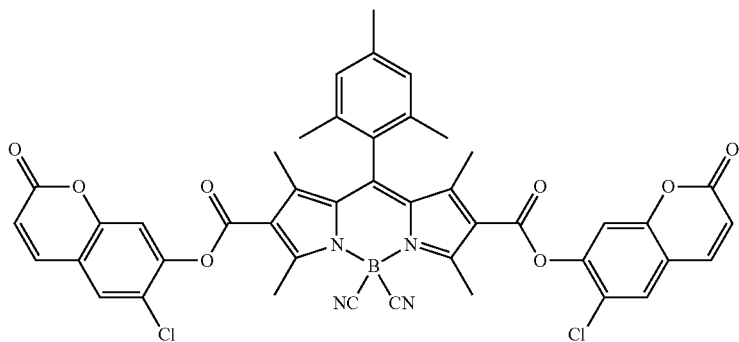
compound 1-18
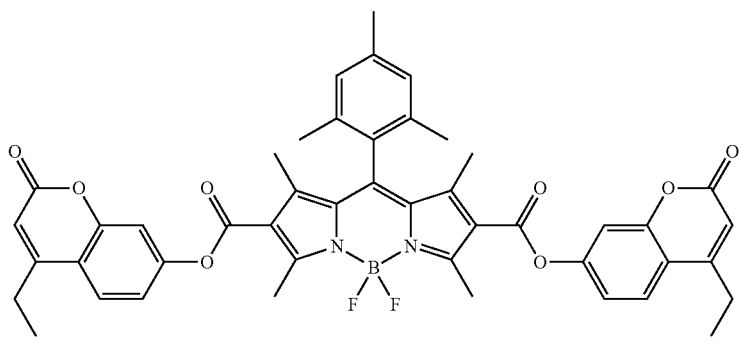
compound 1-19
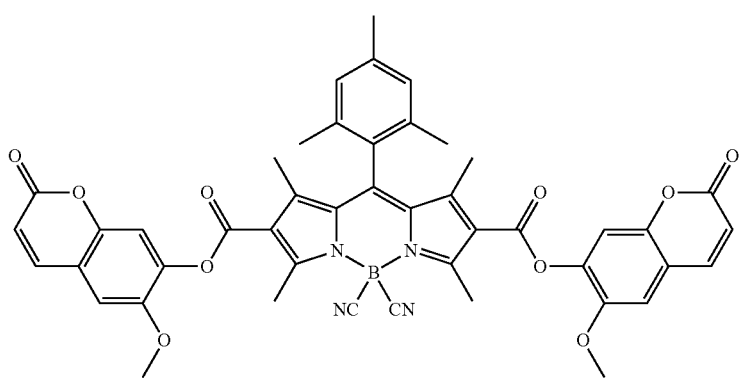

-continued
compound 1-20
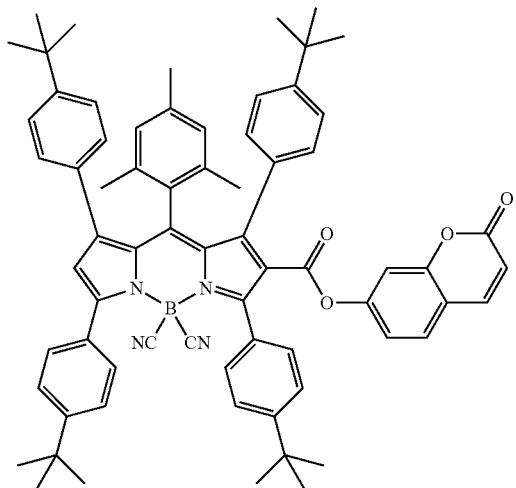
compound 1-21
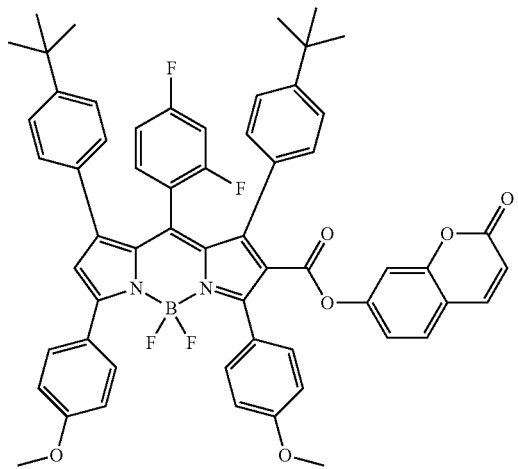
compound 1-22
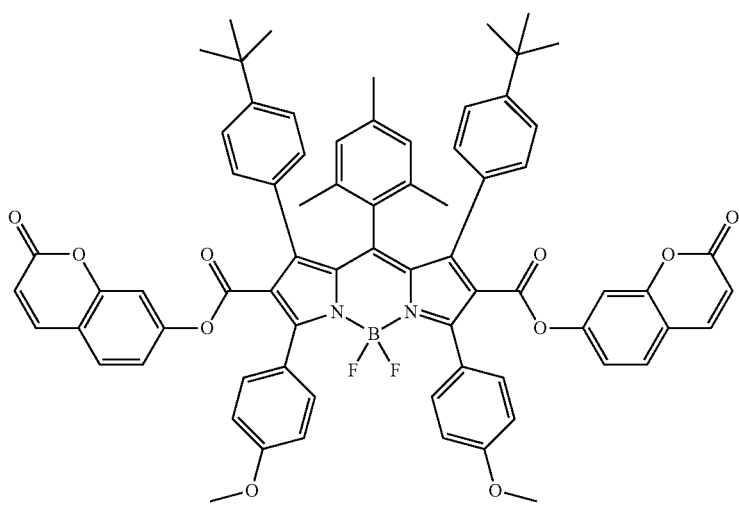
compound 1-23
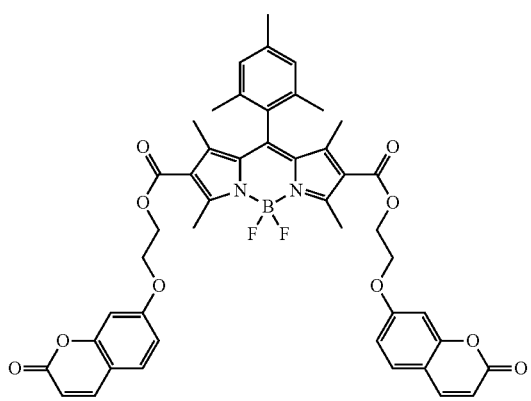
compound 1-24
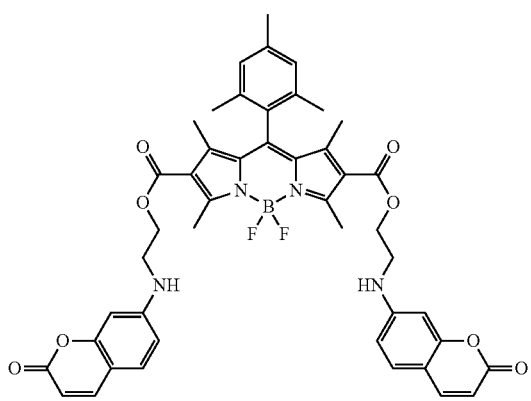

compound 1-25
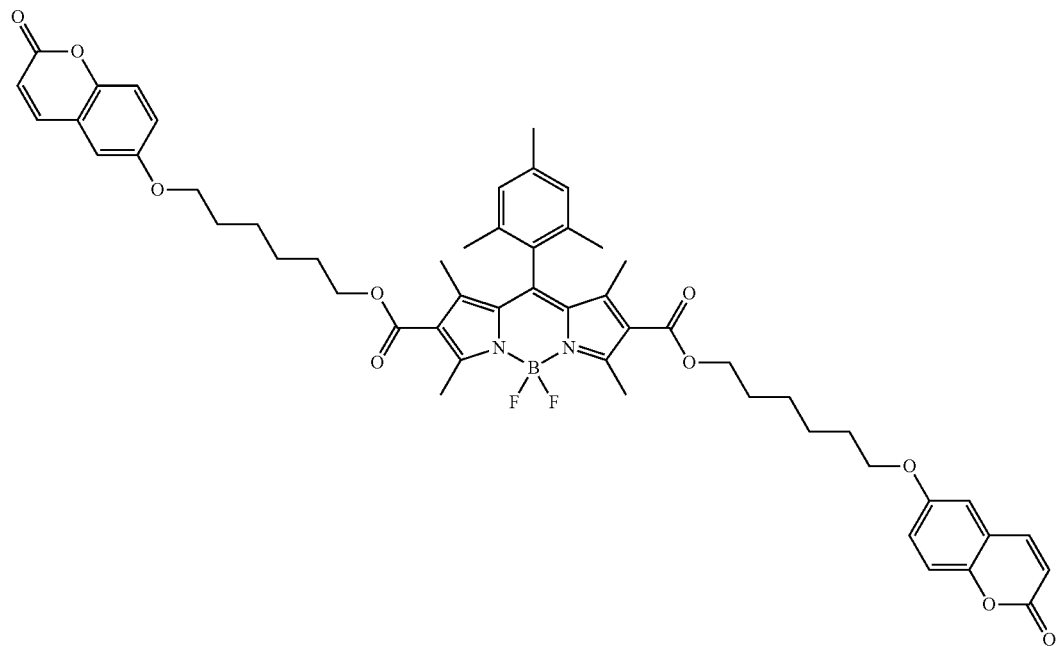
compound 1-26
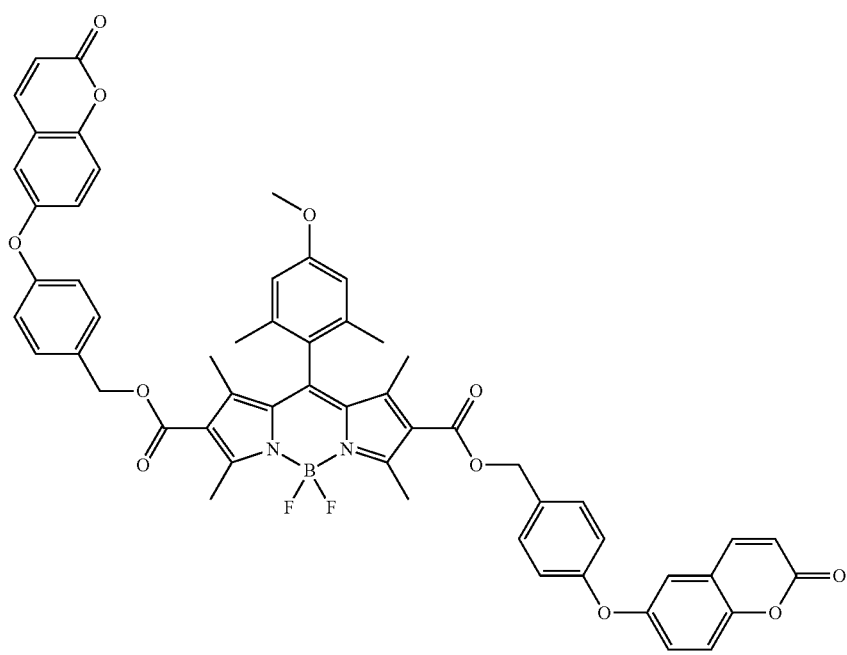

-continued
compound 1-27
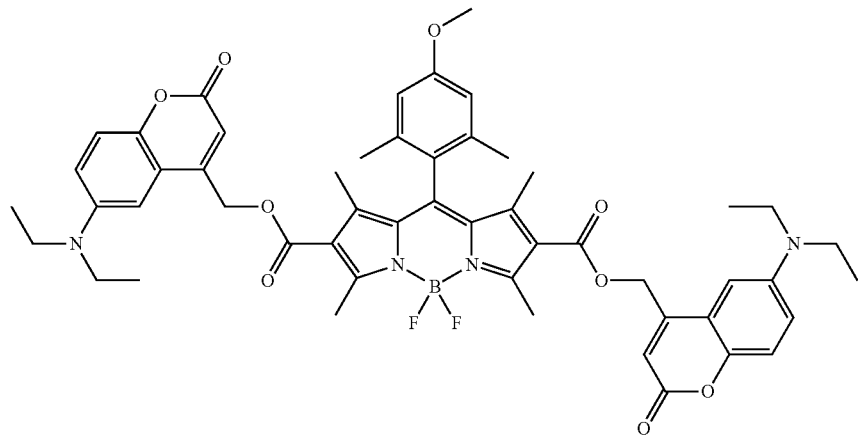
compound 1-28
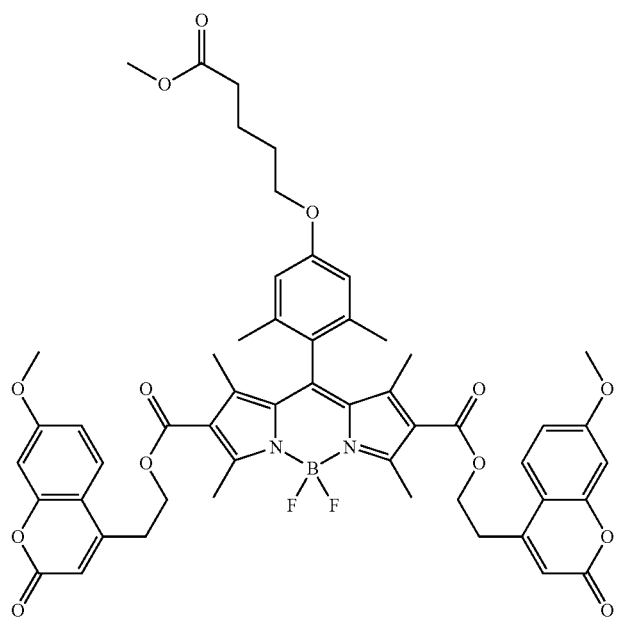
compound 1-29
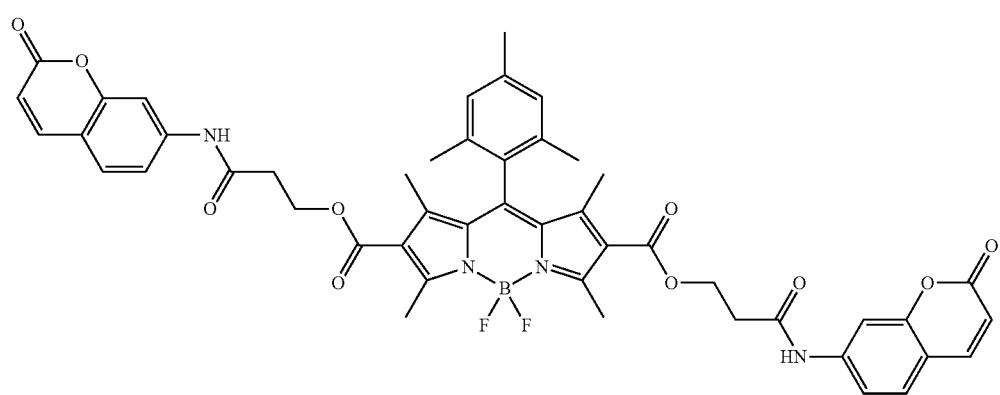

-continued
compound 1-30
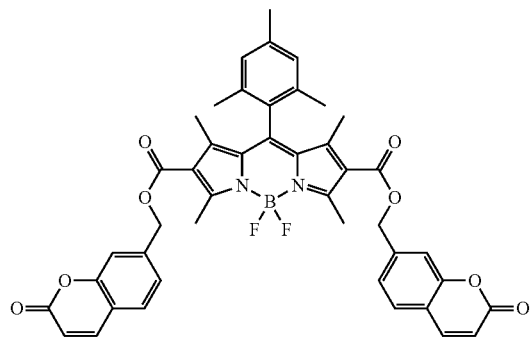
compound 1-31
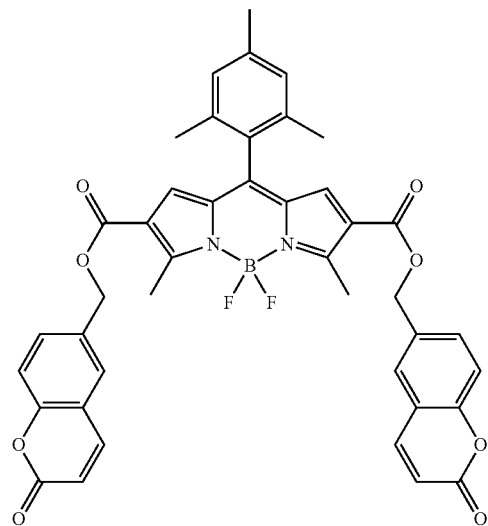
compound 1-32
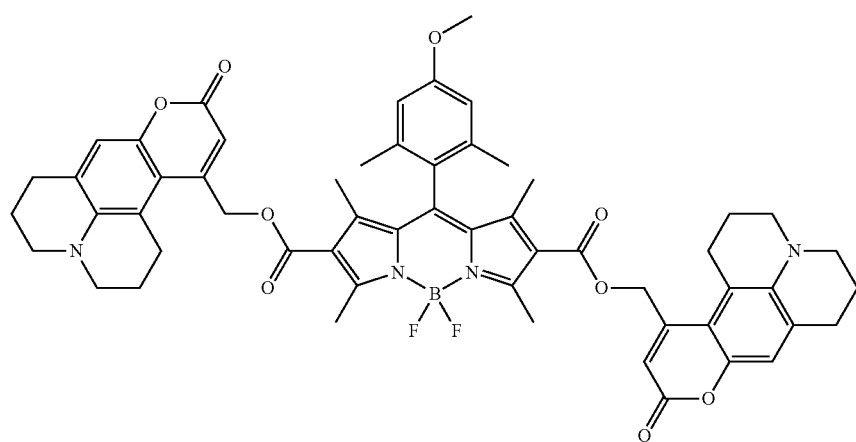
compound 1-33
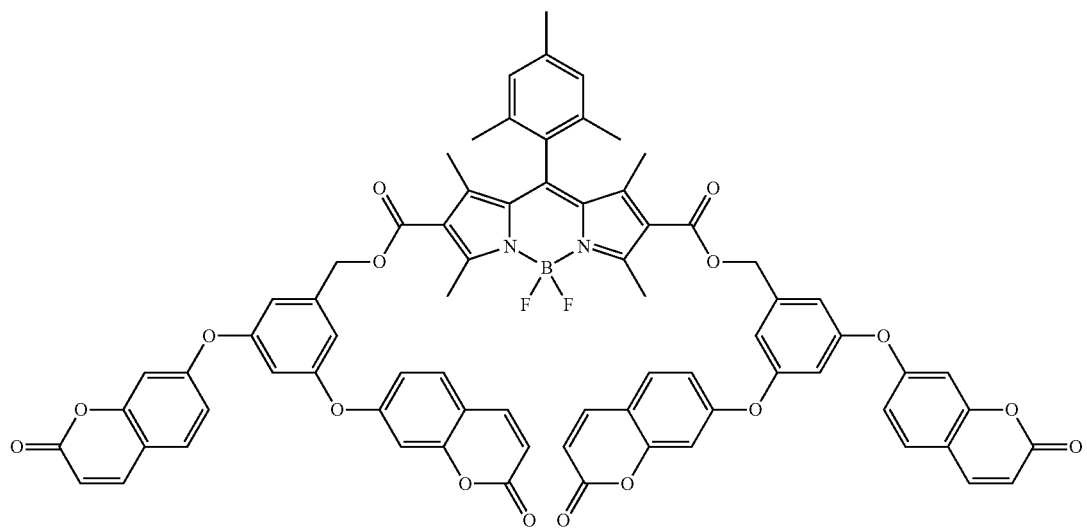

compound 1-34
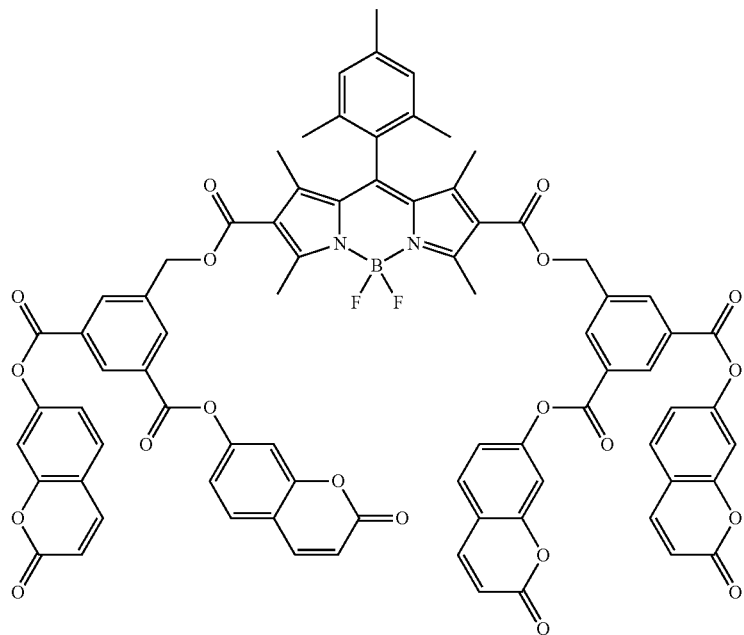
compound 1-35
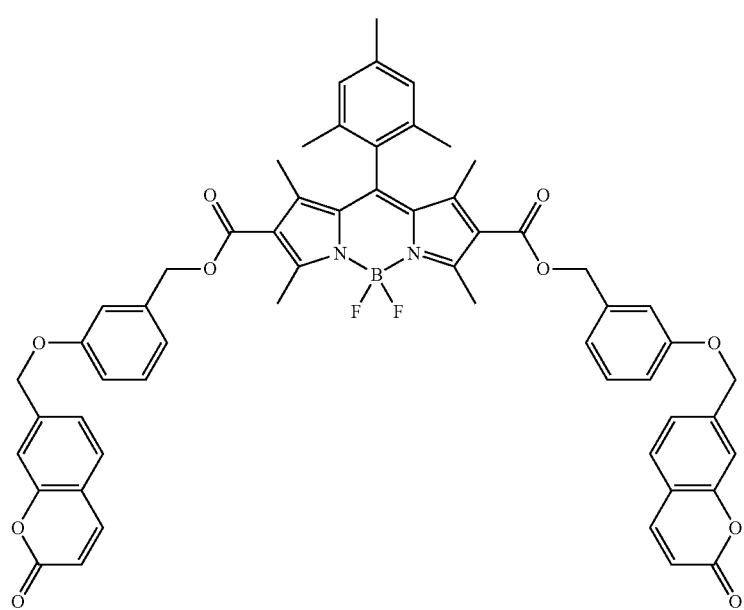

compound 1-36
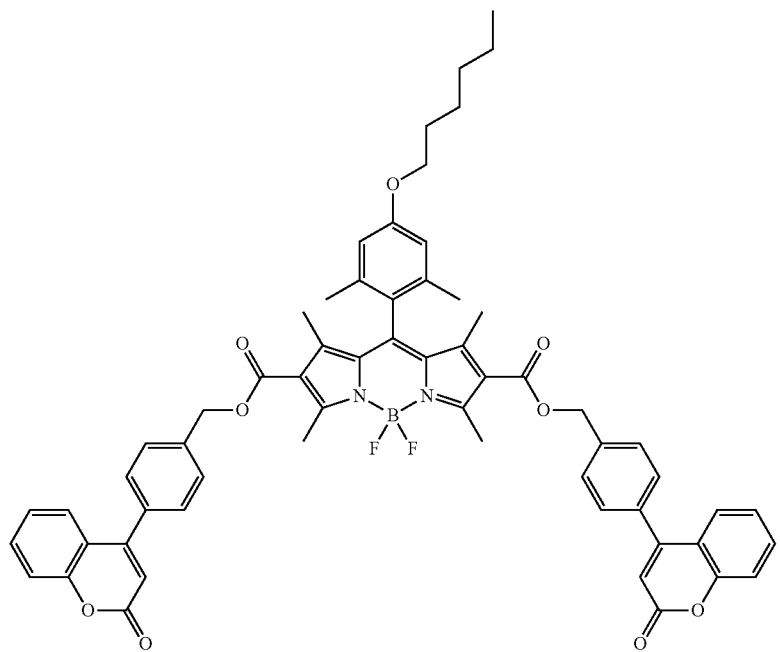
compound 1-37
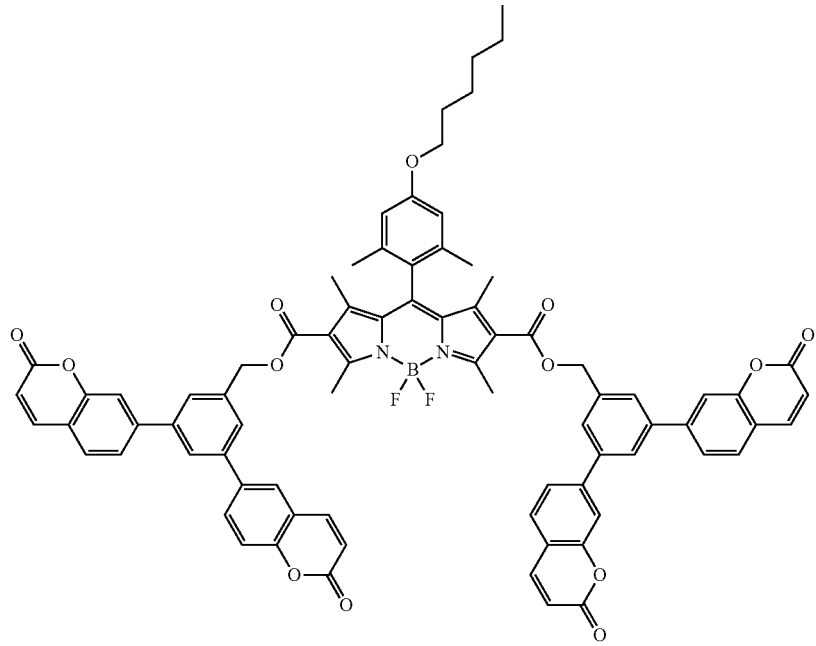

compound 1-38
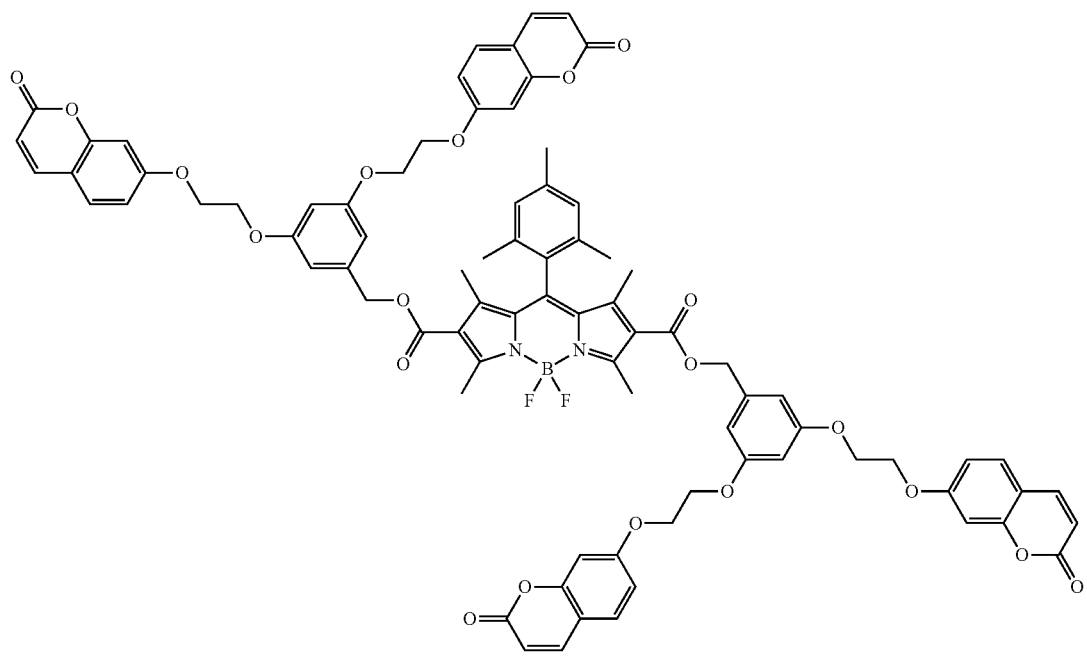
compound 1-39
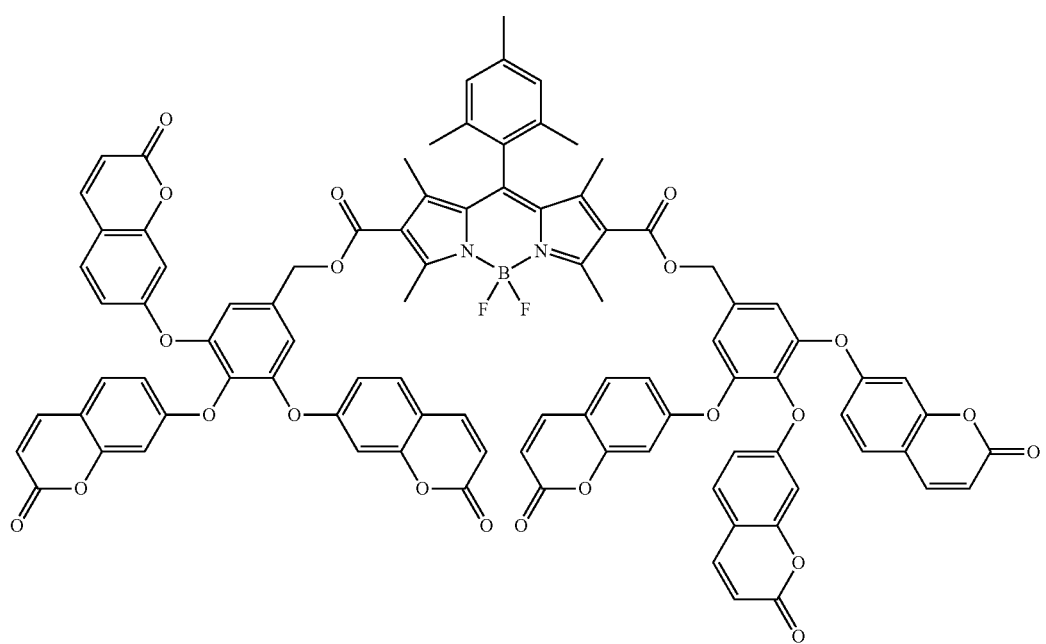

compound 1-40
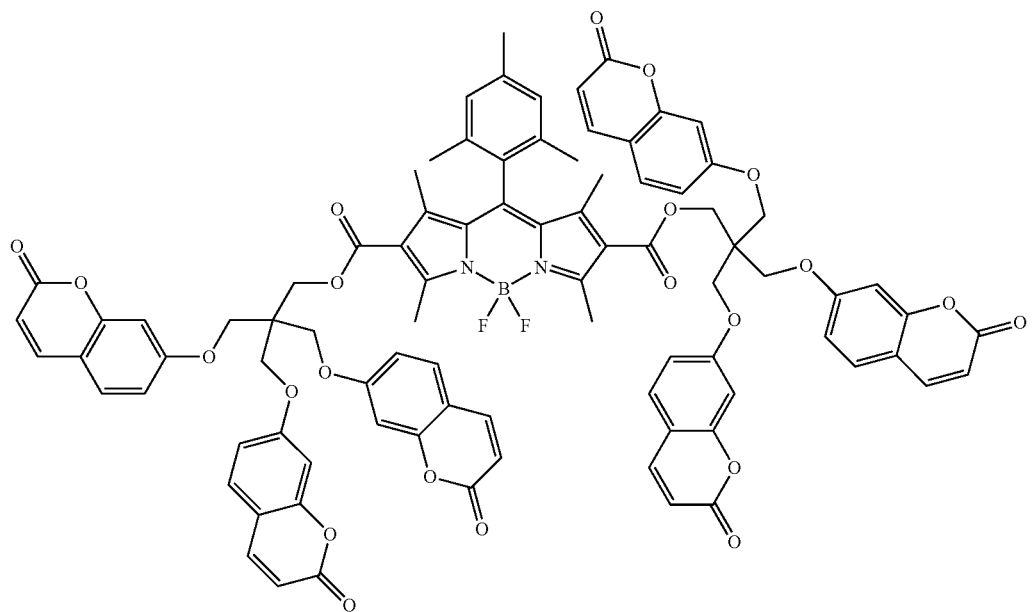
compound 1-41
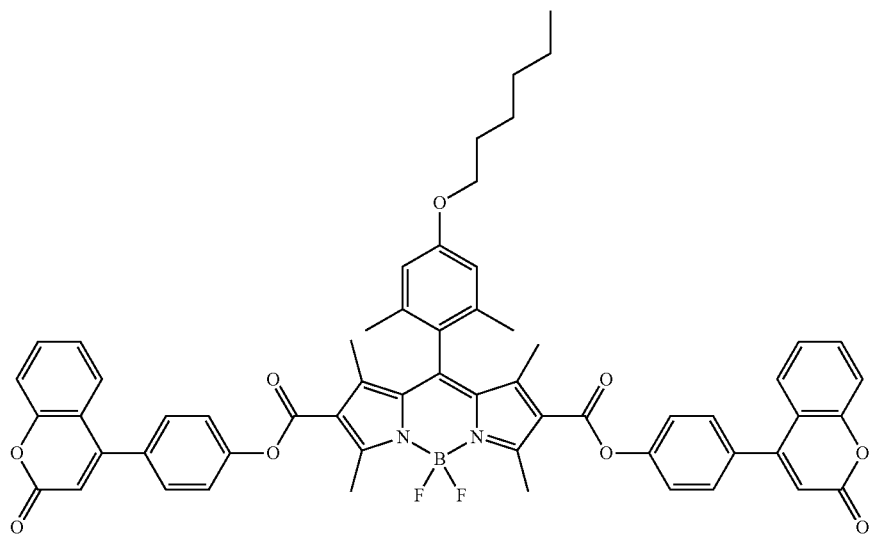
compound 1-42
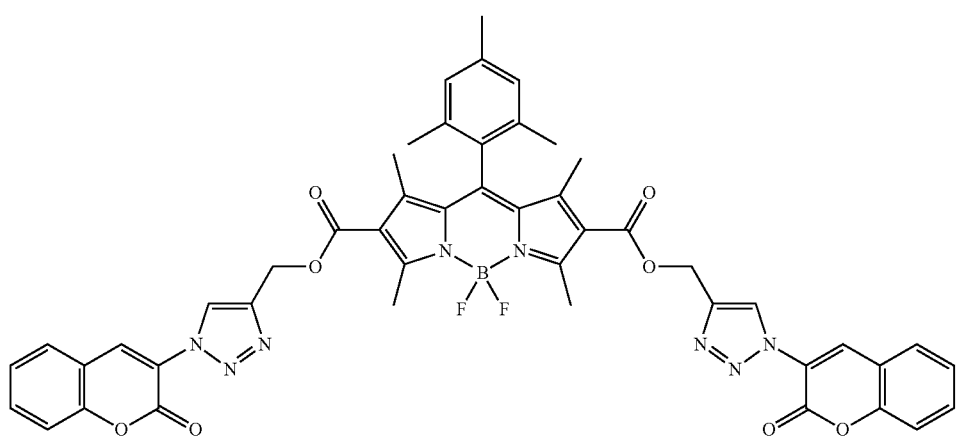

-continued
compound 1-43
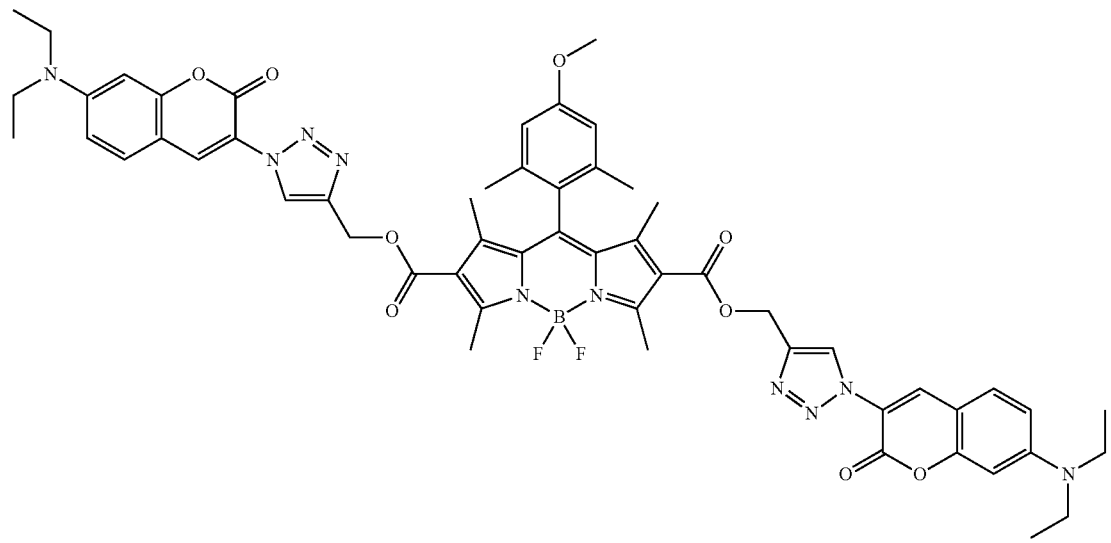
compound 1-44
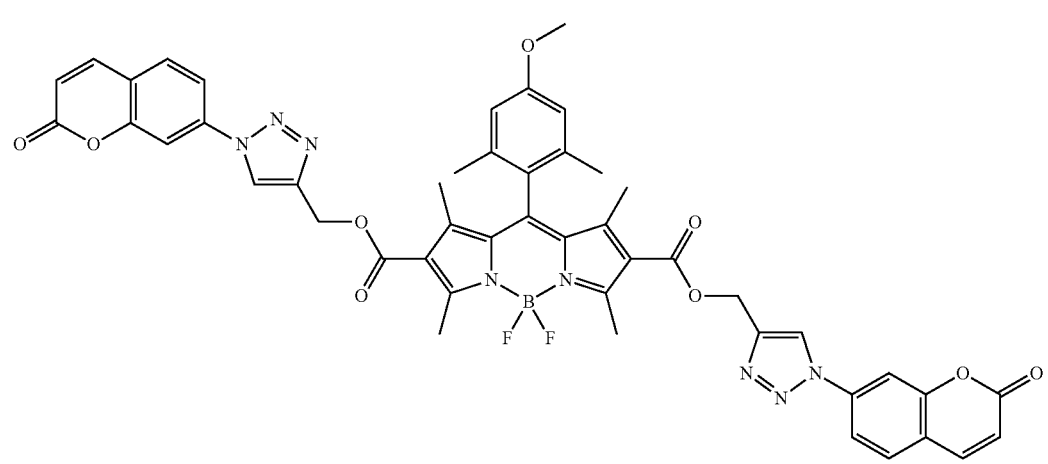
compound 1-45
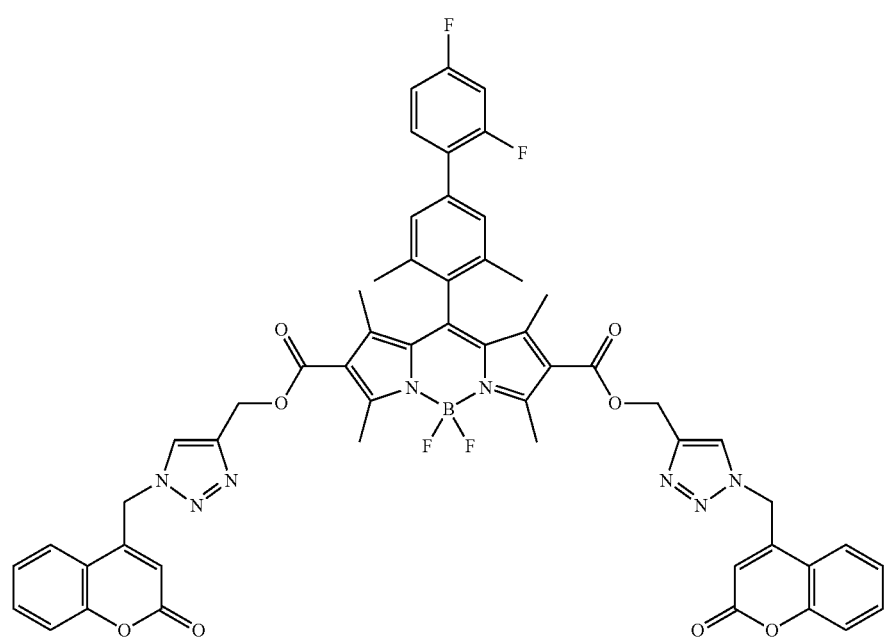

-continued
compound 1-46
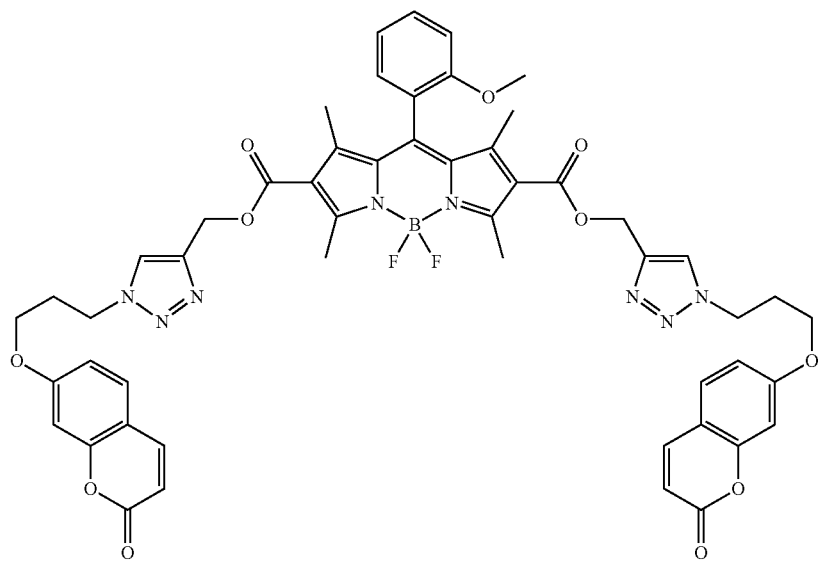
compound 1-47
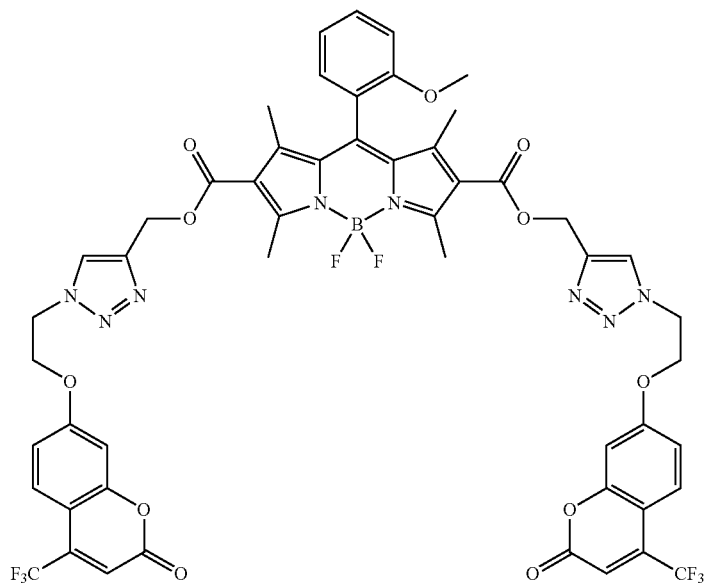
compound 1-48
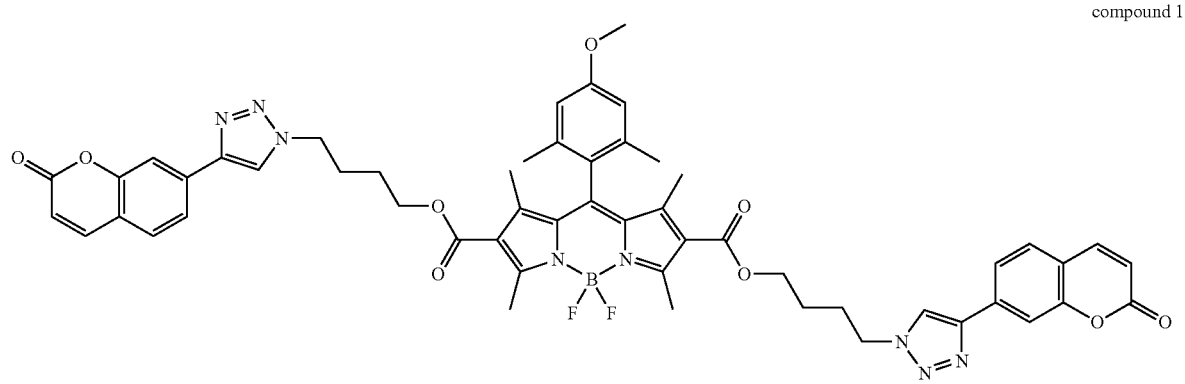

-continued
compound 1-49
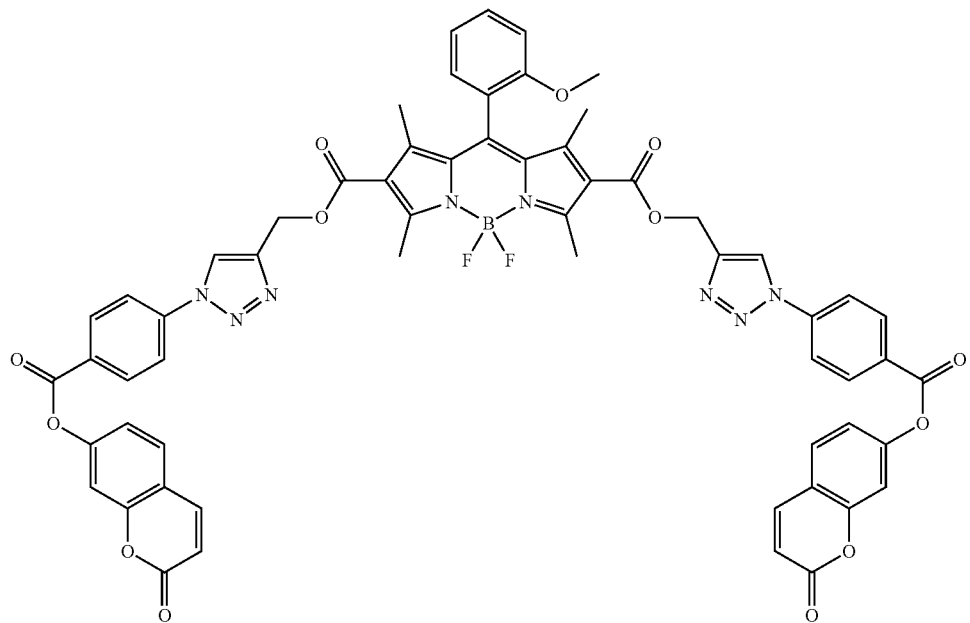
compound 1-50
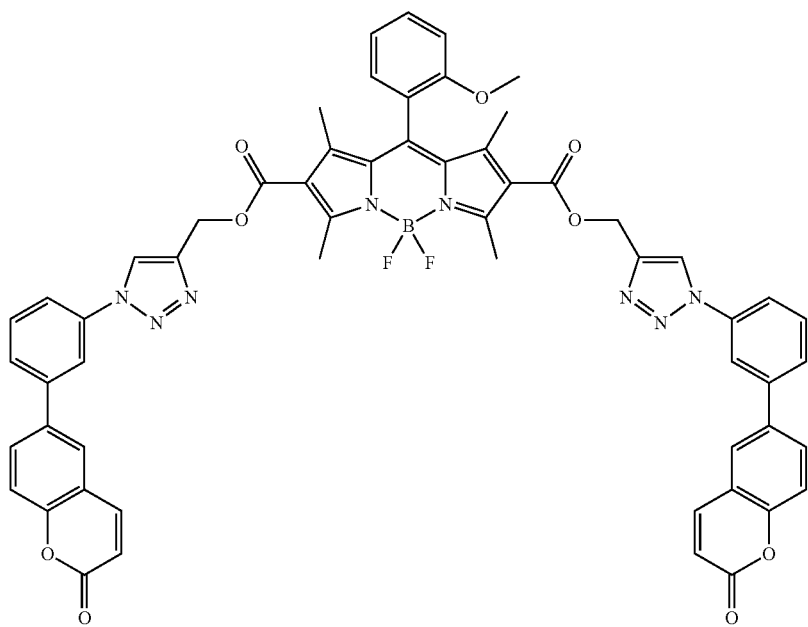

-continued
compound 1-51
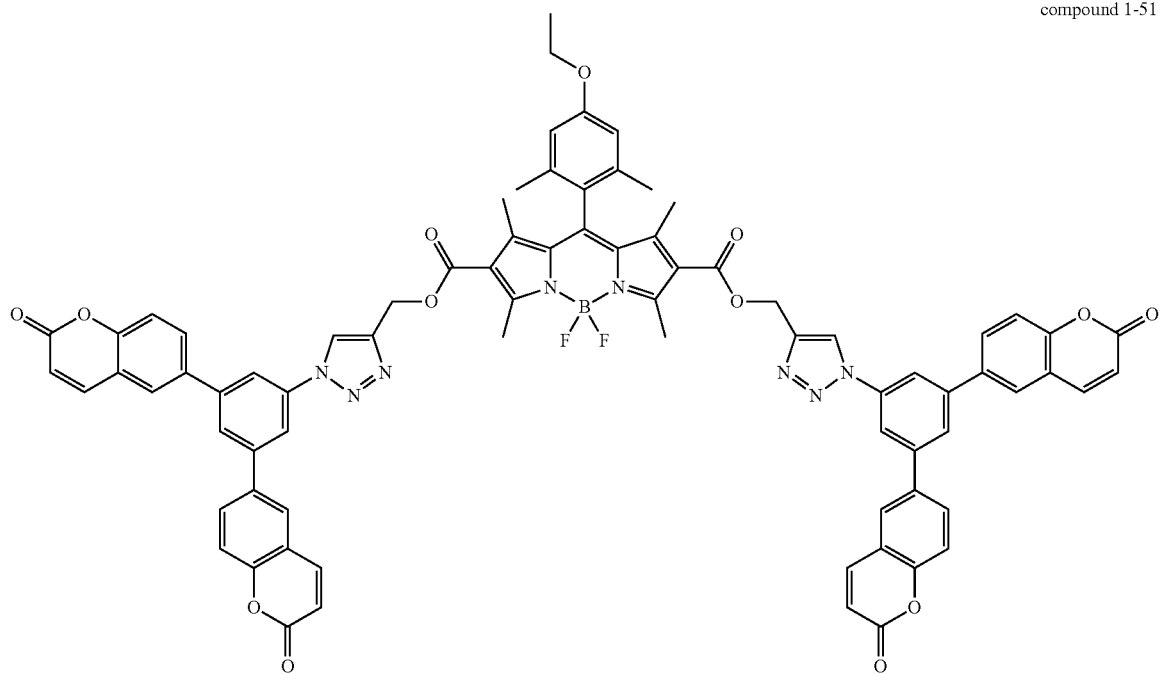
compound 1-52
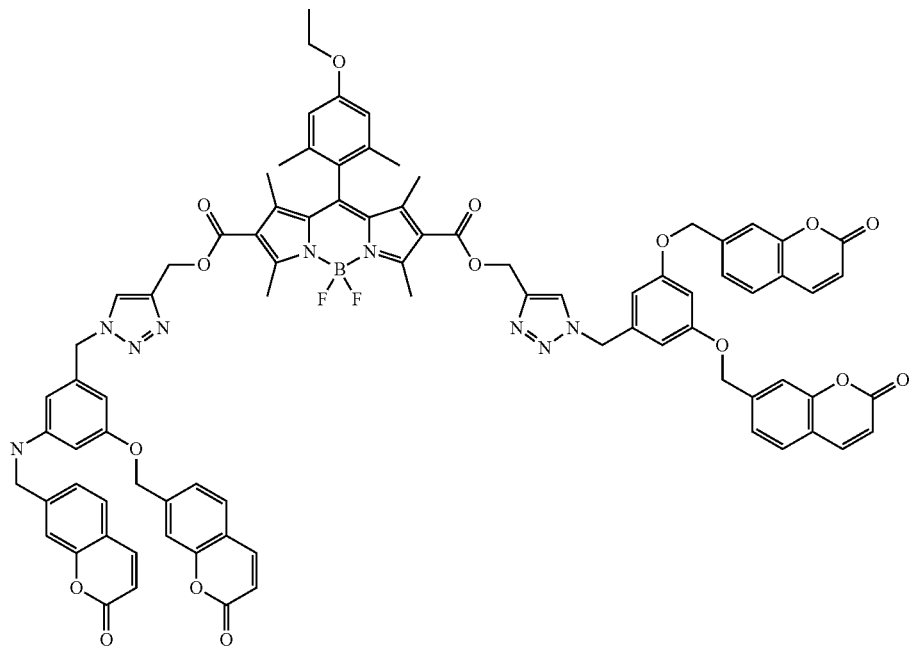

compound 1-53
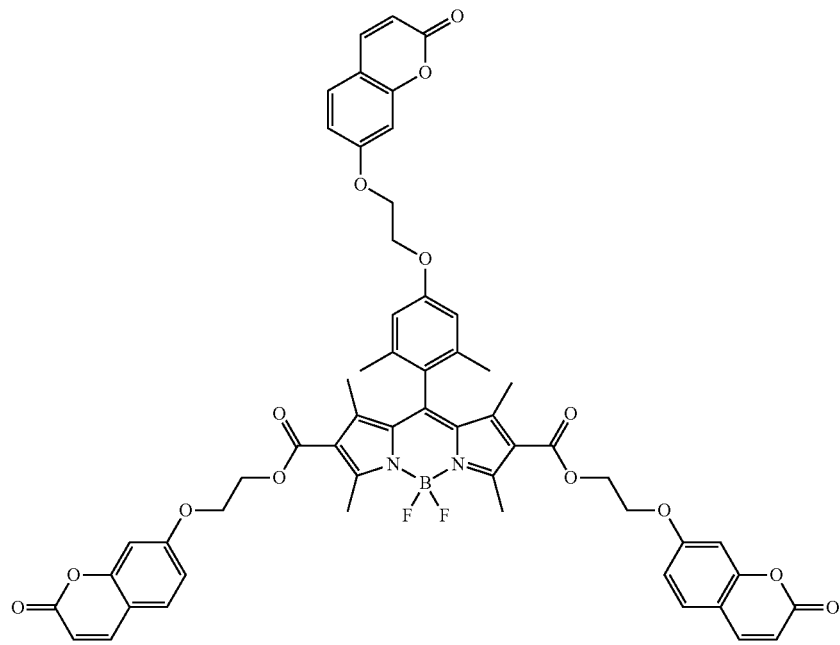
compound 1-54
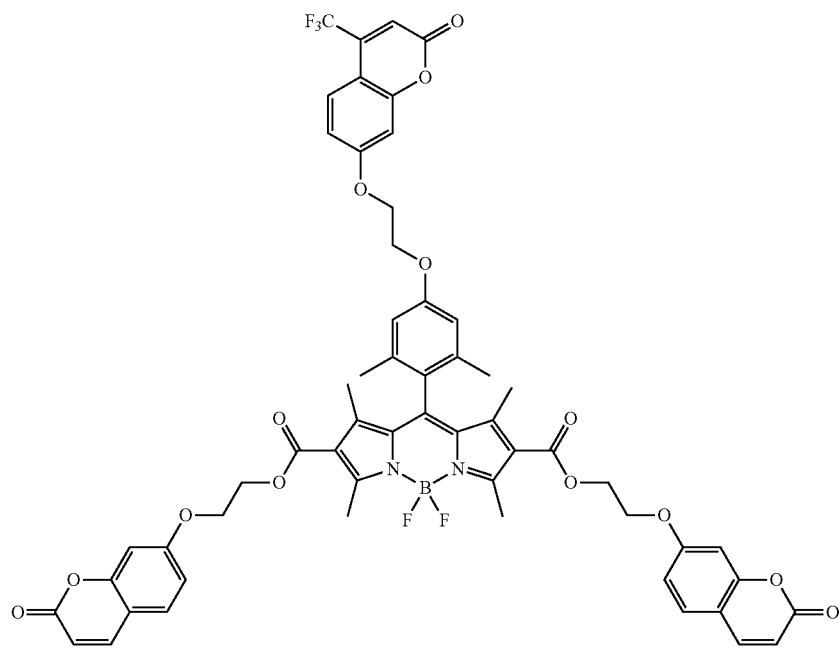

-continued
compound 1-55
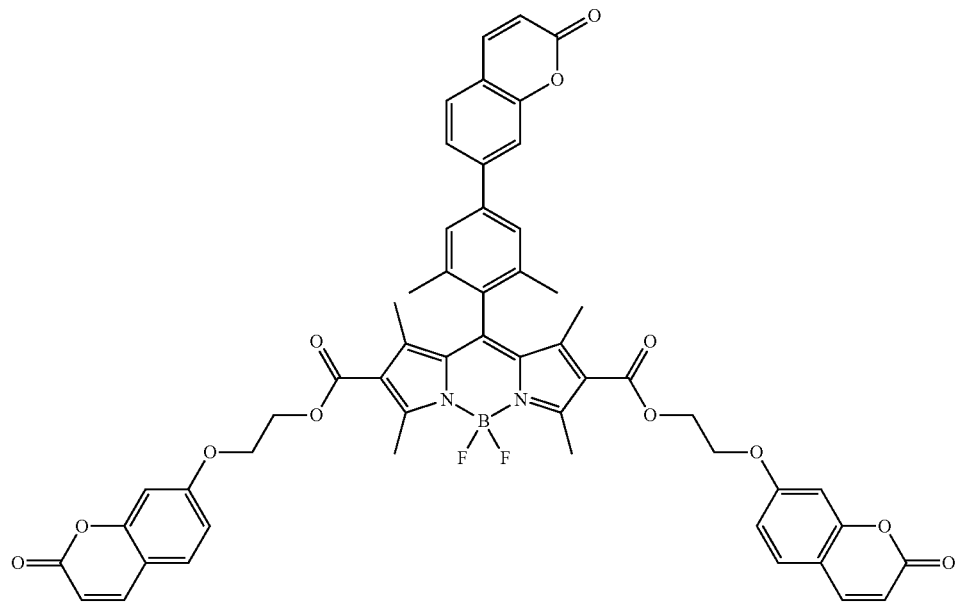
compound 1-56
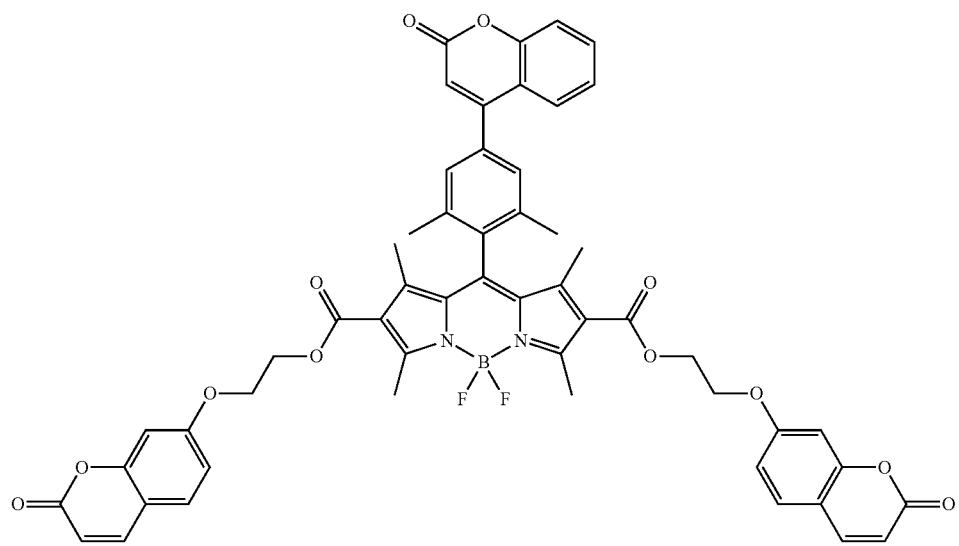

compound 1-57
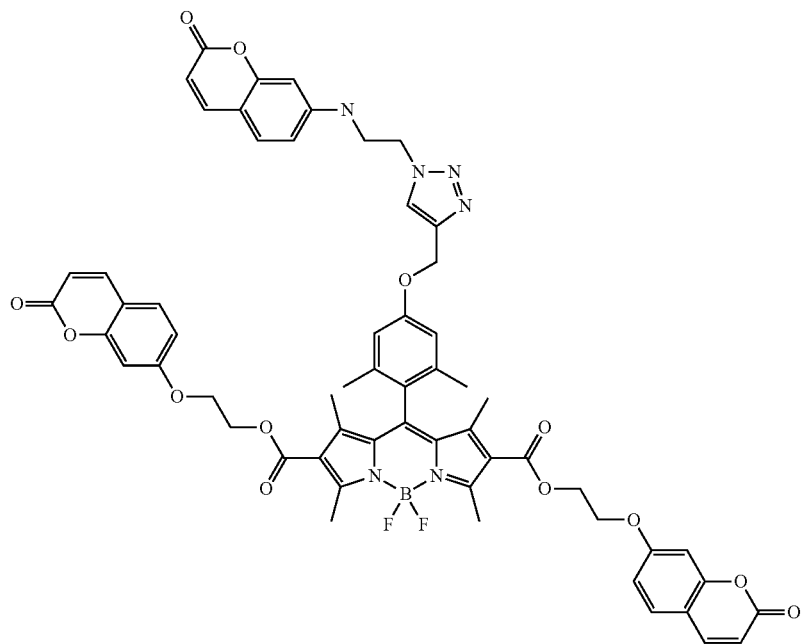
compound 1-58
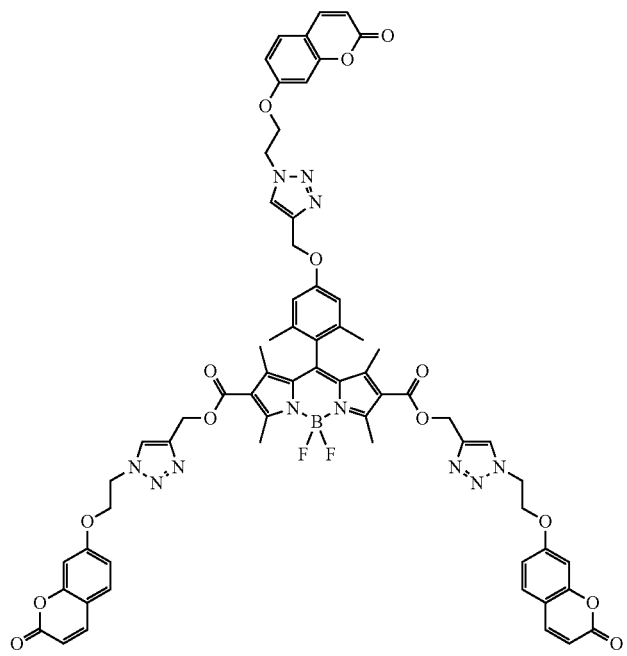

compound 1-59
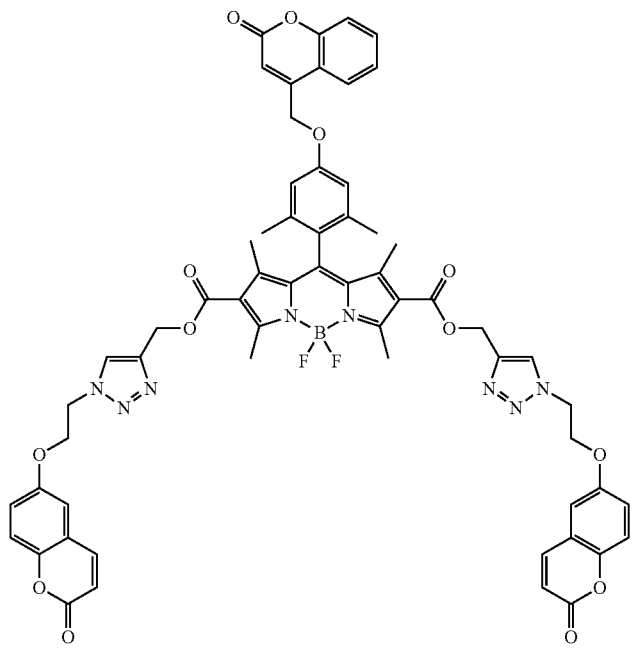
compound 1-60
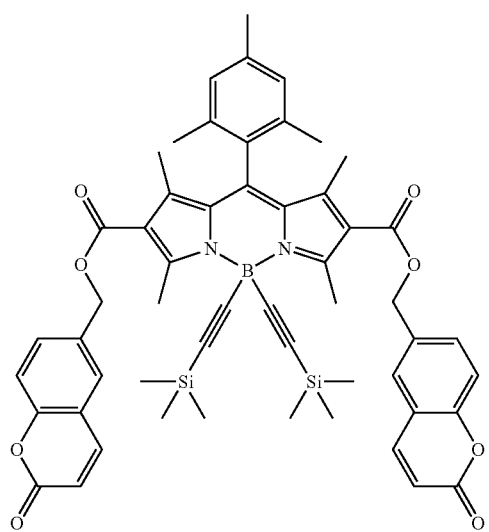
compound 1-61
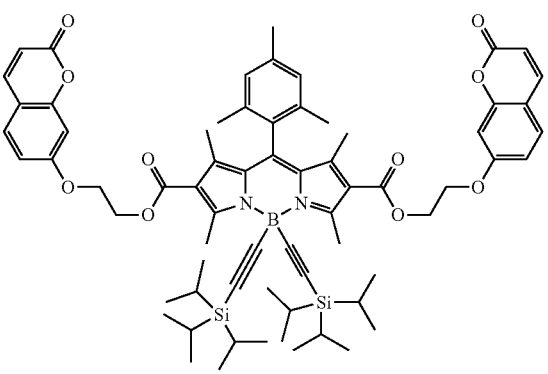
compound 1-62
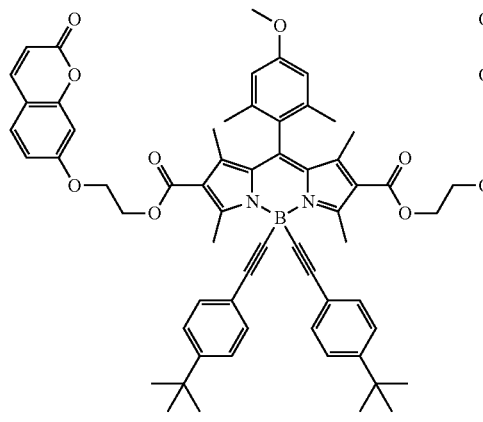
compound 1-63
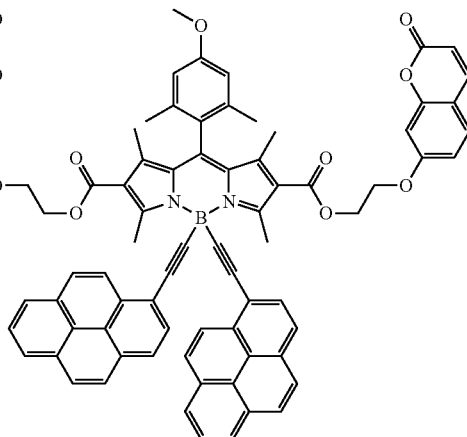

compound 1-64
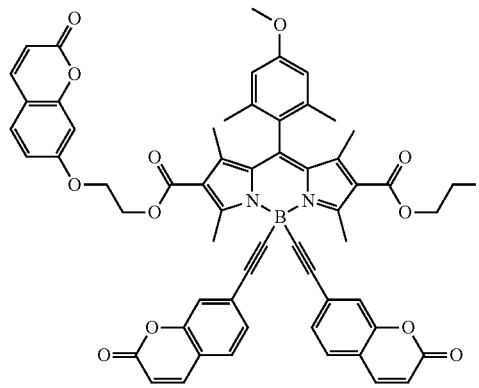
compound 1-65
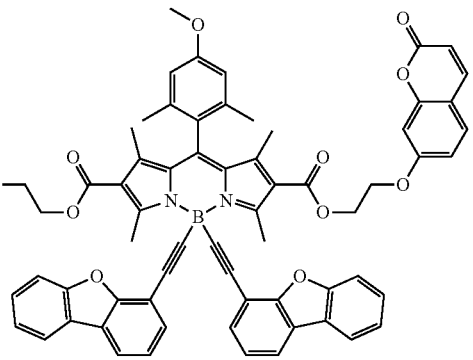
compound 1-66
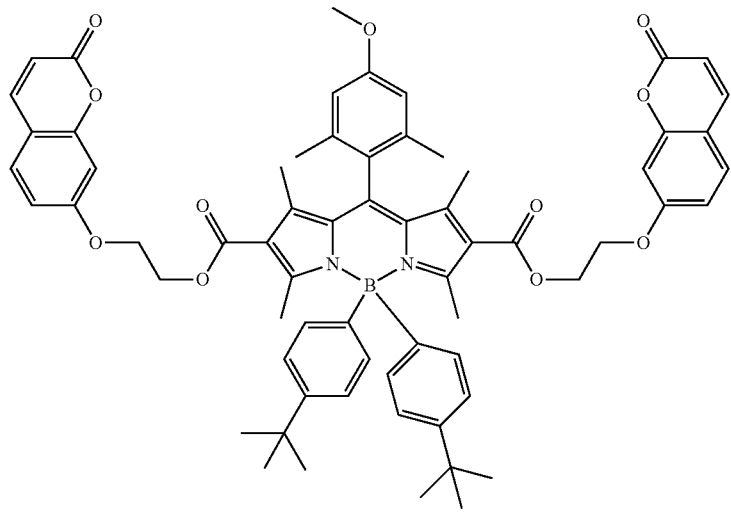
compound 1-67
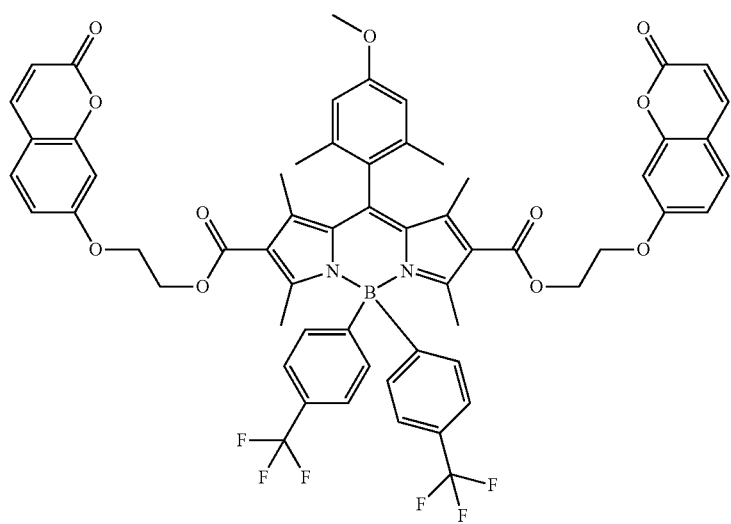

-continued
compound 1-68
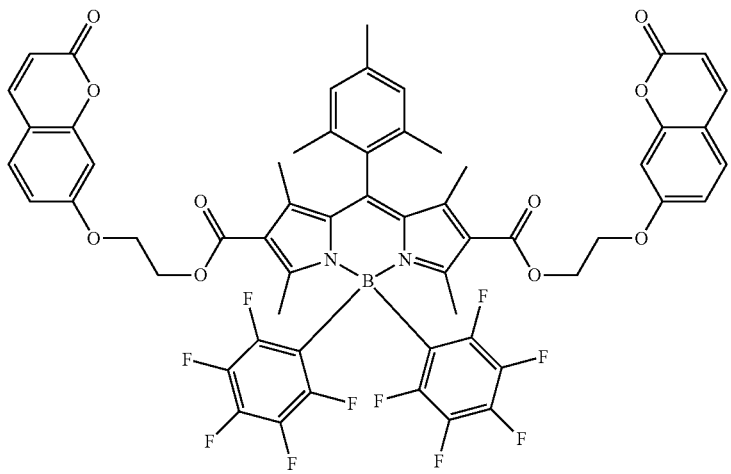
compound 1-69
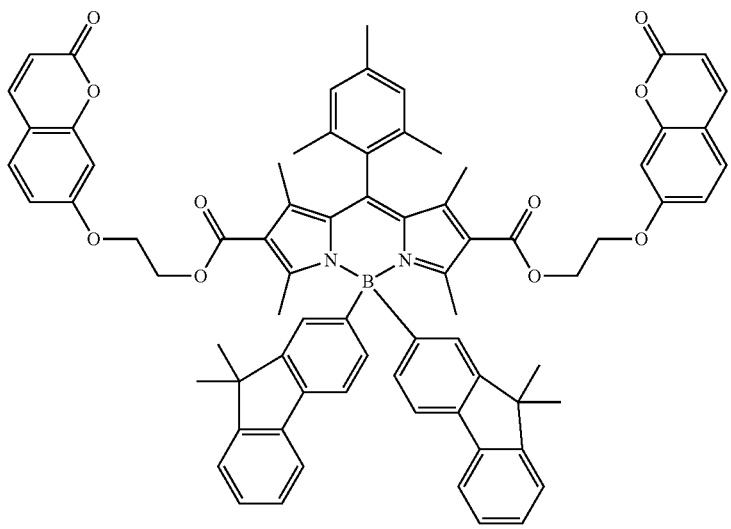
compound 1-70
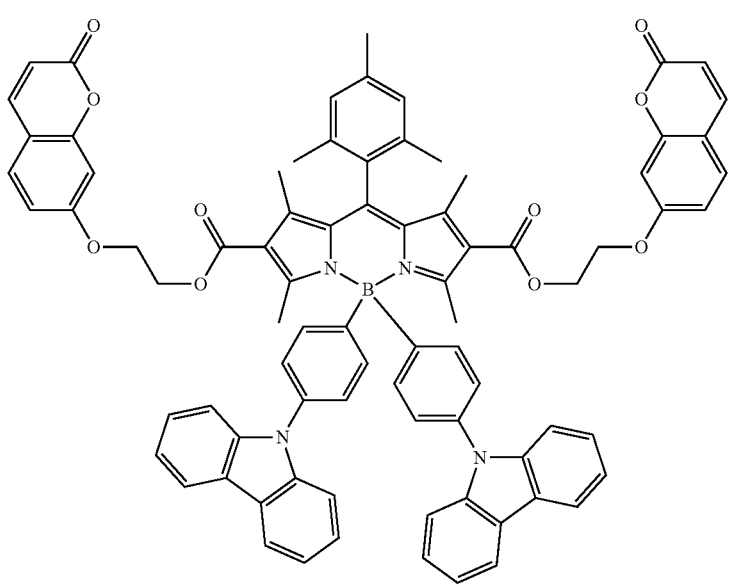

compound 1-71
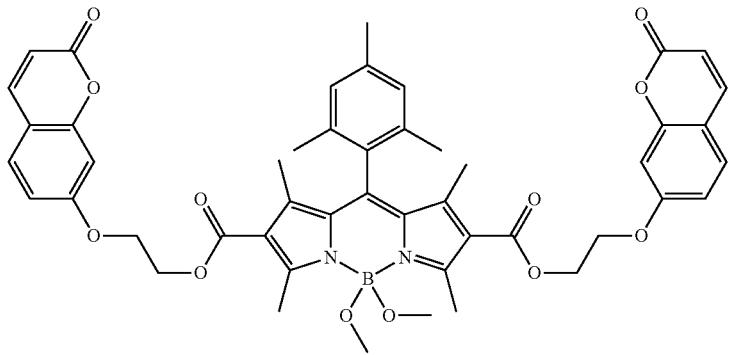
compound 1-72
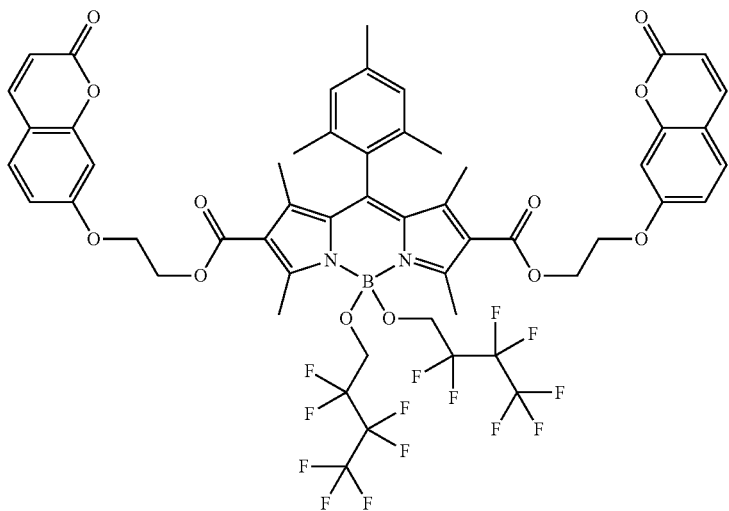
compound 1-73
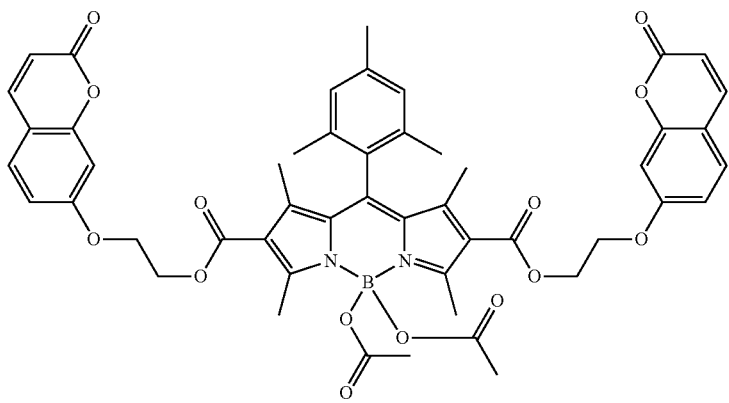

compound 1-74
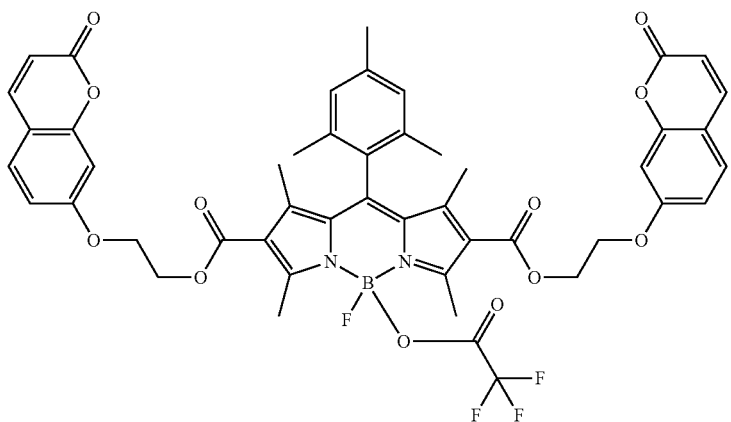
compound 1-75
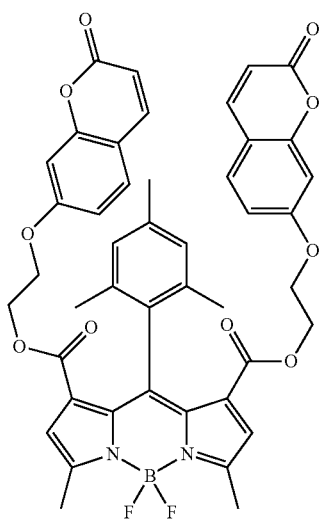
compound 1-76
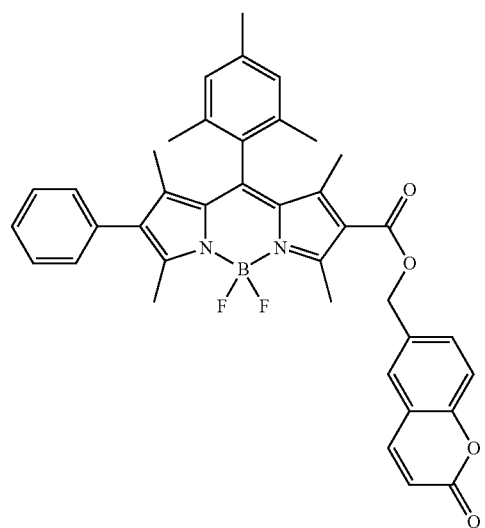
compound 1-77
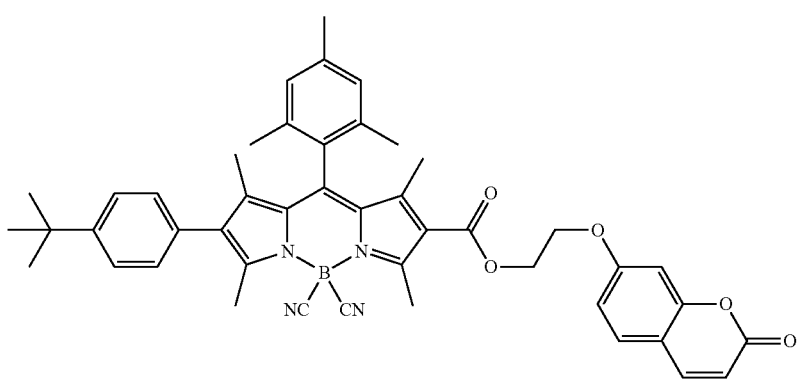

-continued
compound 1-78
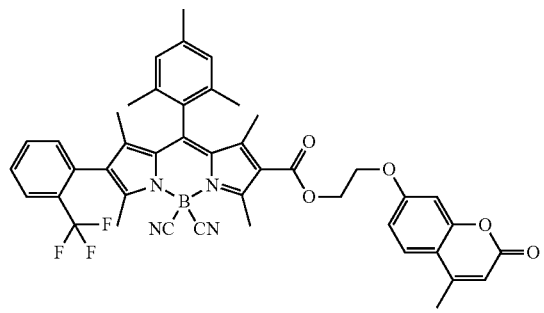
compound 1-79
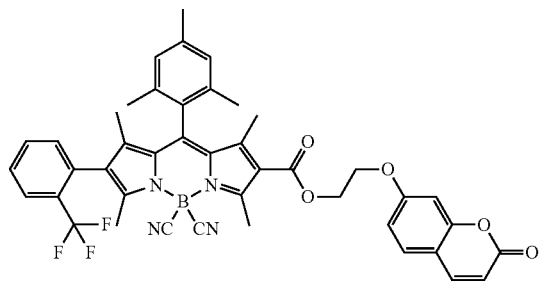
compound 1-80
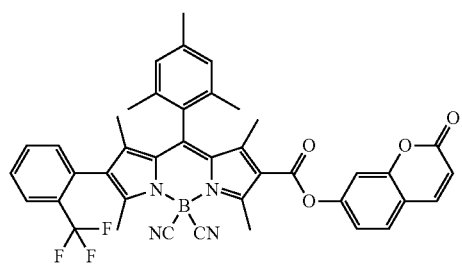
compound 1-81
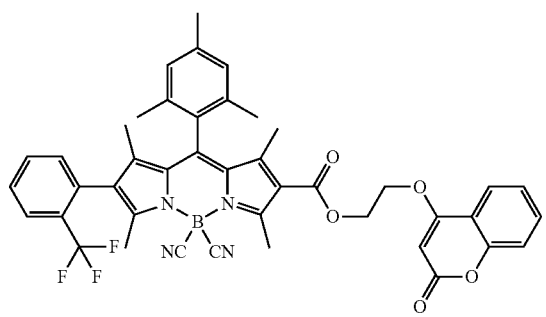
compound 1-82
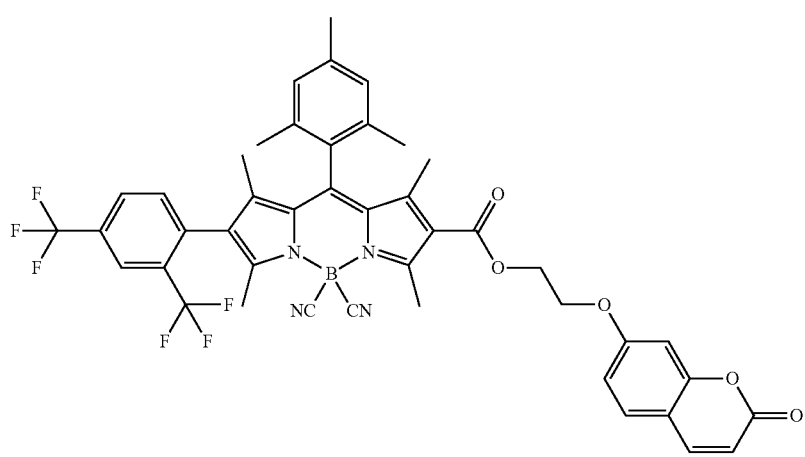
compound 1-83
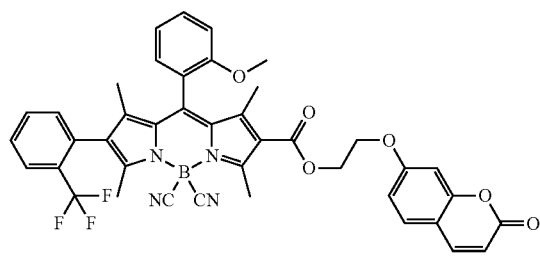
compound 1-84
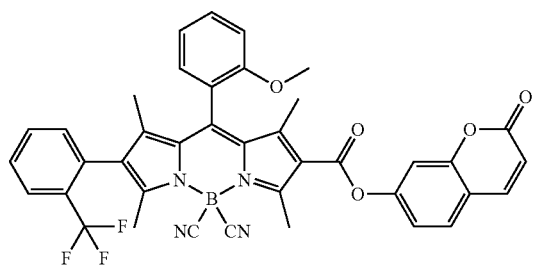

compound 1-85
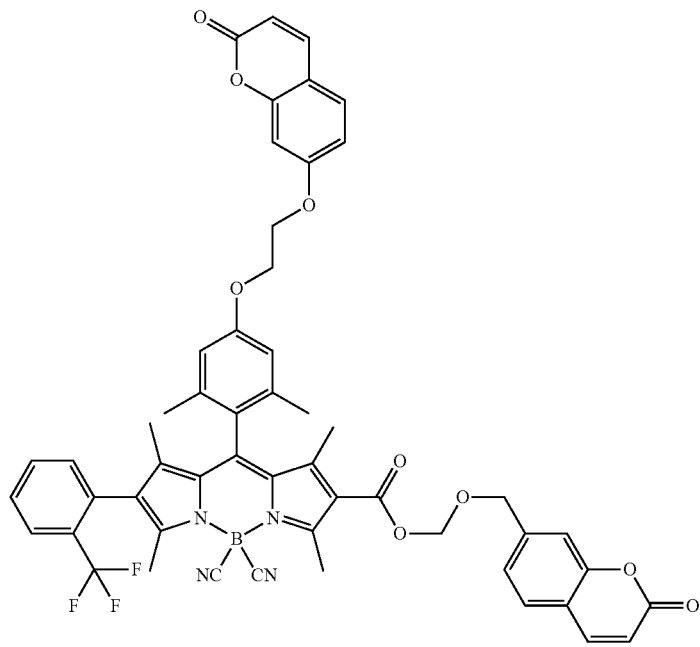
compound 1-86
compound 1-87
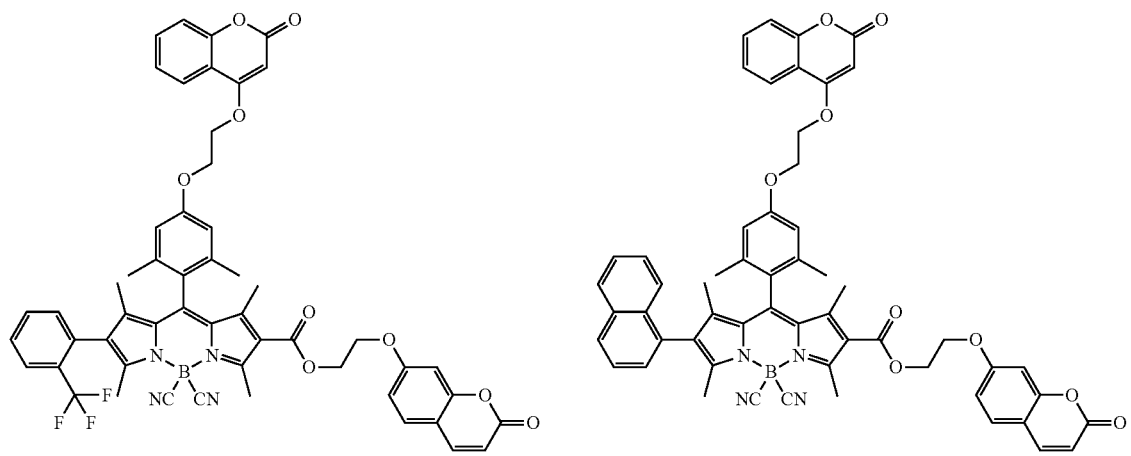
compound 1-88
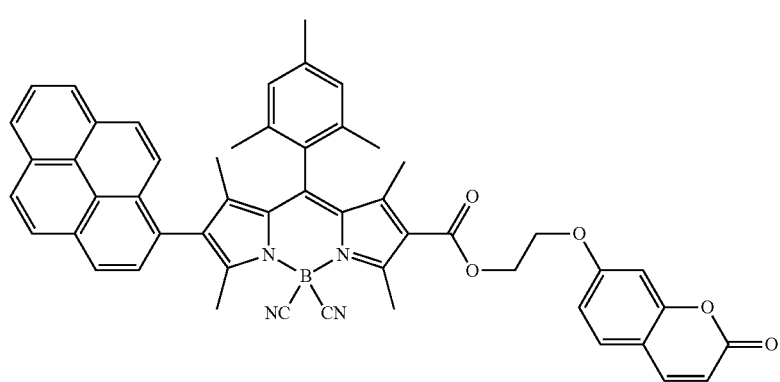

compound 1-89
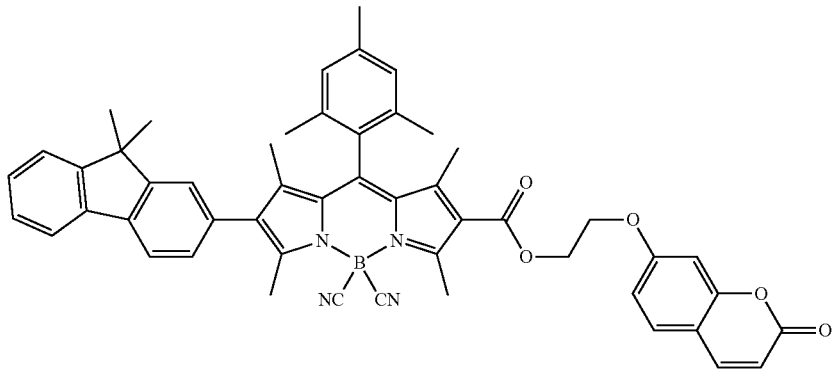
compound 1-90
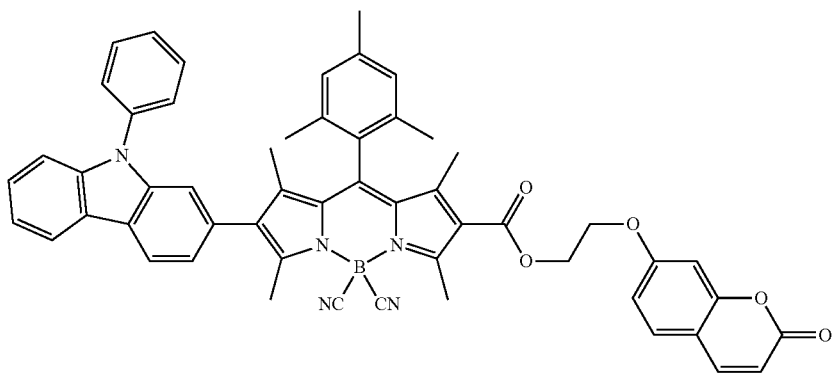
compound 1-91
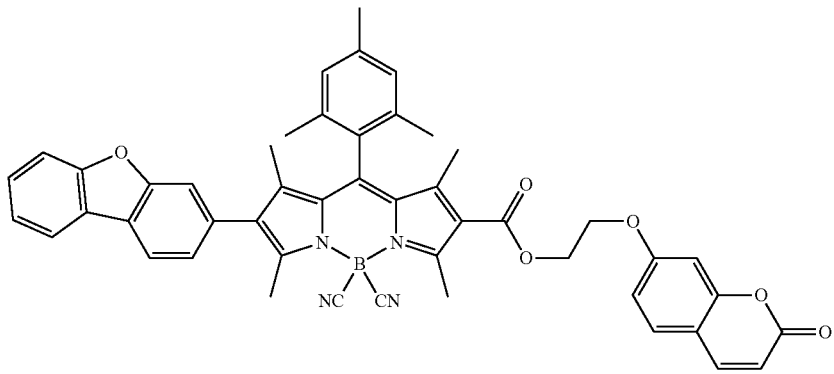
compound 1-92
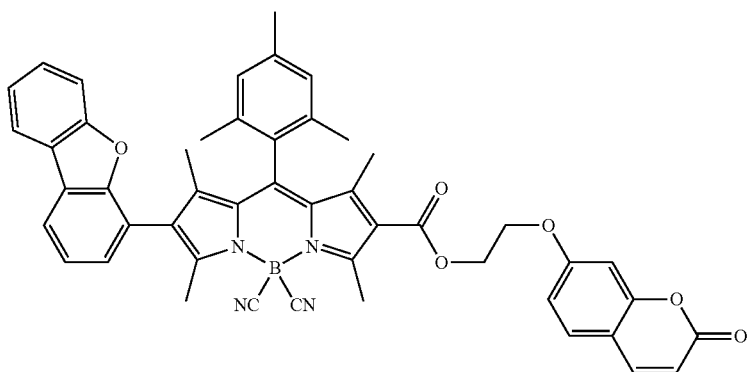

-continued
compound 1-93
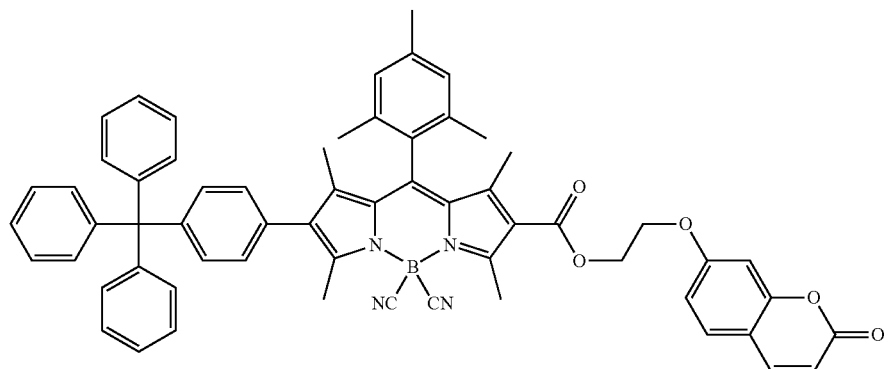
compound 1-94
compound 1-95
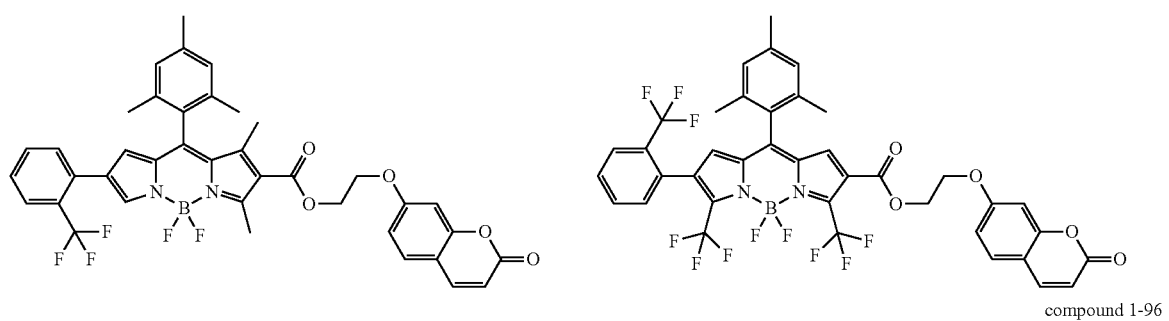
compound 1-96
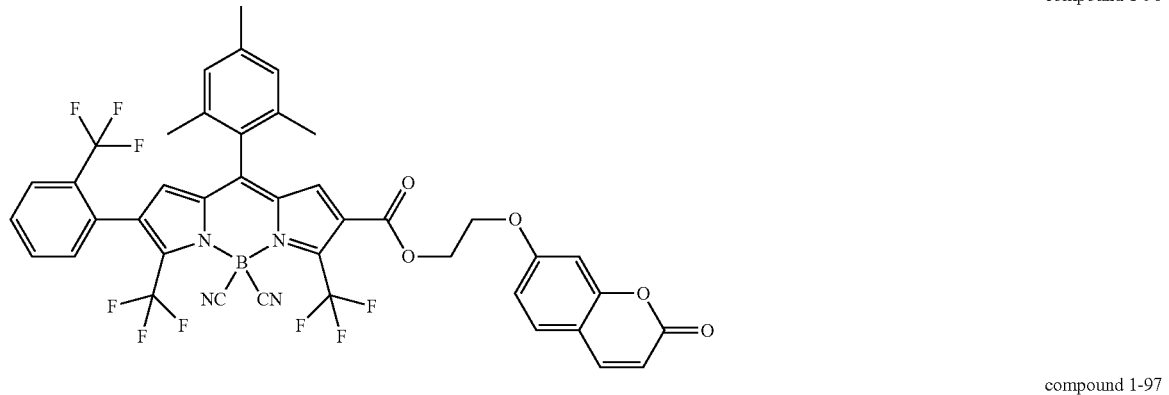
compound 1-97
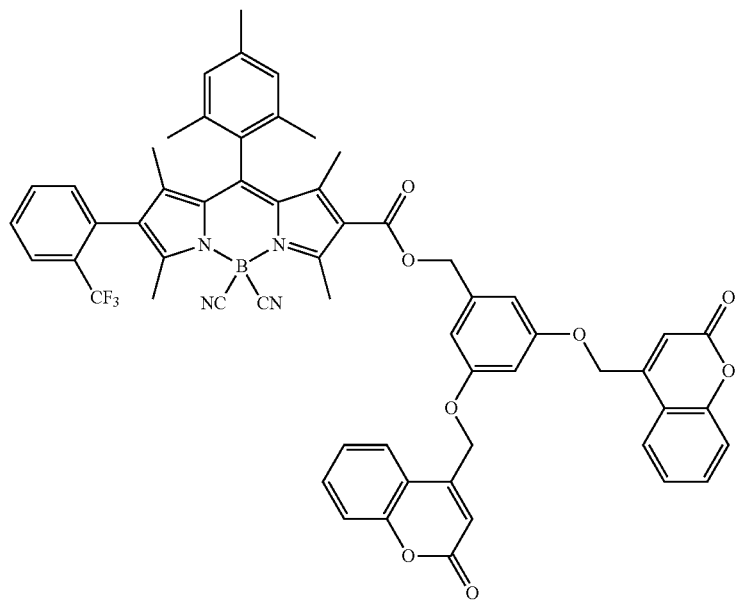

-continued
compound 1-98
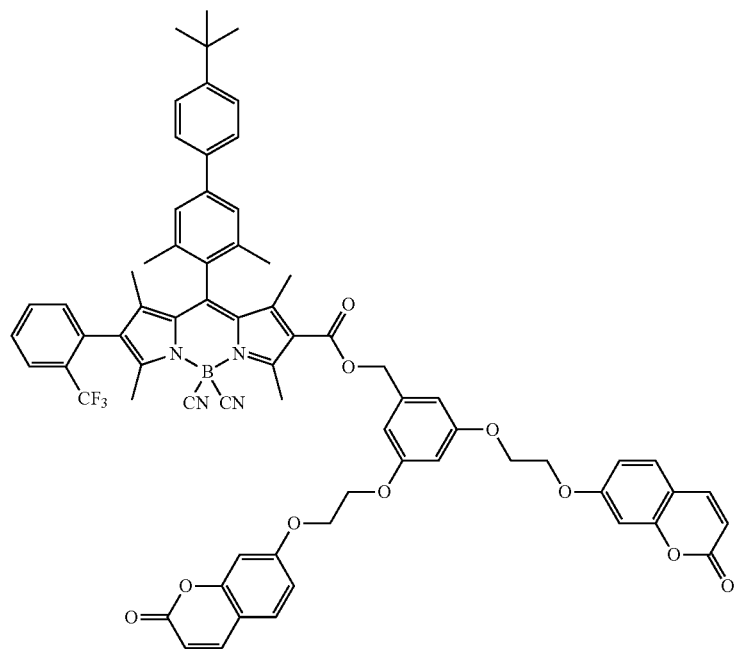
compound 1-99
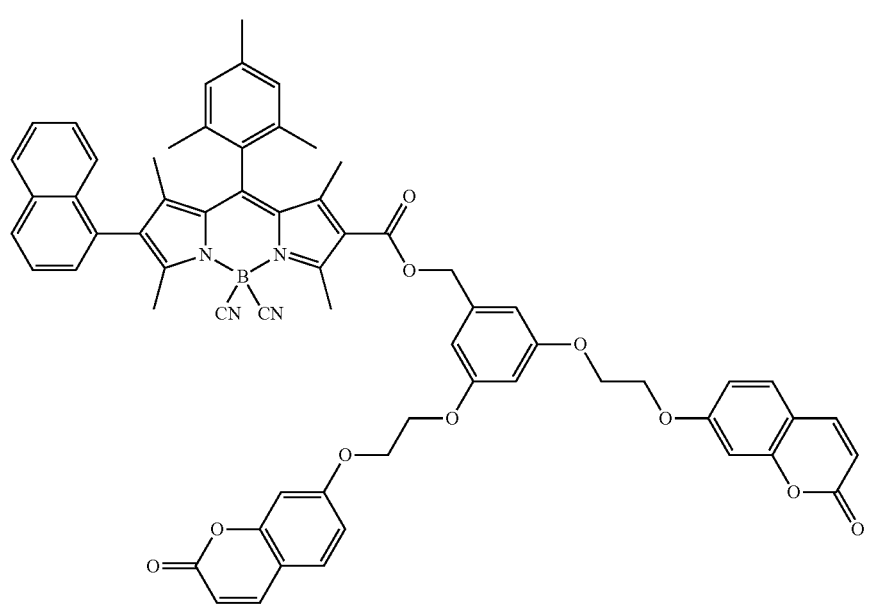

compound 1-100
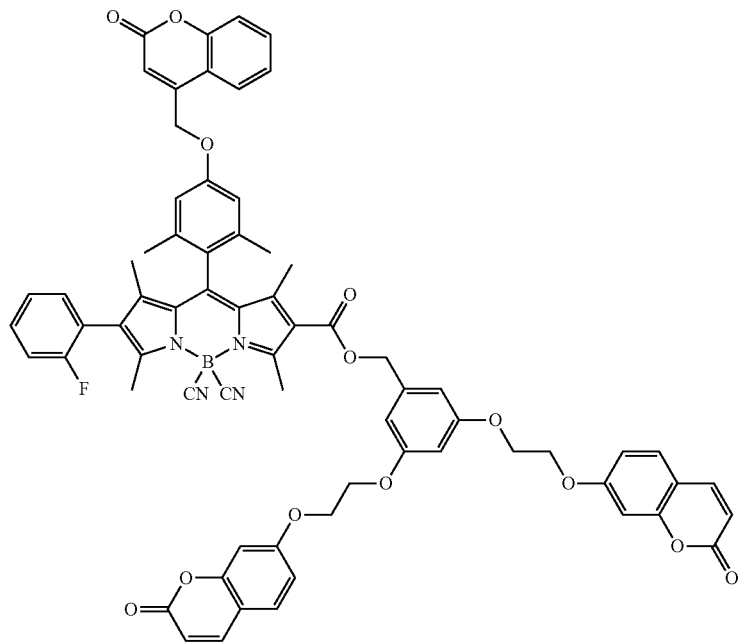
compound 1-101
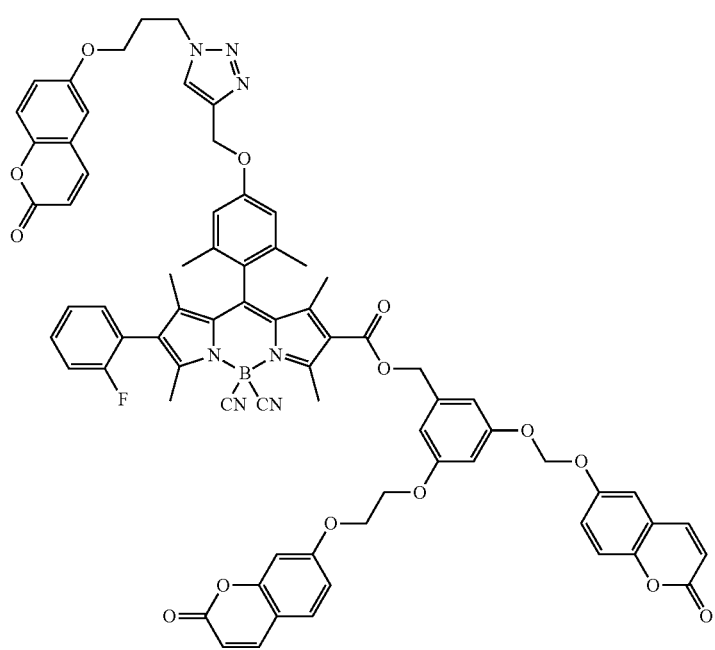

compound 1-102
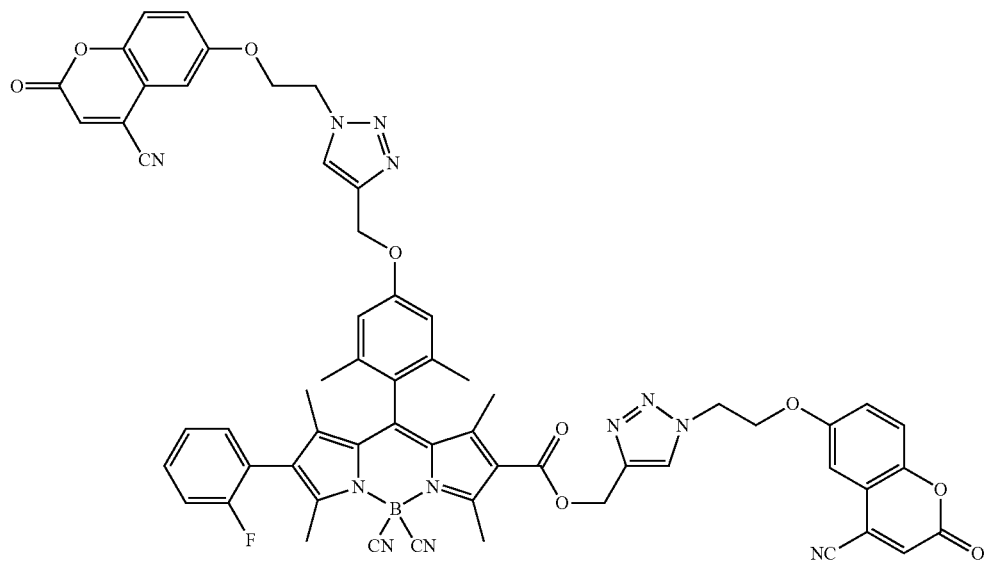
compound 1-103
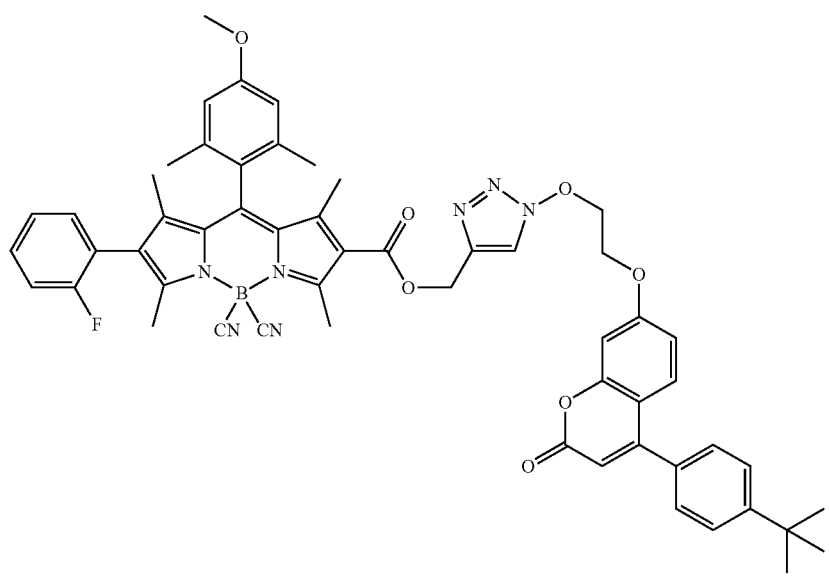
compound 1-104
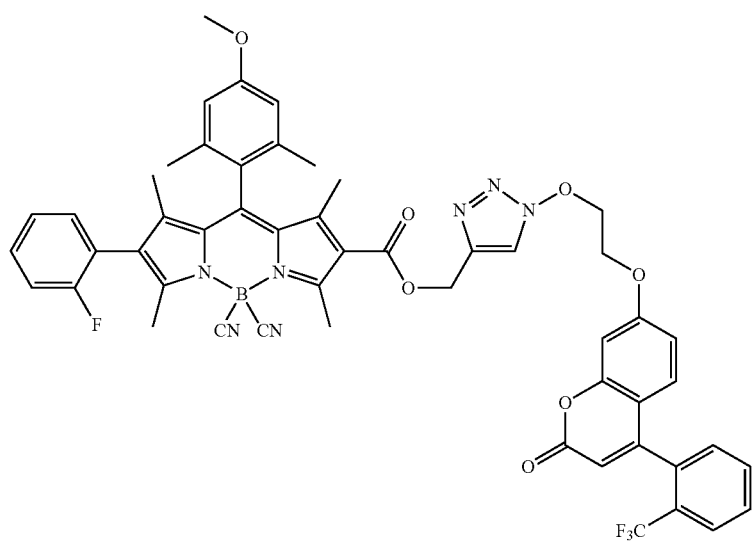

-continued
compound 1-105
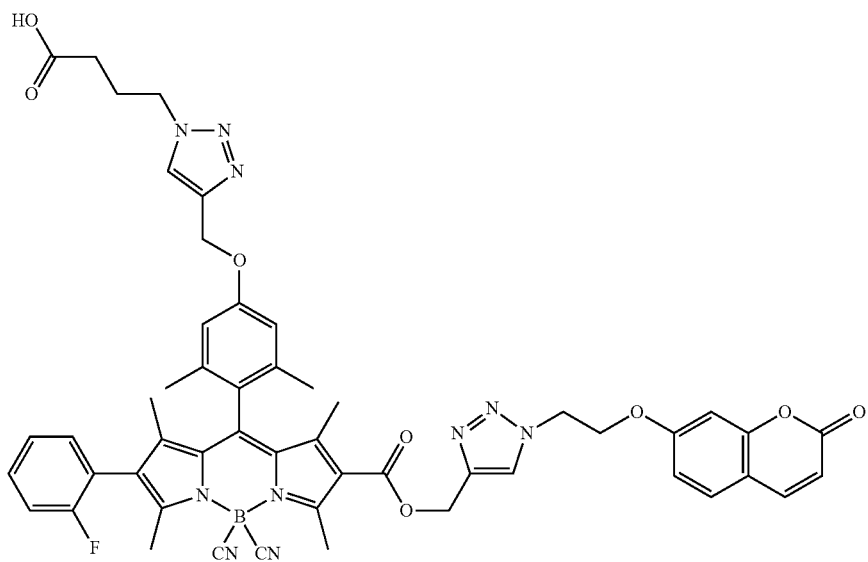
compound 1-106
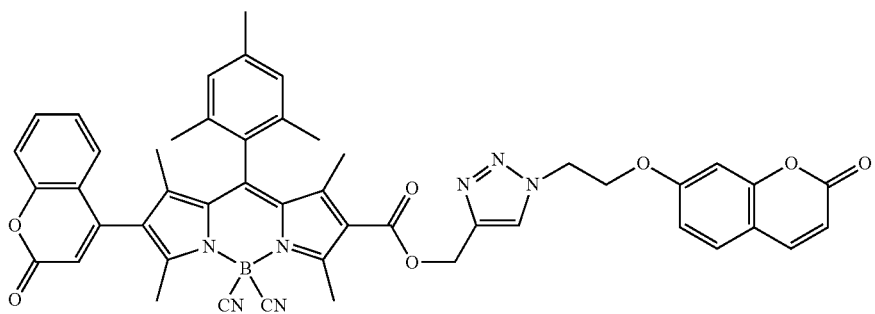
compound 1-107
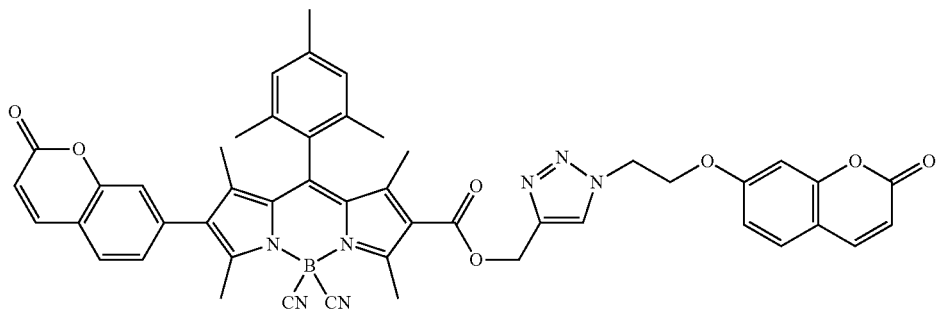
compound 1-108
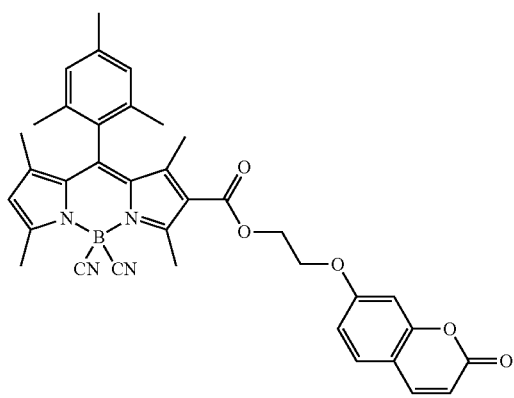
compound 1-109
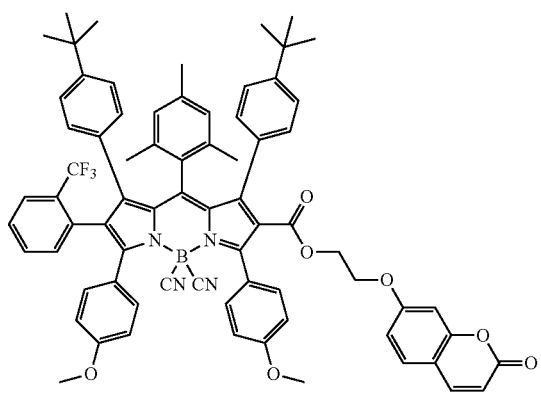

compound 1-110    compound 1-111
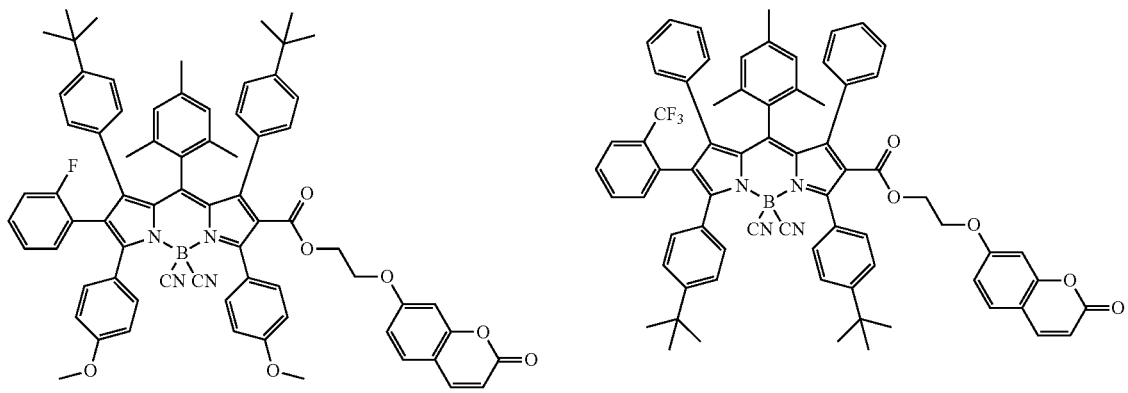
According to one embodiment of the present specification, the core of the compound represented by Chemical Formula 1 may be prepared using general preparation methods of General Formulae 1 and 2 as follows, but the method is not limited thereto.
[General Formula 1]
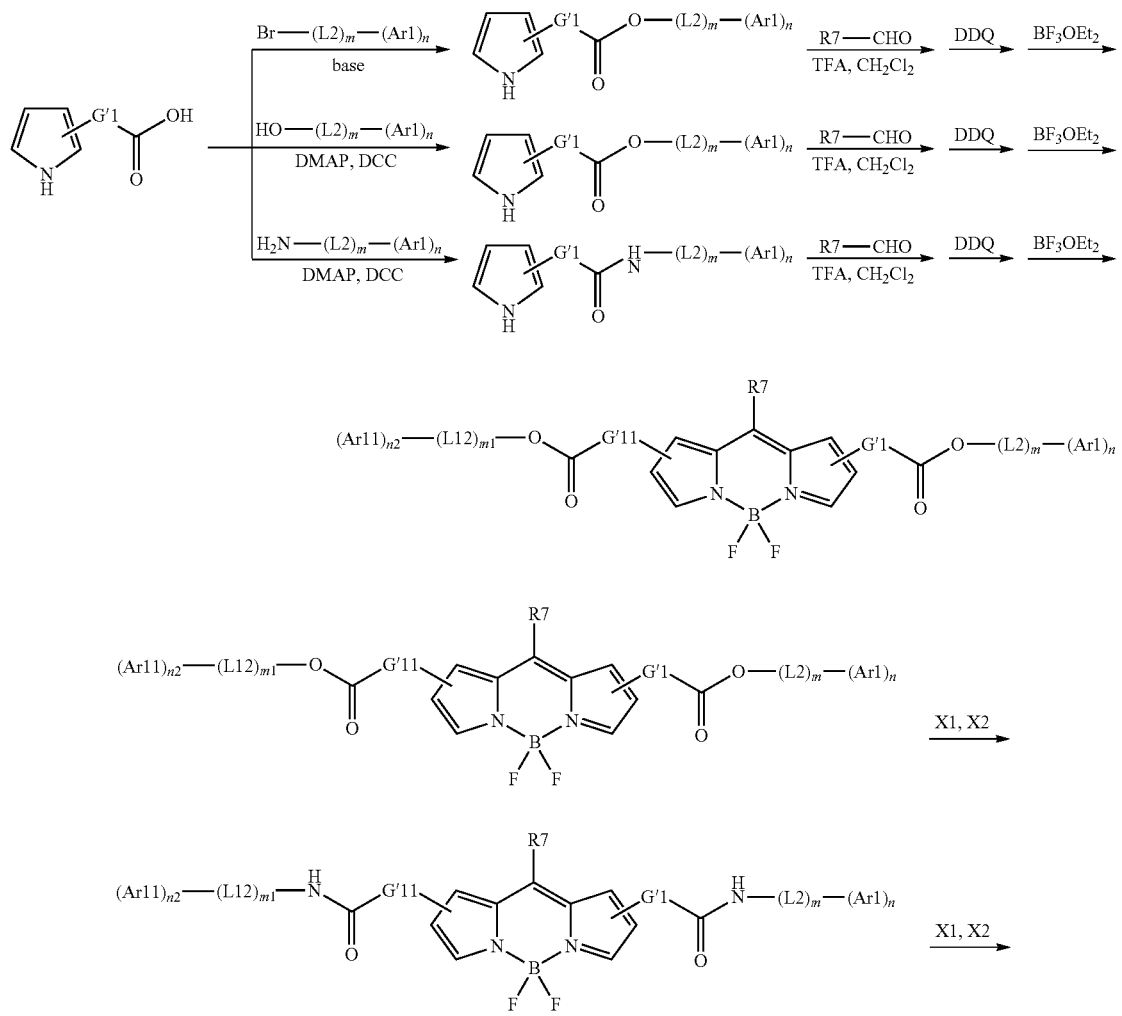

-continued

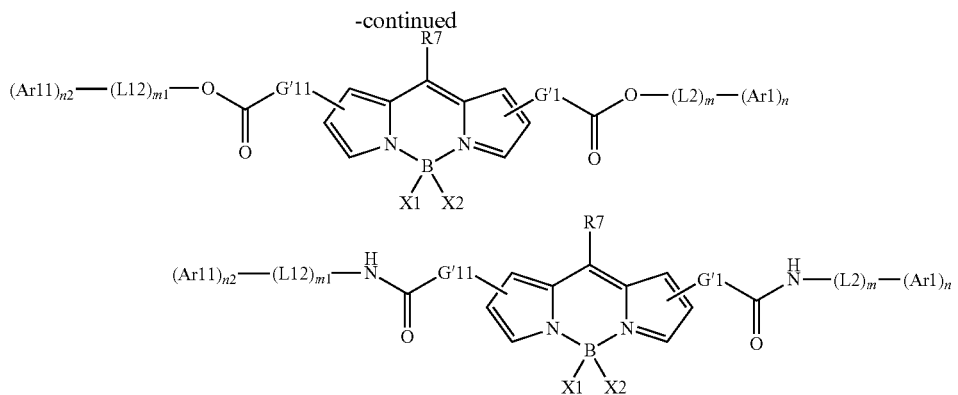

In General Formula 1, G'1 and G'11 have the same definitions as G1 described above, and R7, L2, Ar1, L12, Ar11, n, n1, m, m1, X1 and X2 has the same definitions as described above. For example, in a structure linking a coumarine group to both sides of the boron-dipyrromethene (BODIPY) through an ester or amide bond in General Formula 1, the structure may be prepared by introducing a coumarine group to pyrrole having a carboxyl group through an ester or amide bond, and then forming a boron-dipyrromethene(BODIPY) skeleton. The result may be additionally substituted with a fluoro group of boron.

[General Formula 2]

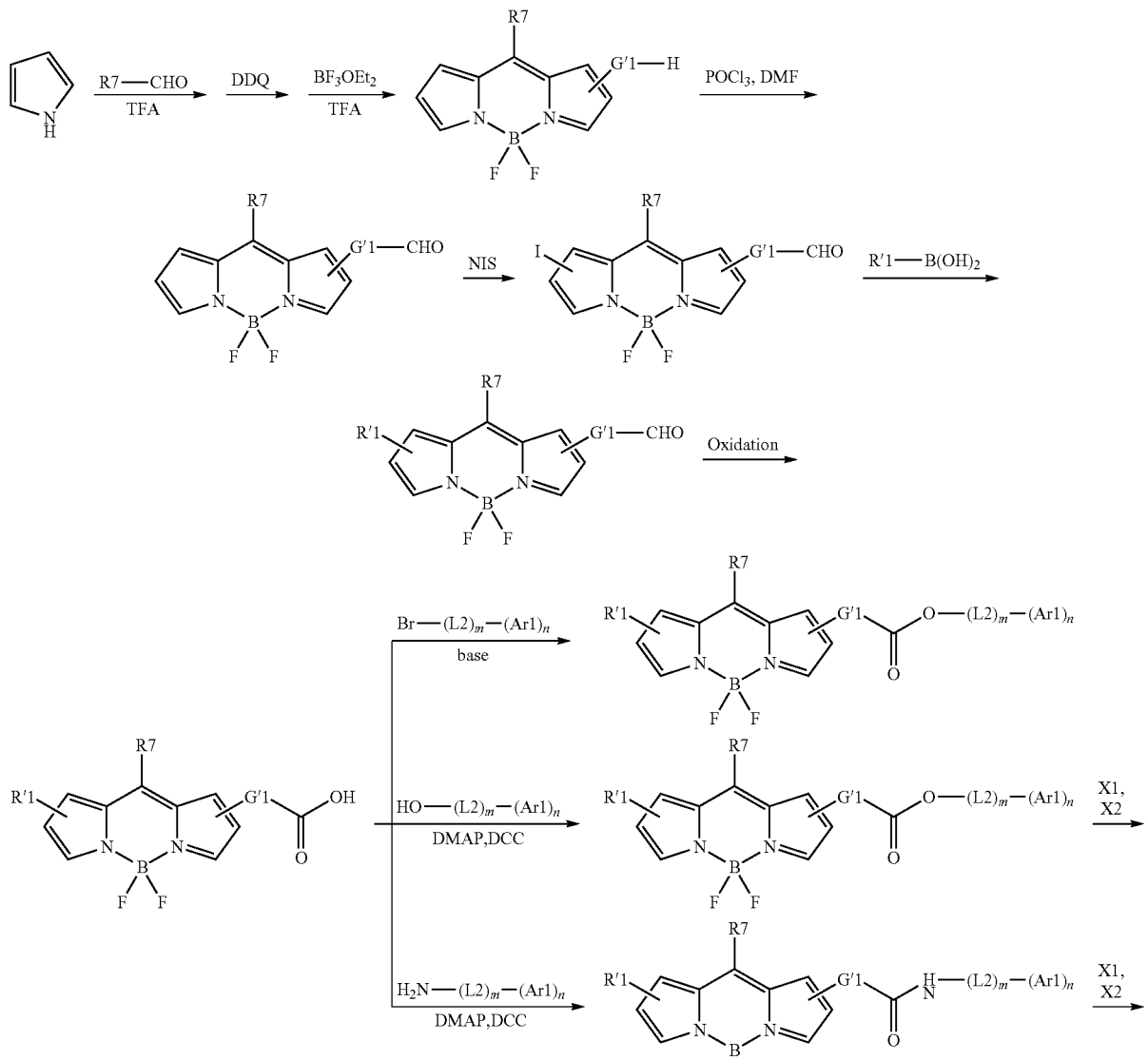

-continued

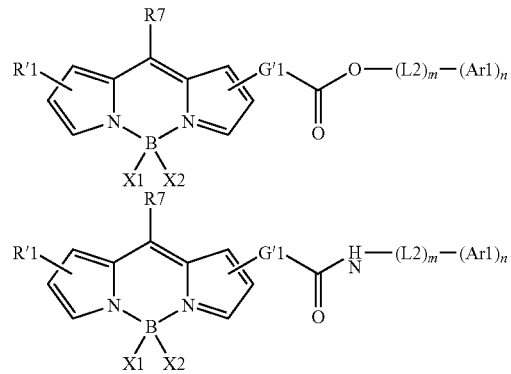

In General Formula 2, G'1 has the same definition as G1, R'1 has the same definition as R1 described above, and R7, L2, Ar1, n, m, X1 and X2 have the same definition as described above. For example, in an asymmetric structure in General Formula 2, a boron-dipyrromethene(BODIPY) skeleton is formed pyrrole and aldehyde, and then aldehyde is introduced, and halogen is introduced using N-Iodosuccinimide(NIS). Aryl and heteroaryl groups are introduced through Suzuki coupling, and then the result is oxidized to make carboxylic acid. After introducing a coumarine derivative through ester and amide bonds, the fluoro group of boron is substituted with other functional groups as necessary.

One embodiment of the present specification provides a color conversion film including a resin matrix; and the compound represented by Chemical Formula 1 dispersed into the resin matrix.

The content of the compound represented by Chemical Formula 1 in the color conversion film may be in a range of 0.001% by weight to 10% by weight.

The color conversion film may include one type of the compound represented by Chemical Formula 1, or may include two or more types thereof. For example, the color conversion film may include one type of compound emitting green light among the compounds represented by Chemical Formula 1. As another example, the color conversion film may include one type of compound emitting red light among the compounds represented by Chemical Formula 1. As still another example, the color conversion film may include one type of compound emitting green light and one type of compound emitting red light among the compounds represented by Chemical Formula 1.

The color conversion film may further include additional fluorescent substances in addition to the compound represented by Chemical Formula 1. When using a light source emitting blue light, the color conversion film preferably includes both a green light emitting fluorescent substance and a red light emitting fluorescent substance. In addition, when using a light source emitting blue light and green light, the color conversion film may only include a red light emitting fluorescent substance. However, the color conversion film is not limited thereto, and even when using a light source emitting blue light, the color conversion film may only include a red light emitting compound when a separate film including a green light emitting fluorescent substance is laminated. On the other hand, even when using a light source emitting blue light, the color conversion film may only include a green light emitting compound when a separate film including a red light emitting fluorescent substance is laminated.

According to one embodiment of the present specification, the color conversion film has a haze value of 50% to 95%, and preferably 65% to 85%. When the color conversion film has a haze value in the above-mentioned range, color conversion efficiency of the color conversion film may be enhanced.

According to one embodiment of the present specification, the color conversion film further includes one or more fine particles formed with one or more of organic substances and inorganic substances.

The fine particles are covered with materials suppressing the quenching of the compound represented by Chemical Formula 1.

The inorganic fine particles include inorganic oxides, inorganic nitrides or inorganic acid nitrides. Specifically, the fine particles may be one or more selected from the group consisting of $SiO_x$, $SiN_x$, $SiO_xN_y$, $AlO_x$, $TiO_x$, $TaO_x$, $ZnO_x$, $ZrO_x$, $CeO_x$ and $ZrSiO_x$ (in the formulae, x is from 0.1 to 2, and y is from 0.5 to 1.3), and among these, $TiO_x$, $ZnO_x$, $ZrO_x$ and $CeO_x$ are preferable.

On the surface of the fine particles, a covering layer suppressing the quenching of the compound represented by Chemical Formula 1 may be formed. Examples of the covering layer suppressing the quenching of fluorescent substances may include those preventing destruction of coloring or binder resins caused by fine particles having a photocatalysis function, or those insulating fine particles having semiconductor properties. Examples of materials forming such a covering layer include alumina, zirconia, silica, zirconia silicate, alumina silicate, borosilicate glass and the like.

In addition, the fine particles may be a hollow body. When using hollow fine particles, a refractive index between the air (hollow portion) and the resin matrix is large (with respect to 1.0, a refractive index of the air, the resin matrix has 1.5 to 1.6), and light scattering effect is large. In addition, it is preferable since oxygen in the air sometimes suppresses deterioration of the compound represented by Chemical Formula 1.

Among the fine particles, fine particles having a high refractive index or fine particles having a low refractive index, and specifically, fine particles having a refractive index of 2.0 to 2.8 or 1.0 to 1.2 are preferable. Using such fine particles may lengthen a light path of light coming from a light source in the color conversion film, and the color conversion film may efficiently absorb light coming from the light source. In addition, the color conversion film may scatter converted light and enhance extraction efficiency. Accordingly, conversion efficiency of the color conversion film may be enhanced. Examples of such fine particles may include $TiO_2$ fine particles (refractive index=2.7), ZnO (refractive index=2.0), $CeO_2$ (refractive index=2.4), $ZrO_2$ (refractive index=2.2), hollow silica, hollow glass and the like.

A first average particle diameter of the fine particles is not particularly limited as long as the haze value is in the above-mentioned range, but may be from 1 nm to 500 nm, is preferably greater than or equal to 1 nm and less than 100 nm, and is particularly preferably greater than or equal to 5 nm and less than 80 nm. The particle diameter being 500 nm or greater may cause concerns such that the fine particles may not be uniformly dispersed into the color conversion film, uniform light emission may not be obtained, or highly fine patterning using photolitho and the like may not be achieved. The particle diameter being less than 1 nm may cause concerns such that sufficient light scattering is not obtained. Meanwhile, the fine particles may aggregate and sometimes have diameters of 100 nm or greater in the color conversion film, however, there are no problems as long as the first average particle diameter is greater than or equal to 1 nm and less than 100 nm.

In addition, the added amount of the fine particles in the color conversion film is not particularly limited as long as the haze value is in the above-mentioned range, but is normally preferably from 1% by weight to 75% by weight with respect to the total weight of the color conversion film, and particularly preferably greater than or equal to 10% by weight and less than or equal to 50% by weight. Adding in less than 1% by weight may cause concerns such that sufficient light scattering may not occur, and adding in greater than 75% by weight may cause concerns such that the color conversion film is mechanically embrittled.

Meanwhile, the fine particles of organic substances or inorganic substances may be used either alone as one type, or as a mixture of two or more types.

The color conversion film may further include a resin matrix; and an additional layer including a compound dispersed into the resin matrix and emitting light in a wavelength different from the wavelength of the compound represented by Chemical Formula 1. The compound emitting light in a wavelength different from the wavelength of the compound represented by Chemical Formula 1 may also be the compound represented by Chemical Formula 1, or may be other known fluorescent materials.

The resin matrix material is preferably a theuttoplastic polymer or a themocurable polymer. Specifically, a poly (meth)acryl-based such as polymethyl methacrylate (PMMA), a polycarbonate (PC)-based, a polystyrene (PS)-based, a polyarylene (PAR)-based, a polyurethane (TPU)-based, a styrene-acrylonitrile (SAN)-based, a polyvinylidene fluoride (PVDF)-based, a modified polyvinylidene fluoride (modified-PVDF)-based and the like may be used as the resin matrix material.

According to one embodiment of the present specification, the color conversion film according to the embodiments described above additionally includes light diffusing particles. By dispersing light diffusing particles instead of a light diffusing film used in the art into the color conversion film for enhancing luminance, higher luminance may be exhibited compared to using a separate light diffusing film, and an adhering process may be skipped as well.

As the light diffusing particles, particles having a high refractive index with a resin matrix may be used, and examples thereof may include $TiO_2$, silica, borosilicate, alumina, sapphire, air or other gases, air- or gas-filled hollow beads or particles (for example, air/gas-filled glass or polymers); polystyrene, polycarbonate, polymethyl methacrylate, acryl, methyl methacrylate, styrene, melamine resin, formaldehyde resin, or polymer particles including melamine and formaldehyde resins, or any suitable combination thereof.

The light diffusing particles may have particle diameters in a range of 0.1 μm to 5 μm, for example, in a range of 0.3 μm to 1 μm. The content of the light diffusing particles may be determined as necessary, and for example, may be in a range of approximately 1 part by weight to 30 parts by weight based on 100 parts by weight of the resin matrix.

The color conversion film according to the embodiments described above may have a thickness of 2 μm to 200 μm. Particularly, the color conversion film may exhibit high luminance even with a small thickness of 2 micrometers to 20 micrometers. This is due to the fact that the content of the fluorescent substance molecules included in the unit volume is higher compared to quantum dots.

The color conversion film according to the embodiments described above may have a substrate provided on one surface. This substrate may function as a support when preparing the color conversion film. Types of the substrate are not particularly limited, and the material or thickness is not limited as long as it is transparent and is capable of functioning as the support. Herein, transparency means having visible light transmittance of 70% or higher. For example, a PET film may be used as the substrate.

The color conversion film described above may be prepared by coating a resin solution in which the compound represented by Chemical Formula 1 described above is dissolved on a substrate and drying the result, or by extruding and filming the compound represented by Chemical Formula 1 described above together with a resin.

The compound represented by Chemical Formula 1 is dissolved in the resin solution, and therefore, the compound represented by Chemical Formula 1 is uniformly distributed in the solution. This is different from a quantum dot film preparation process that requires a separate dispersion process.

As for the resin solution in which the compound represented by Chemical Formula 1 is dissolved, the preparation method is not particularly limited as long as the compound represented by Chemical Formula 1 and the resin described above are dissolved in the solution.

According to one example, the resin solution in which the compound represented by Chemical Formula 1 is dissolved may be prepared using a method of preparing a first solution by dissolving the compound represented by Chemical Formula 1 in a solvent, preparing a second solution by dissolving a resin in a solvent, and mixing the first solution and the second solution. When mixing the first solution and the second solution, it is preferable that these be uniformly mixed. However, the method is not limited thereto, and a method of simultaneously adding and dissolving the compound represented by Chemical Formula 1 and a resin in a solvent, a method of dissolving the compound represented by Chemical Formula 1 in a solvent and subsequently adding and dissolving a resin, a method of dissolving a resin in a solvent and then subsequently adding and dissolving the compound represented by Chemical Formula 1, and the like, may be used.

As the resin included in the solution, the resin matrix material described above, a monomer curable to this resin matrix resin, or a mixture thereof, may be used. For example, the monomer curable to the resin matrix resin includes a (meth)acryl-based monomer, and this may be formed to a resin matrix material by UV curing. When using such a curable monomer, an initiator required for curing may be further added as necessary.

The solvent is not particularly limited as long as it is capable of being removed by drying afterword while having no adverse effects on the coating process. Non-limiting examples of the solvent may include toluene, xylene, acetone, chloroform, various alcohol-based solvents, methylethyl ketone (MEK), methylisobutyl ketone (MIBK), ethyl acetate (EA), butyl acetate, dimethylformamide (DMF), dimethylacetamide (DMAc), dimethyl sulfoxide (DMSO), N-methyl-pyrrolidone (NMP) and the like, and one type or a mixture of two or more types may be used. When the first solution and the second solution are used, solvents included in each of the solutions may be the same as or different from each other. Even when different types of solvents are used in the first solution and the second solution, these solvents preferably has compatibility so as to be mixed with each other.

The process of coating the resin solution in which the compound represented by Chemical Formula 1 is dissolved on a substrate may use a roll-to-roll process. For example, a process of unwinding a substrate from a substrate-wound roll, coating the resin solution in which the compound represented by Chemical Formula 1 is dissolved on one surface of the substrate, drying the result, and then winding the result again on the roll may be used. When a roll-to-roll process is used, viscosity of the resin solution is preferably determined in a range capable of carrying out the process, and for example, may be determined in a range of 200 cps to 2,000 cps.

As the coating method, various known methods may be used, and for example, a die coater may be used, or various bar coating methods such as a comma coater and a reverse comma coater may be used.

After the coating, a drying process is carried out. The drying process may be carried out under a condition required to remove a solvent. For example, a color conversion film including a fluorescent substance including the compound represented by Chemical Formula 1 having target thickness and concentration may be obtained on a substrate by carrying out the drying in an oven located close to a coater under a condition to sufficiently evaporate a solvent, in a direction of the substrate progressing during the coating process.

When a monomer curable to the resin matrix resin is used as the resin included in the solution, curing, for example, UV curing, may be carried out prior to or at the same time as the drying.

When the compound represented by Chemical Formula 1 is filmed by being extruded with a resin, extrusion methods known in the art may be used, and for example, the color conversion film may be prepared by extruding the compound represented by Chemical Formula 1 with a resin such as a polycarbonate (PC)-based, a poly(meth)acryl-based and a styrene-acrylonitrile (SAN)-based.

According to one embodiment of the present specification, the color conversion film may have a protective film or a barrier film provided on at least one surface. As the protective film or the barrier film, those known in the art may be used.

One embodiment of the present specification provides a backlight unit including the color conversion film described above. The backlight unit may have backlight unit constitutions known in the art except for including the color conversion film. FIG. 1 is a mimetic diagram of a backlight unit structure according to one embodiment. The backlight unit according to FIG. 1 includes a side chain-type light source (101), a reflecting plate (102) surrounding the light source, a light guide plate (103) either directly emitting light from the light source or inducing light reflected from the reflecting plate, a reflective layer (104) provided on one surface of the light guide plate, and a color conversion film (105) provided on a surface of the light guide plate opposite to a surface facing the reflecting plate. A part marked in grey in FIG. 1 is a light dispersion pattern (106) of the light guide plate. Light entering into the light guide plate has non-uniform light distribution due to the repetition of optical processes such as reflection, total-reflection, refraction and transmission, and in order to induce this non-uniform light distribution to uniform brightness, a two-dimensional light dispersion pattern may be used. However, the scope of the present disclosure is not limited to FIG. 1, and the light source may use a direct type as well as a side chain type, and the reflecting plate or the reflective layer may not be included or may be replaced with other constituents as necessary, and when necessary, additional films such as a light diffusing film, a light concentrating film and a luminance enhancing film may be further provided.

One embodiment of the present specification provides a display apparatus including the backlight unit. The display apparatus is not particularly limited as long as it includes the backlight unit, and may be included in TVs, computer monitors, laptops, mobile phones and the like.

Hereinafter, the present specification will be described in detail with reference to examples. However, the examples according to the present specification may be modified to various other forms, and the scope of the present specification is not construed to be limited to the examples described below. The examples of the present specification are provided for more completely describing the present specification to those having average knowledge in the art.

PREPARATION EXAMPLE 1

Preparation of Compound 1-1

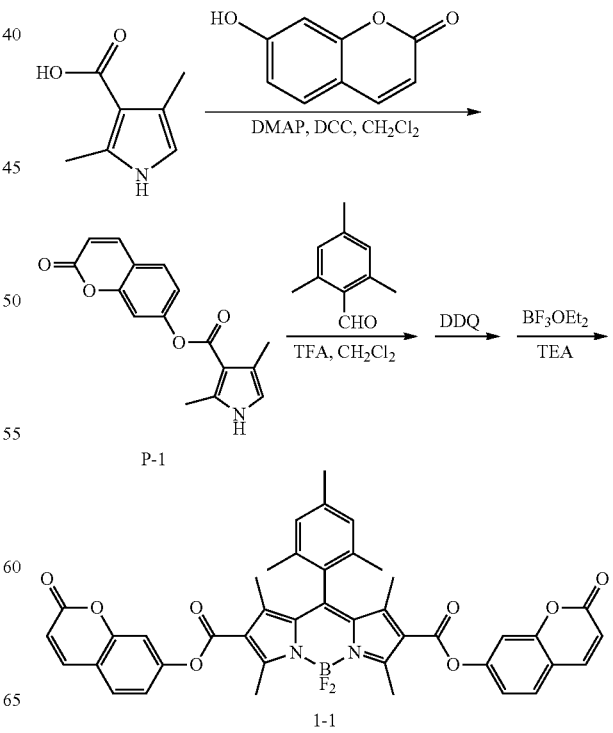

Preparation of Compound P-1: After placing 2,4-dimethyl-1H-pyrrole-3-carboxylic acid (3.1 g, 22.2 mmol) and dichloromethane (150 mL) in a flask, 4-dimethylaminopyridine (DMAP) (3.26 g, 26.6 mmol) and N,N'-dicyclohexylcarbodiimide (DCC) (5.5 g, 26.6 mmol) were added thereto, and the result was stirred for 30 minutes at room temperature. Umbelliferone was added thereto, and the result was stirred under reflux for 12 hours. After the temperature was lowered to room temperature, a saturated sodium hydroxide solution was introduced thereto, and the result was extracted with chloroform. The result was dried with anhydrous magnesium sulfate, filtered, and vacuum distilled to remove the solvent. White solid Compound P-1 (4.9 g, 78%) was obtained through a silica-gel column.

[M+H]$^+$=284

Preparation of Compound 1-1: After mixing P1 (3.0 g, 10.6 mol), mesityl aldehyde (0.78 g, 5.2 mol), trifluoroacetic acid (0.5 mL) and dry dichloromethane (200 mL) in a flask, the result was stirred under reflux for 12 hours under nitrogen. After identifying that the starting materials disappeared using TLC, 2,3-dichloro-5,6-dicyanobenzoquinone (DDQ) (1.2 g, 5.3 mol) was added thereto at 0° C. The result was stirred for 1 hour at room temperature, and then trimethylamine (26 g, 0.25 mol) was slowly added dropwise thereto. The result was stirred for 30 minutes at room temperature, and a boron trifluoride ethyl ether complex (65 g, 0.46 mol) was slowly added dropwise thereto. The reactant was stirred for 5 hours at room temperature, and extracted with dichloromethane after adding water thereto. The result was dried with anhydrous magnesium sulfate, filtered, and vacuum distilled to remove the solvent. Orange Compound 1-1 (2.6 g, 67%) was obtained through a silica-gel column (hexane/ethyl acetate).

FIG. 2 is a diagram showing a luminance spectrum of Compound 1-1, and maximum absorption and light emission wavelengths of Compound 1-1 in a toluene solution (1×10$^{-5}$ M) were 506 nm and 521 nm, respectively, and quantum efficiency was 0.94.

[M-F]$^+$=723

PREPARATION EXAMPLE 2

Preparation of Compound 1-23

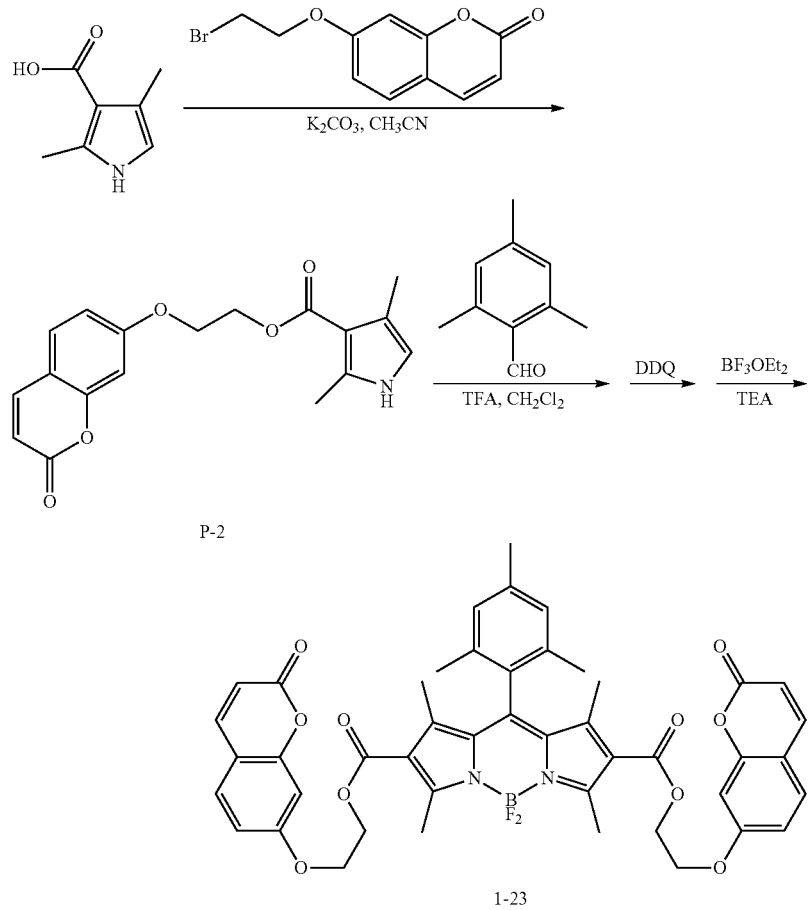

Preparation of Compound P-2: After placing 2,4-dimethyl-1H-pyrrole-3-carboxylic acid (4.0 g, 28.7 mmol), 7-(2-bromoethoxy)-2H-chromen-2-one (8.0 g, 29.7 mmol), K$_2$CO$_3$ (6.5 g, 47.0 mmol) and CH$_3$CN (150 mL) in a flask, the result was stirred for 12 hours at 70° C. After the temperature was lowered to room temperature, water was introduced thereto, and the result was extracted with chloroform. The result was dried with anhydrous magnesium sulfate, filtered, and vacuum distilled to remove the solvent. White solid Compound P-2 (6.1 g, 64%) was obtained through a silica-gel column.

[M+H]$^+$=328

Preparation of Compound 1-23: After mixing P-2 (2.5 g, 7.63 mol), mesityl aldehyde (0.78 g, 5.2 mol), trifluoroacetic acid (0.2 mL) and dry dichloromethane (200 mL) in a flask, the result was stirred under reflux for 12 hours under nitrogen. After identifying that the starting materials disappeared using TLC, 2,3-dichloro-5,6-dicyanobenzoquinone (DDQ) (1.2 g, 5.3 mol) was added thereto at 0° C. The result was stirred for 1 hour at room temperature, and then trimethylamine (26 g, 0.25 mol) was slowly added dropwise thereto. The result was stirred for 30 minutes at room temperature, and a boron trifluoride ethyl ether complex (40 g, 0.28 mol) was slowly added dropwise thereto. The reactant was stirred for 5 hours at room temperature, and extracted with dichloromethane after adding water thereto. The result was dried with anhydrous magnesium sulfate, filtered, and vacuum distilled to remove the solvent. Orange Compound 1-23 (1.7 g, 39%) was obtained through a silica-gel column (hexane/ethyl acetate).

FIG. 3 is a diagram showing a luminance spectrum of Compound 1-23, and maximum absorption and light emission wavelengths of Compound 1-23 in a toluene solution ($1 \times 10^{-5}$ M) were 504 nm and 516 nm, respectively, and quantum efficiency was 0.98.

$[M-F]^+=811$

PREPARATION EXAMPLE 3

Preparation of Compound 1-25

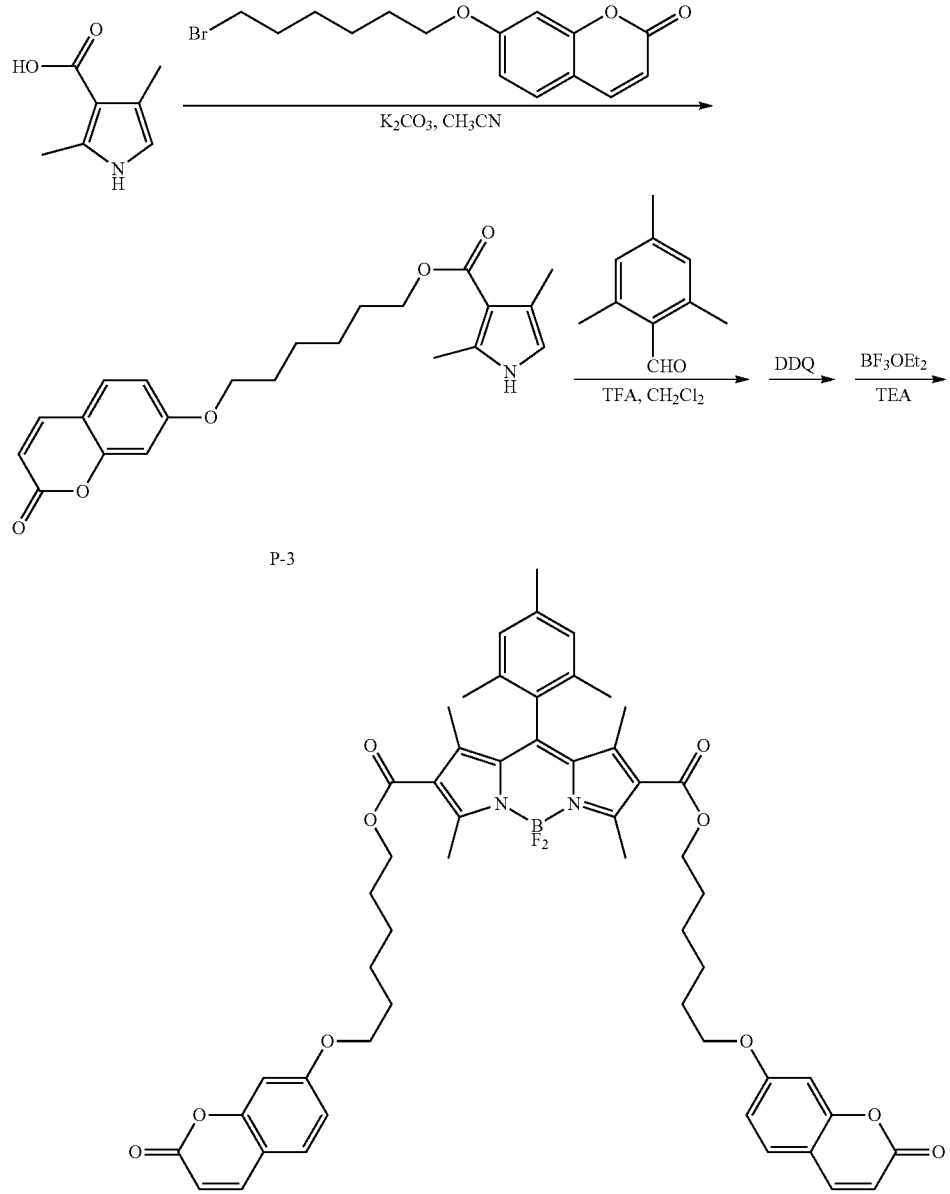

Preparation of Compound P-3: after placing 2,4-dimethyl-1H-pyrrole-3-carboxylic acid (3.5 g, 25.1 mmol), 7-((6-bromohexyl)oxy)-2H-chromen-2-one (8.2 g, 25.2 mmol), $K_2CO_3$ (5.3 g, 38.3 mmol) and $CH_3CN$ (150 mL) in a flask, the result was stirred for 12 hours at 70° C. After the temperature was lowered to room temperature, water was introduced thereto, and the result was extracted with chloroform. The result was dried with anhydrous magnesium sulfate, filtered, and vacuum distilled to remove the solvent. White solid Compound P-3 (6.9 g, 71%) was obtained through a silica-gel column.

$[M+H]^+=384$

Preparation of Compound 1-25: After mixing P-3 (4.5 g, 11.7 mol), mesityl aldehyde (0.87 g, 5.8 mol), trifluoroacetic acid (0.1 mL) and dry dichloromethane (200 mL) in a flask, the result was stirred under reflux for 12 hours under nitrogen. After identifying that the starting materials disappeared using TLC, 2,3-dichloro-5,6-dicyanobenzoquinone (DDQ) (1.4 g, 6.1 mol) was added thereto at 0° C. The result was stirred for 1 hour at room temperature, and then trimethylamine (30 g, 0.29 mol) was slowly added dropwise thereto. The result was stirred for 30 minutes at room temperature, and a boron trifluoride ethyl ether complex (50 g, 0.35 mol) was slowly added dropwise thereto. The reactant was stirred for 5 hours at room temperature, and extracted with dichloromethane after adding water thereto. The result was dried with anhydrous magnesium sulfate, filtered, and vacuum distilled to remove the solvent. Orange Compound 1-25 (2.9 g, 51%) was obtained through a silica-gel column (hexane/ethyl acetate).

FIG. 4 is a diagram showing a luminance spectrum of Compound 1-25, and maximum absorption and light emission wavelengths of Compound 1-25 in a toluene solution ($1 \times 10^{-5}$ M) were 505 nm and 517 nm, respectively, and quantum efficiency was 0.92.

$[M-F]^+ = 923$

PREPARATION EXAMPLE 4

Preparation of Compound 1-71

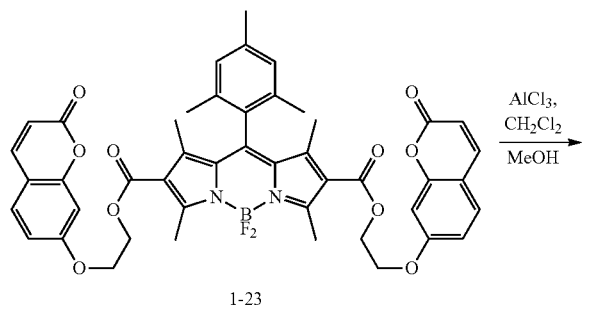

1-23

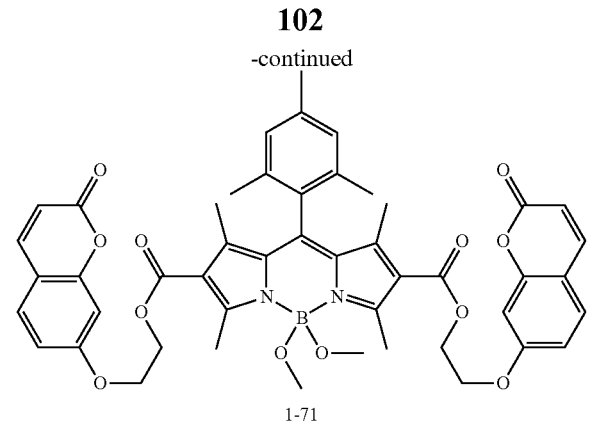

1-71

Preparation of Compound 1-71: After dissolving Compound 1-23 (1.2 g, 1.22 mmol) in dichloromethane under nitrogen, AlCl$_3$ (0.38 g, 2.62 mmol) was added thereto at 0° C. The result was stirred under reflux for 2 hours, and then methanol (0.50 g, 15.6 mmol) was added dropwise thereto. The result was stirred under reflux for 5 hours, the temperature was lowered to room temperature, and then water was added to the reaction solution. The result was extracted with dichloromethane, and then dried with anhydrous magnesium sulfate, filtered, and vacuum distilled to remove the solvent. Orange solid Compound 1-71 (0.87 g, 82%) was obtained through a silica-gel column.

FIG. 5 is a diagram showing a luminance spectrum of Compound 1-71, and maximum absorption and light emission wavelengths of Compound 1-71 in a toluene solution ($1 \times 10^{-5}$ M) were 504 nm and 516 nm, respectively, and quantum efficiency was 0.91.

$[M+H]^+ = 855$

PREPARATION EXAMPLE 5

Preparation of Compound 1-79

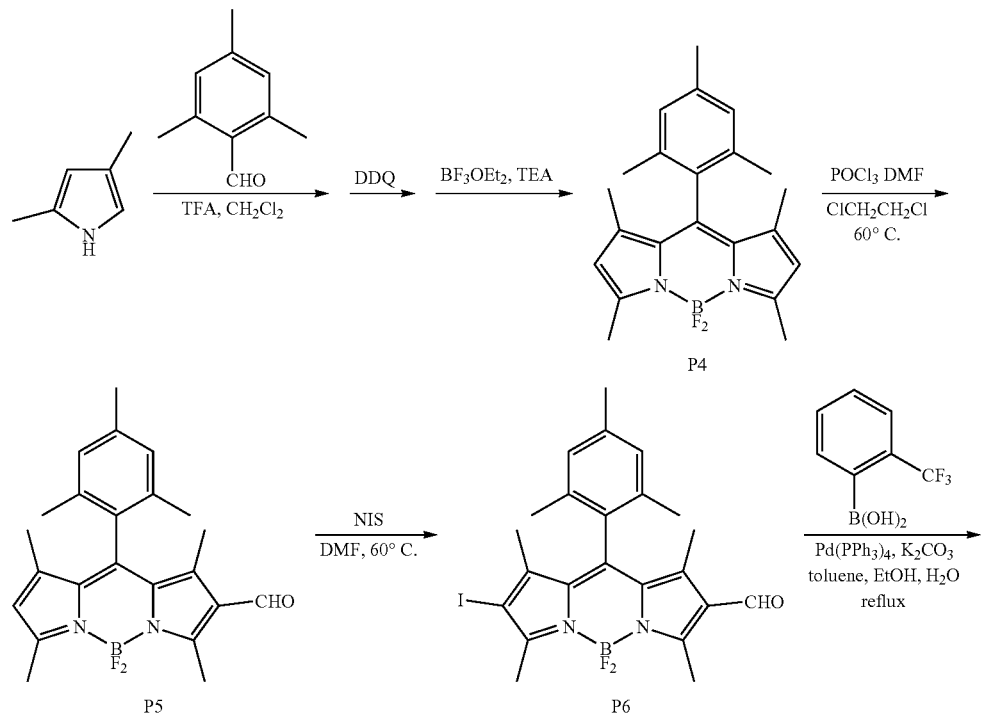

-continued
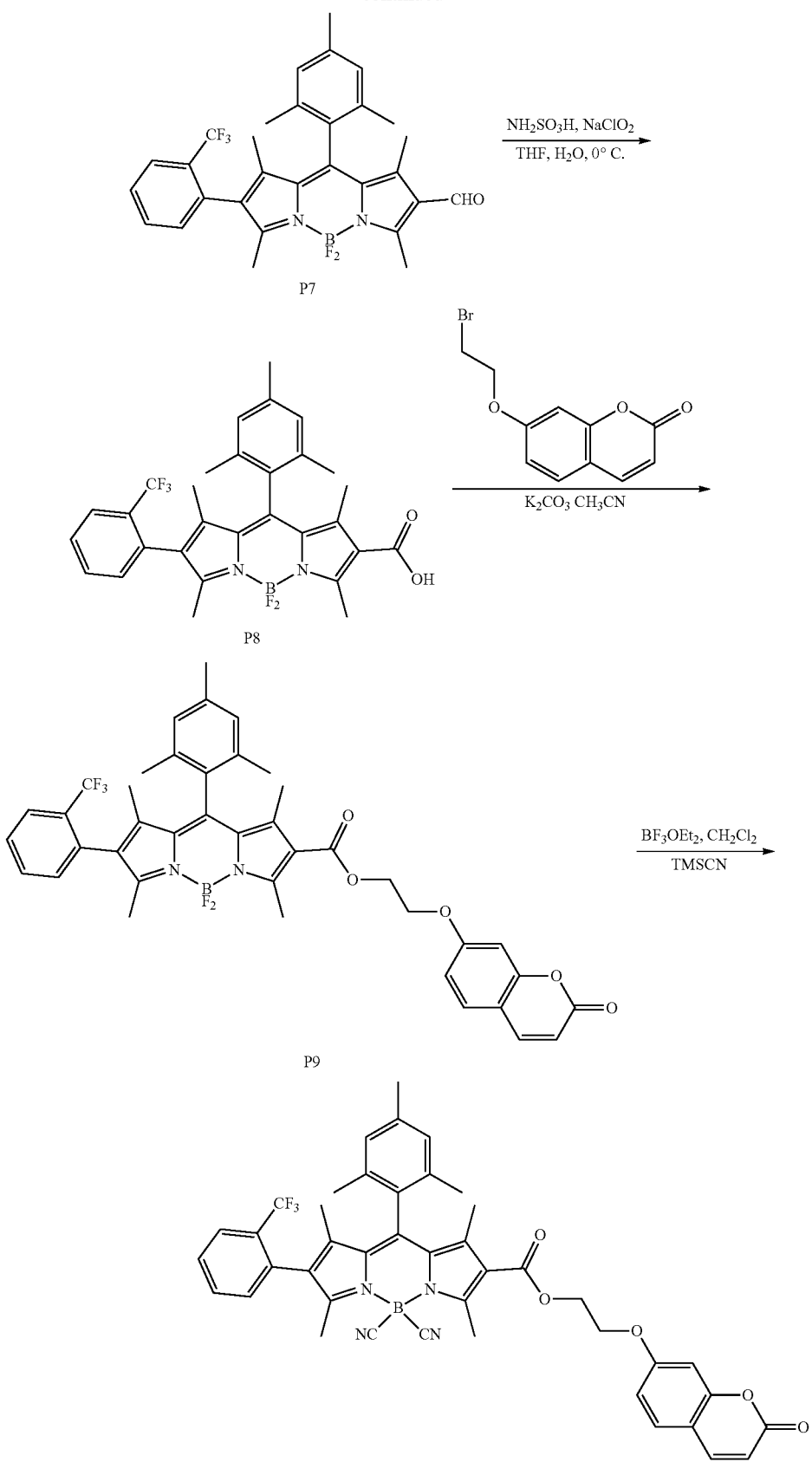
1-79

Preparation of Compound P4: After mixing 2,4-dimethylpyrrole (10 g, 0.10 mol), mesityl aldehyde (7.8 g, 0.052 mol), trifluoroacetic acid (2 drops) and dry dichloromethane (500 mL) in a flask, the result was stirred for 5 hours at room temperature under nitrogen. After identifying that the starting materials disappeared using TLC, DDQ (12 g, 0.052 mol) was added thereto at 0° C. The result was stirred for 1 hour at room temperature, and then trimethylamine (26 g, 0.25 mol) was slowly added dropwise thereto. The result was stirred for 30 minutes at room temperature, and a boron trifluoride ethyl ether complex (65 g, 0.46 mol) was slowly added dropwise thereto. The reactant was stirred for 5 hours at room temperature, and extracted with dichloromethane after adding water thereto. The result was dried with anhydrous magnesium sulfate, filtered, and vacuum distilled to remove the solvent. Red Compound P4 (7.8 g, 40%) was obtained through a silica-gel column (hexane/ethyl acetate).

$[M-F]^+=347$

Preparation of Compound P5: After mixing dimethylformamide (4 mL) and dichloroethane (50 mL) in a flask, the temperature was lowered to 0° C. $POCl_3$ (4 mL) was slowly added dropwise thereto under nitrogen atmosphere, and the result was stirred for 30 minutes at room temperature. Compound P4 (3 g, 8.2 mmol) was added to the reaction solution, the temperature was raised to 60° C., and the result was stirred for 1 hour. The result was cooled to room temperature, and then placed in a mixed solution of ice and saturated aqueous sodium hydroxide solution. The result was stirred for 2 hours at room temperature, and extracted with chloroform. The result was dried with anhydrous magnesium sulfate, filtered, and vacuum distilled to remove the solvent. Red Compound P5 (2.9 g, 89%) was obtained through a silica-gel column (hexane/ethyl acetate).

$[M-F]^+=375$

Preparation of Compound P6: After dissolving Compound P5 (2.1 g, 5.3 mmol) and N-iodosuccinimide (3.6 g, 16 mmol) in DMF in a flask, the result was stirred for 5 hours at 60° C. The result was cooled to room temperature, and water was added thereto to filter solids. The solids were dissolved in $CHCl_3$ and then washed with a saturated $Na_2S_2O_3$ solution thereto. The result was dried with anhydrous magnesium sulfate and then silica filtered. The result was vacuum distilled to remove the solvent, and went through a silica column (hexane/ethyl acetate) to obtain blackish red Compound P6 (2.3 g, 83%).

$[M-F]^+=501$

Preparation of Compound P7: After dissolving Compound P6 (2.0 g, 3.84 mmol) and 1-(trifluoromethyl)phenylboronic acid (0.91 g, 4.79 mmol) in toluene and ethanol, potassium carbonate ($K_2CO_3$, 1.60 g, 11.5 mmol) was added to the reaction solution with water, and tetrakis(triphenylphosphine)palladium (0.2 g, 0.16 mmol) was added thereto. The result was stirred under reflux for 5 hours, cooled to room temperature, and extracted with chloroform. The result was dried with anhydrous magnesium sulfate, filtered, and vacuum distilled to remove the solvent. Red solid Compound P7 (1.71 g, 82%) was obtained through a silica-gel column.

$[M-F]^+=519$

Preparation of Compound P8: After dissolving Compound P7 (1.5 g, 2.78 mmol) and $NH_2SO_3H$ (0.30 g, 3.09 mol) in tetrahydrofuran, $NaClO_2$ (0.26 g, 2.87 mmol) dissolved in water was slowly added dropwise thereto at 0° C. The result was stirred for 1 hour, and extracted with chloroform after adding a saturated $Na_2S_2O_3$ solution thereto. The result was dried with anhydrous magnesium sulfate, filtered, and vacuum distilled to remove the solvent, and as a result, red Compound P8 (1.39 g, 89%) was obtained.

$[M-F]^+=535$

Preparation of P9: After placing P8 (1.1 g, 1.98 mmol), 7-((6-bromohexyl)oxy)-2H-chromen-2-one (0.65 g, 2.4 mmol), $K_2CO_3$ (0.5 g, 3.61 mmol) and $CH_3CN$ (50 mL) in a flask, the result was stirred for 12 hours at 70° C. The temperature was lowered to room temperature, water was added thereto, and the result was extracted with chloroform. The result was dried with anhydrous magnesium sulfate, filtered, and vacuum distilled to remove the solvent. Orange solid Compound P9 (1.1 g, 77%) was obtained through a silica-gel column.

$[M-F]^+=723$

Preparation of Compound 1-79: After dissolving Compound P9 (1.0 g, 1.34 mmol) in dichloromethane, a boron trifluoride ethyl ether complex (0.40 g, 2.81 mmol) was slowly added dropwise thereto at 0° C. The result was stirred for 3 hours at room temperature, and then TMSCN (0.50 g, 5.03 mmol) was added dropwise thereto. The result was stirred for 5 hours at room temperature, and extracted with chloroform after adding a saturated $NaHCO_3$ solution thereto. The result was dried with anhydrous magnesium sulfate, filtered, and vacuum distilled to remove the solvent. Orange solid Compound 1-79 (0.67 g, 65%) was obtained through a silica-gel column.

FIG. 6 is a diagram showing a luminance spectrum of Compound 1-79, and maximum absorption and light emission wavelengths of Compound 1-79 in a toluene solution ($1\times10^{-5}$ M) were 506 nm and 519 nm, respectively, and quantum efficiency was 0.91.

$[M+H]^+=757$

PREPARATION EXAMPLE 6

Preparation of Compound 1-80

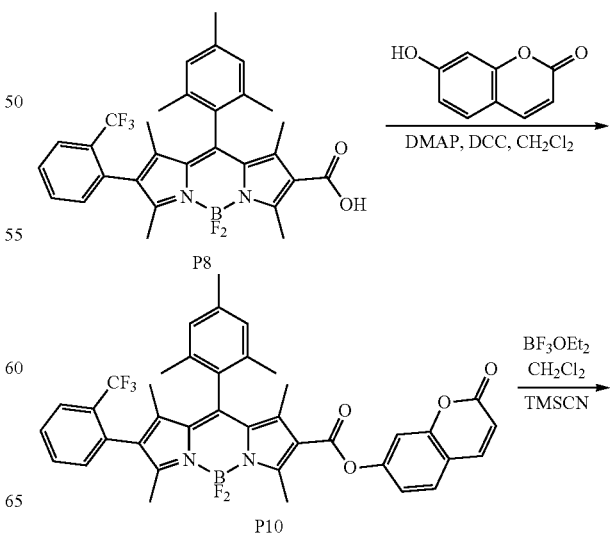

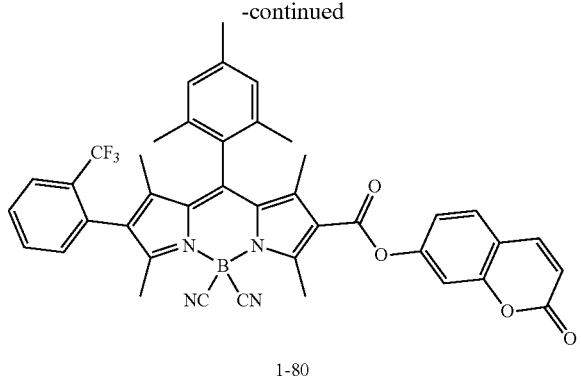

1-80

Preparation of Compound P-10: After placing P8 (2.0 g, 3.60 mmol) and dichloromethane (100 mL) in a flask, DMAP (0.53 g, 4.33 mmol) and N,N'-DICYCLOHEXYL-CARBODIIMIDE (DCC) (0.87 g, 4.21 mmol) were added thereto, and the result was stirred for 30 minutes at room temperature. Umbelliferone (0.65 g, 4.00 mol) was added thereto, and the result was stirred under reflux for 12 hours. After the temperature was lowered to room temperature, a saturated sodium hydroxide solution was introduced thereto, and the result was extracted with chloroform. The result was dried with anhydrous magnesium sulfate, filtered, and vacuum distilled to remove the solvent. White solid Compound P10 (2.1 g, 83%) was obtained through a silica-gel column.

[M-F]$^+$=679

Preparation of Compound 1-80: After dissolving Compound P10 (1.2 g, 1.71 mmol) in dichloromethane, a boron trifluoride ethyl ether complex (0.49 g, 3.45 mmol) was slowly added dropwise thereto at 0° C. The result was stirred for 3 hours at room temperature, and then TMSCN (0.70 g, 7.05 mmol) was added dropwise thereto. The result was stirred for 5 hours at room temperature, and extracted with chloroform after adding a saturated NaHCO$_3$ solution thereto. The result was dried with anhydrous magnesium sulfate, filtered, and vacuum distilled to remove the solvent. Orange solid Compound 1-80 (0.71 g, 57%) was obtained through a silica-gel column.

FIG. 7 is a diagram showing a luminance spectrum of Compound 1-80, and maximum absorption and light emission wavelengths of Compound 1-80 in a toluene solution (1×10$^{-5}$ M) were 505 nm and 517 nm, respectively, and quantum efficiency was 0.99.

[M+H]$^+$=757

PREPARATION EXAMPLE 7

Preparation of Compound 1-82

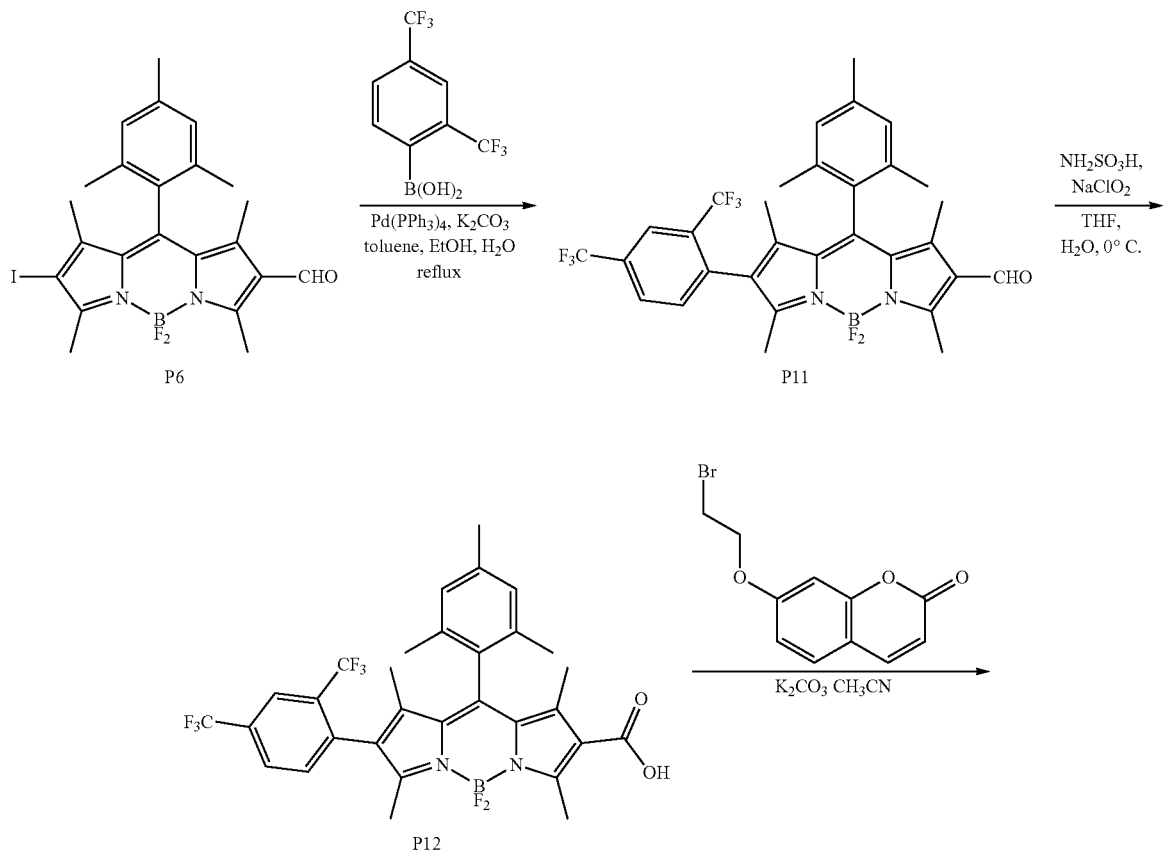

-continued

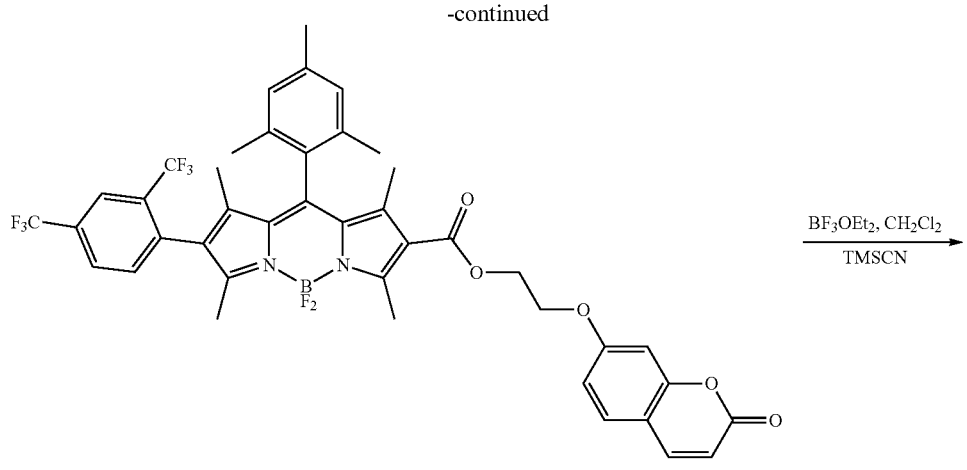

P13

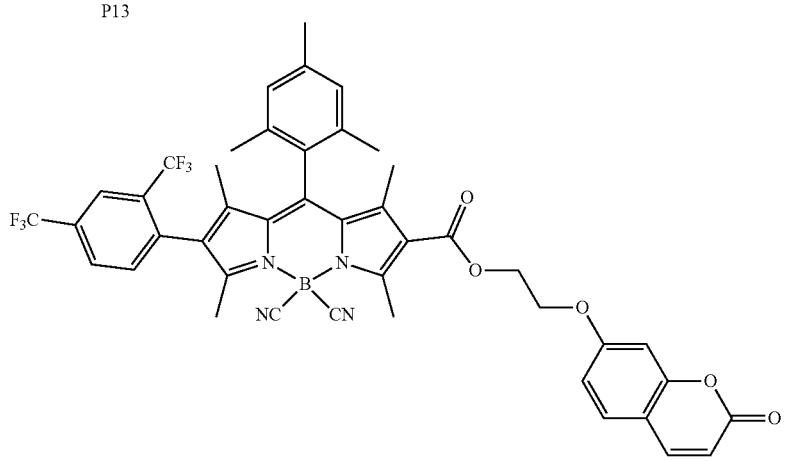

1-82

Preparation of Compound P11: After dissolving Compound P6 (2.0 g, 3.84 mmol) and (2,4-bis(trifluoromethyl)phenyl)boronic acid (1.50 g, 5.81 mmol) in toluene and ethanol, potassium carbonate ($K_2CO_3$, 1.60 g, 11.5 mmol) was added to the reaction solution with water, and tetrakis(triphenylphosphine)palladium (0.2 g, 0.16 mmol) was added thereto. The result was stirred under reflux for 5 hours, cooled to room temperature, and extracted with chloroform. The result was dried with anhydrous magnesium sulfate, filtered, and vacuum distilled to remove the solvent. Red solid Compound P11 (1.80 g, 77%) was obtained through a silica-gel column.

$[M-F]^+=587$

Preparation of Compound P12: After dissolving Compound P11 (1.5 g, 2.47 mmol) and $NH_2SO_3H$ (0.30 g, 3.09 mol) in tetrahydrofuran, $NaClO_2$ (0.26 g, 2.87 mmol) dissolved in water was slowly added dropwise thereto at 0° C. The result was stirred for 1 hour, and extracted with chloroform after adding a saturated $Na_2S_2O_3$ solution thereto. The result was dried with anhydrous magnesium sulfate, filtered, and vacuum distilled to remove the solvent, and as a result, red Compound P12 (1.40 g, 90%) was obtained.

$[M-F]^+=603$

Preparation of Compound P13: After placing P12 (1.3 g, 2.08 mmol), 7-((6-bromohexyl)oxy)-2H-chromen-2-one (0.65 g, 2.4 mmol), $K_2CO_3$ (0.5 g, 3.61 mmol) and $CH_3CN$ (50 mL) in a flask, the result was stirred for 12 hours at 70° C. The temperature was lowered to room temperature, water was added thereto, and the result was extracted with chloroform. The result was dried with anhydrous magnesium sulfate, filtered, and vacuum distilled to remove the solvent. Orange solid Compound P13 (1.4 g, 82%) was obtained through a silica-gel column.

$[M-F]^+=791$

Preparation of Compound 1-82: After dissolving Compound P13 (1.0 g, 1.23 mmol) in dichloromethane, a boron trifluoride ethyl ether complex (0.40 g, 2.81 mmol) was slowly added dropwise thereto at 0° C. The result was stirred for 3 hours at room temperature, and then TMSCN (0.50 g, 5.03 mmol) was added dropwise thereto. The result was stirred for 5 hours at room temperature, and extracted with chloroform after adding a saturated $NaHCO_3$ solution thereto. The result was dried with anhydrous magnesium sulfate, filtered, and vacuum distilled to remove the solvent. Orange solid Compound 1-82 (0.71 g, 70%) was obtained through a silica-gel column.

FIG. 8 is a diagram showing a luminance spectrum of Compound 1-82, and maximum absorption and light emission wavelengths of Compound 1-82 in a toluene solution ($1\times10^{-5}$ M) were 506 nm and 519 nm, respectively, and quantum efficiency was 0.89.

$[M+H]^+=825$

PREPARATION EXAMPLE 8
Preparation of Compound 1-83
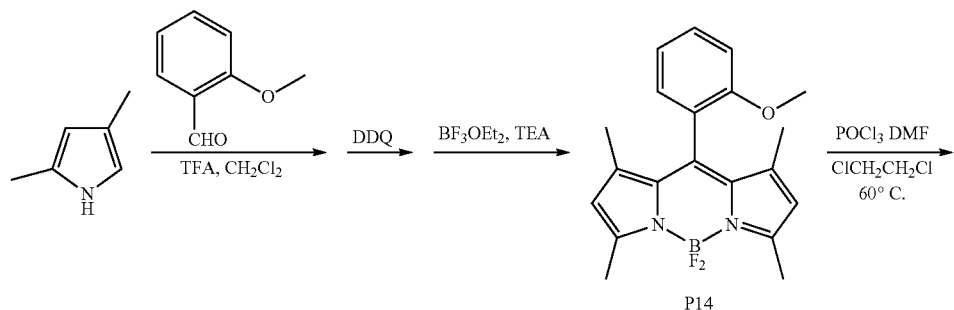
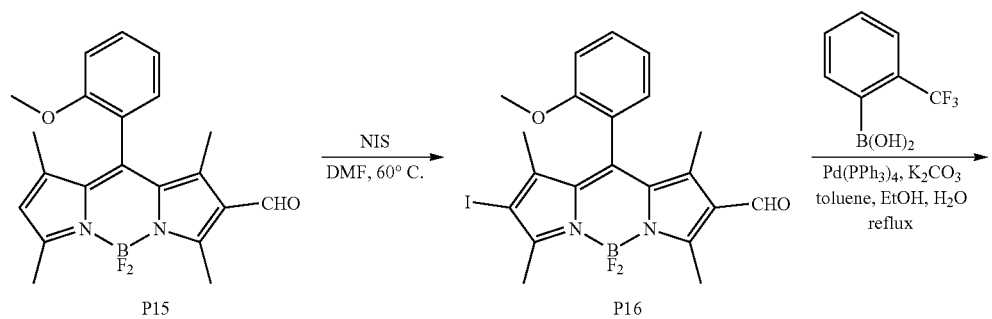
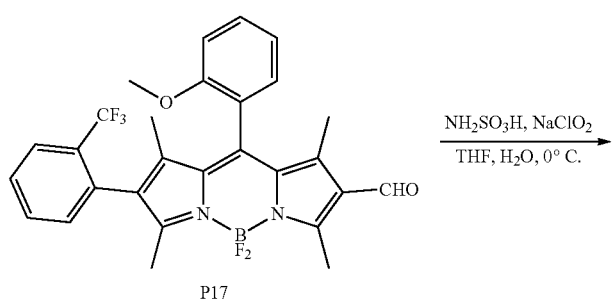
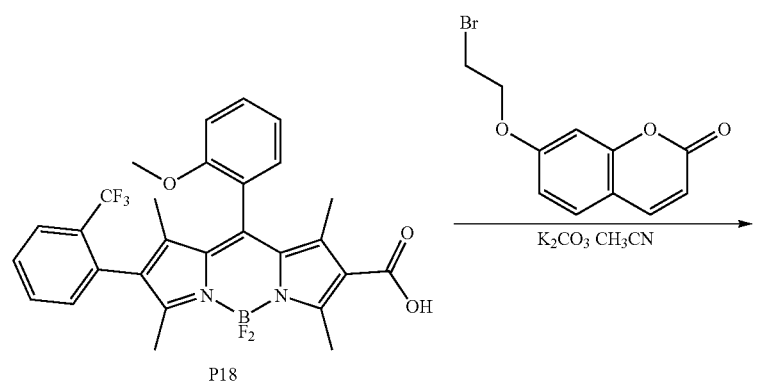

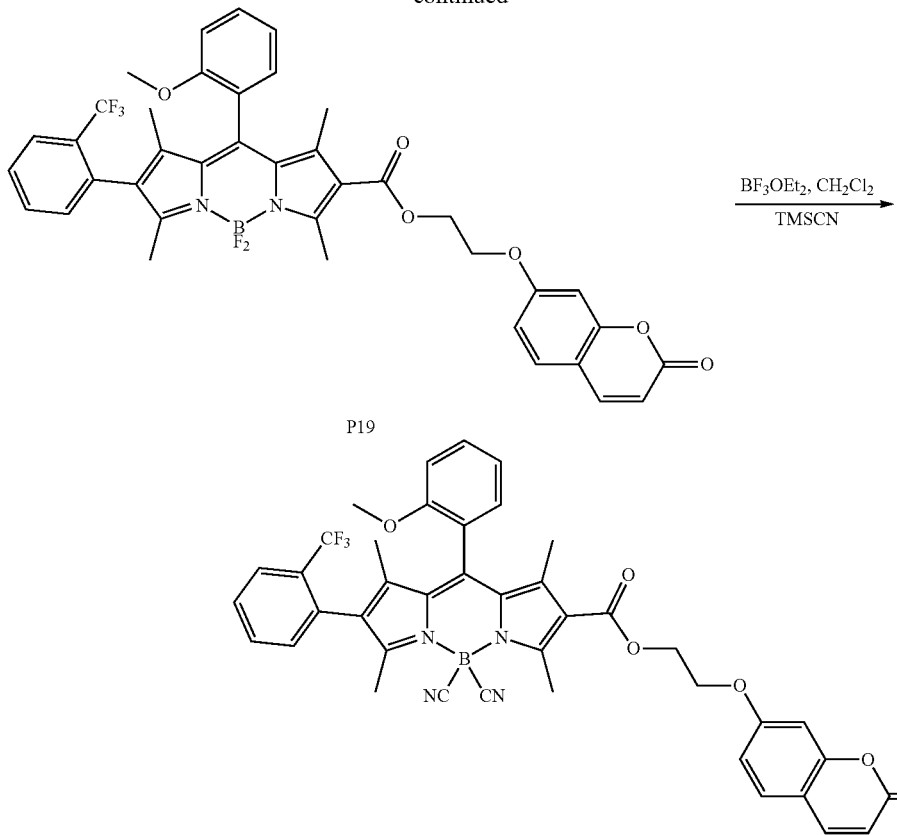

Preparation of Compound P14: After mixing 2,4-dimethylpyrrole (10 g, 0.10 mol), 2-methoxybenzaldehyde (7.1 g, 0.052 mol), trifluoroacetic acid (2 drops) and dry dichloromethane (500 mL) in a flask, the result was stirred at room temperature for 5 hours under nitrogen. After identifying that the starting materials disappeared using TLC, DDQ (12 g, 0.052 mol) was added thereto at 0° C. The result was stirred for 1 hour at room temperature, and then trimethylamine (26 g, 0.25 mol) was slowly added dropwise thereto. The result was stirred for 30 minutes at room temperature, and a boron trifluoride ethyl ether complex (65 g, 0.46 mol) was slowly added dropwise thereto. The reactant was stirred for 5 hours at room temperature, and extracted with dichloromethane after adding water thereto. The result was dried with anhydrous magnesium sulfate, filtered, and vacuum distilled to remove the solvent. Red Compound P14 (9.8 g, 52%) was obtained through a silica-gel column (hexane/ethyl acetate).

[M-F]$^+$=335

Preparation of Compound P15: After mixing dimethylformamide (4 mL) and dichloroethane (50 mL) in a flask, the temperature was lowered to 0° C. POCl$_3$ (4 mL) was slowly added dropwise thereto under nitrogen atmosphere, and the result was stirred for 30 minutes at room temperature. Compound P14 (3.1 g, 8.7 mmol) was added to the reaction solution, the temperature was raised to 60° C., and the result was stirred for 1 hour. The result was cooled to room temperature, and placed in a mixed solution of ice and saturated aqueous sodium hydroxide solution. The result was stirred for 2 hours at room temperature, and extracted with chloroform. The result was dried with anhydrous magnesium sulfate, filtered, and vacuum distilled to remove the solvent. Red solid Compound P15 (2.7 g, 80%) was obtained through a silica-gel column (hexane/ethyl acetate).

[M-F]$^+$=363

Preparation of Compound P16: After dissolving Compound P15 (2.5 g, 6.5 mmol) and N-iodosuccinimide (3.0 g, 13.3 mmol) in DMF in a flask, the result was stirred for 5 hours at 60° C. The result was cooled to room temperature, and water was added thereto to filter solids. The solids were dissolved in CHCl$_3$ and then washed with a saturated Na$_2$S$_2$O$_3$ solution thereto. The result was dried with anhydrous magnesium sulfate and then silica filtered. The result was vacuum distilled to remove the solvent, and went through a silica column (hexane/ethyl acetate) to obtain blackish red Compound P16 (2.4 g, 72%).

[M-F]$^+$=489

Preparation of Compound P17: After dissolving Compound P16 (2.0 g, 3.93 mmol) and 1-(trifluoromethyl) phenylboronic acid (0.91 g, 4.79 mmol) in toluene and ethanol, potassium carbonate (K$_2$CO$_3$, 1.60 g, 11.5 mmol) was added to the reaction solution with water, and tetrakis (triphenylphosphine)palladium (0.2 g, 0.16 mmol) was added thereto. The result was stirred under reflux for 5 hours, cooled to room temperature, and extracted with chloroform. The result was dried with anhydrous magnesium sulfate, filtered, and vacuum distilled to remove the solvent. Red solid Compound P17 (1.70 g, 82%) was obtained through a silica-gel column.

[M-F]$^+$=507

Preparation of Compound P18: After dissolving Compound P17 (1.5 g, 2.85 mmol) and NH$_2$SO$_3$H (0.30 g, 3.09 mol) in tetrahydrofuran, NaClO₂ (0.26 g, 2.87 mmol) dissolved in water was slowly added dropwise thereto at 0° C. The result was stirred for 1 hour, and extracted with chloroform after adding a saturated Na₂S₂O₃ solution thereto. The result was dried with anhydrous magnesium sulfate, filtered, and vacuum distilled to remove the solvent, and as a result, red Compound P18 (1.2 g, 78%) was obtained.

[M-F]⁺=523

Preparation of Compound P19: After placing P18 (1.0 g, 1.84 mmol), 7-((6-bromohexyl)oxy)-2H-chromen-2-one (0.65 g, 2.4 mmol), K₂CO₃ (0.5 g, 3.61 mmol) and CH₃CN (50 mL) in a flask, the result was stirred for 12 hours at 70° C. The temperature was lowered to room temperature, water was added thereto, and the result was extracted with chloroform. The result was dried with anhydrous magnesium sulfate, filtered, and vacuum distilled to remove the solvent. Orange solid Compound P19 (1.0 g, 74%) was obtained through a silica-gel column.

[M-F]⁺=711

Preparation of Compound 1-83: After dissolving Compound P19 (1.0 g, 1.36 mmol) in dichloromethane, a boron trifluoride ethyl ether complex (0.40 g, 2.81 mmol) was slowly added dropwise thereto at 0° C. The result was stirred for 3 hours at room temperature, and then trimethylsilyl cyanide(TMSCN) (0.50 g, 5.03 mmol) was added dropwise thereto. The result was stirred for 5 hours at room temperature, and extracted with chloroform after adding a saturated NaHCO₃ solution thereto. The result was dried with anhydrous magnesium sulfate, filtered, and vacuum distilled to remove the solvent. Orange solid Compound 1-83 (0.65 g, 64%) was obtained through a silica-gel column.

FIG. 9 is a diagram showing luminance spectrum of Compound 1-83, and maximum absorption and light emission wavelengths of Compound 1-83 in a toluene solution (1×10⁻⁵ M) were 506 nm and 520 nm, respectively, and quantum efficiency was 0.96.

[M+H]⁺=745

PREPARATION EXAMPLE 9

Preparation of Compound 1-84

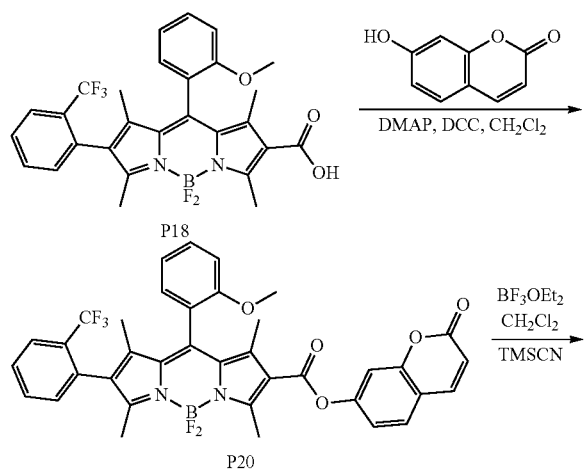

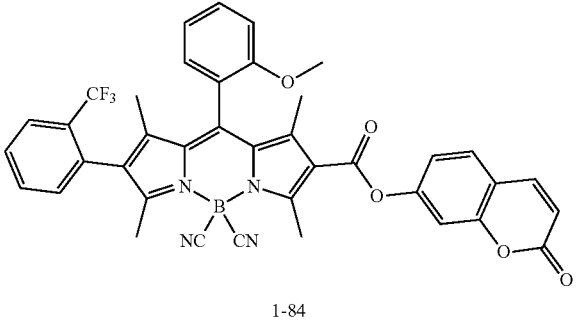

1-84

Preparation of Compound P20: After placing P18 (2.0 g, 3.68 mmol) and dichloromethane (100 mL) in a flask, DMAP (0.53 g, 4.33 mmol) and N,N'-DICYCLOHEXYL-CARBODIIMIDE (DCC) (0.87 g, 4.21 mmol) were added thereto, and the result was stirred for 30 minutes at room temperature. Umbelliferone (0.65 g, 4.00 mol) was added thereto, and the result was stirred under reflux for 12 hours. After the temperature was lowered to room temperature, a saturated sodium hydroxide solution was introduced thereto, and the result was extracted with chloroform. The result was dried with anhydrous magnesium sulfate, filtered, and vacuum distilled to remove the solvent. White solid Compound P20 (1.8 g, 71%) was obtained through a silica-gel column.

[M-F]+=667

Preparation of Compound 1-84: After dissolving Compound P20 (1.2 g, 1.75 mmol) in dichloromethane, a boron trifluoride ethyl ether complex (0.49 g, 3.45 mmol) was slowly added dropwise thereto at 0° C. The result was stirred for 3 hours at room temperature, and then TMSCN (0.70 g, 7.05 mmol) was added dropwise thereto. The result was stirred for 5 hours at room temperature, and extracted with chloroform after adding a saturated NaHCO₃ solution thereto. The result was dried with anhydrous magnesium sulfate, filtered, and vacuum distilled to remove the solvent. Orange solid Compound 1-84 (0.66 g, 53%) was obtained through a silica-gel column.

FIG. 10 is a diagram showing a luminance spectrum of Compound 1-84, and maximum absorption and light emission wavelengths of Compound 1-84 in a toluene solution (1×10⁻⁵ M) were 506 nm and 518 nm, respectively, and quantum efficiency was 0.99.

[M+H]+=701

EXAMPLE 1

A first solution was prepared by dissolving Compound 1-1 in solvent toluene. A second solution was prepared by dissolving a thermoplastic resin SAN in solvent toluene. The first solution and the second solution were mixed so that the amount of the organic fluorescent substance was 0.3 parts by weight and the amount of TiO₂ was 5 parts by weight based on 100 parts by weight of the SAN, and TiO₂ was added thereto so that the amount of TiO₂ was 5 parts by weight based on 100 parts by weight of the SAN, and the result was uniformly mixed. The solid content of the mixed solution was 20% by weight and viscosity was 200 cps. This solution was coated on a PET substrate, and the result was dried to prepare a color conversion film. The prepared color conversion film has a thickness of 10 nm to 15 mm, and a haze value of 73%. A luminance spectrum of the prepared color conversion film was measured using a spectroradiometer (SR series of TOPCON Corporation). Specifically, the prepared color conversion film was laminated on one surface of a light guide plate of a backlight unit including a LED blue backlight (maximum light emission wavelength 450 nm) and the light guide plate, and after laminating a prism sheet and a DBEF film on the color conversion film, a luminance spectrum of the film was measured. When measuring the luminance spectrum, an initial value was set so that the brightness of the blue LED light was 600 nit based on without the color conversion film. The color conversion film emitted light at 537 nm under blue LED light.

Under a temperature condition of 60° C., the intensity of green fluorescence decreased by 22% after 500 hours under blue backlight (600 nit) driving.

EXAMPLE 2

A color conversion film was prepared in the same manner as in Example 1 except that Compound 1-23 was used instead of Compound 1-1. The color conversion film emitted light at 532 nm under blue LED light. Under a temperature condition of 60° C., the intensity of green fluorescence decreased by 20% after 500 hours under blue backlight (600 nit) driving.

EXAMPLE 3

A color conversion film was prepared in the same manner as in Example 1 except that Compound 1-25 was used instead of Compound 1-1. The color conversion film emitted light at 534 nm under blue LED light. Under a temperature condition of 60° C., the intensity of green fluorescence decreased by 23% after 500 hours under blue backlight (600 nit) driving.

EXAMPLE 4

A color conversion film was prepared in the same manner as in Example 1 except that Compound 1-71 was used instead of Compound 1-1. The color conversion film emitted light at 526 nm under blue LED light. Under a temperature condition of 60° C., the intensity of green fluorescence decreased by 18% after 500 hours under blue backlight (600 nit) driving.

EXAMPLE 5

A color conversion film was prepared in the same manner as in Example 1 except that Compound 1-79 was used instead of Compound 1-1. The color conversion film emitted light at 537 nm under blue LED light. Under a temperature condition of 60° C., the intensity of green fluorescence decreased by 10% after 500 hours under blue backlight (600 nit) driving.

EXAMPLE 6

A color conversion film was prepared in the same manner as in Example 1 except that Compound 1-80 was used instead of Compound 1-1. The color conversion film emitted light at 537 nm under blue LED light. Under a temperature condition of 60° C., the intensity of green fluorescence decreased by 9% after 500 hours under blue backlight (600 nit) driving.

EXAMPLE 7

A color conversion film was prepared in the same manner as in Example 1 except that Compound 1-82 was used instead of Compound 1-1. The color conversion film emitted light at 532 nm under blue LED light. Under a temperature condition of 60° C., the intensity of green fluorescence decreased by 11% after 500 hours under blue backlight (600 nit) driving.

EXAMPLE 8

A color conversion film was prepared in the same manner as in Example 1 except that Compound 1-83 was used instead of Compound 1-1. The color conversion film emitted light at 537 nm under blue LED light. Under a temperature condition of 60° C., the intensity of green fluorescence decreased by 12% after 500 hours under blue backlight (600 nit) driving.

EXAMPLE 9

A color conversion film was prepared in the same manner as in Example 1 except that Compound 1-84 was used instead of Compound 1-1. The color conversion film emitted light at 537 nm under blue LED light. Under a temperature condition of 60° C., the intensity of green fluorescence decreased by 13% after 500 hours under blue backlight (600 nit) driving.

COMPARATIVE EXAMPLE 1

Comparative Example Compound 1

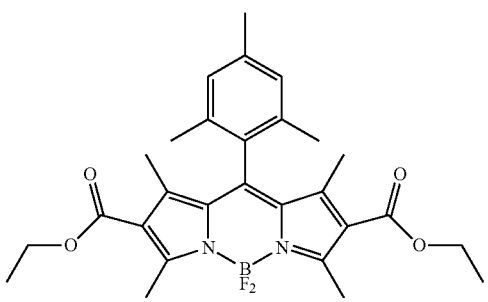

A color conversion film was prepared in the same manner as in Example 1 except that Comparative Example Compound 1 was used instead of Compound 1-1. The color conversion film emitted light at 532 nm under blue LED light. Under a temperature condition of 60° C., the intensity of green fluorescence decreased by 60% after 500 hours under blue backlight (600 nit) driving.

COMPARATIVE EXAMPLE 2

Comparative Example Compound 2

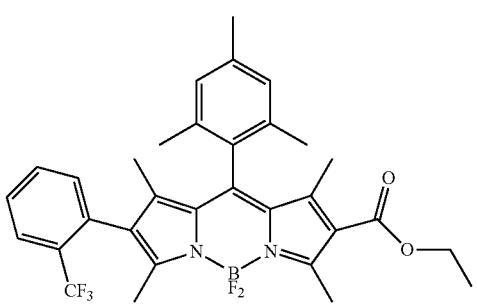

A color conversion film was prepared in the same manner as in Example 1 except that Comparative Example Compound 2 was used instead of Compound 1-1. The color conversion film emitted light at 538 nm under blue LED light. Under a temperature condition of 60° C., the intensity of green fluorescence decreased by 58% after 500 hours under blue backlight (600 nit) driving.

As seen from Examples 1 to 9, and Comparative Examples 1 and 2, the compounds represented by Chemical Formula 1 according to one embodiment of the present specification are capable of being used in the preparation of color conversion films having superior light resistance compared to Comparative Example Compound 1 and Comparative Example Compound 2 that are existing compounds.

EXPLANATION OF REFERENCE NUMERALS AND SYMBOLS

101: Side Chain-Type Light Source
102: Reflecting Plate
103: Light Guide Plate
104: Reflective Layer
105: Color Conversion Film
106: Light Dispersion Pattern

The invention claimed is:

1. A compound of the following Chemical Formula 1:

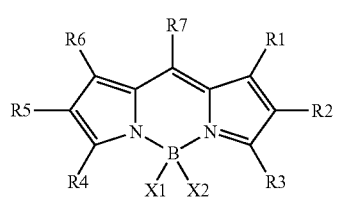

[Chemical Formula 1]

wherein, in Chemical Formula 1,

X1 and X2 are the same as or different from each other, and each independently a halogen group; a nitrile group; a substituted or unsubstituted alkyl group; a substituted or unsubstituted alkoxy group; —O(C=O)R; a substituted or unsubstituted alkenyl group; a substituted or unsubstituted alkynyl group; a substituted or unsubstituted aryl group; or a substituted or unsubstituted heteroaryl group;

R is a substituted or unsubstituted alkyl group;

at least one of R1, R2, R5, and R6 is a substituent of the following Chemical Formula 2, and the rest in addition to R3 and R4 are the same as or different from each other and each independently a group of the following Chemical Formula 3; hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group;

R7 is a substituent of formula -(L)$_r$-A;

L is a direct bond; —O—; —N(H)—; —OC(=O)—; a substituted or unsubstituted alkylene group; a substituted or unsubstituted arylene group; or a substituted or unsubstituted heteroarylene group;

A is a group of the following Chemical Formula 3; hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group;

r is an integer of 1 to 10;

when r is 2 or greater, 2 or more Ls are the same as or different from each other;

[Chemical Formula 2]

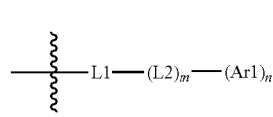

wherein, in Chemical Formula 2,

L1 is a group of any one of the following Chemical Formulae 4 to 6;

L2 is a direct bond; —O—; —N(H)—; —OC(=O)—; a substituted or unsubstituted alkylene group; a substituted or unsubstituted arylene group; or a substituted or unsubstituted heteroarylene group;

Ar1 is a group of the following Chemical Formula 3;

m is an integer of 1 to 5;

n is an integer of 1 to 3;

when m and n are each 2 or greater, the 2 or more structures in the parentheses are the same as or different from each other;

is a site bonding to at least one of R1 to R6 of Chemical Formula 1;

[Chemical Formula 3]

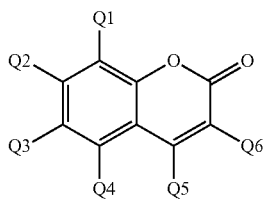

[Chemical Formula 5]

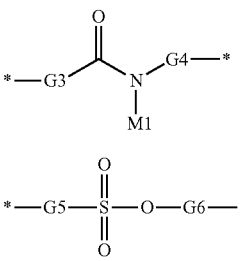

[Chemical Formula 6]

*—G5—S(=O)(=O)—O—G6—* wherein, in Chemical Formula 3, any one of Q1 to Q6 is a site bonding to L2 of Chemical Formula 2 or a site bonding to any one of R1 to R7 of Chemical Formula 1, and the rest are the same as or different from each other and each independently hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring;

[Chemical Formula 4]

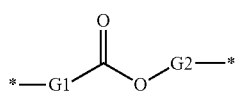

wherein, in Chemical Formulae 4 to 6,

* is a site bonding to at least one of R1 to R6 of Chemical Formula 1 or a site bonding to L2 of Chemical Formula 2;

G1 to G6 are the same as or different from each other, and each independently a direct bond; —O—; —N(H)—; —OC(=O)—; a substituted or unsubstituted alkylene group; a substituted or unsubstituted arylene group; or a substituted or unsubstituted heteroarylene group; and M1 is hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

2. The compound of claim 1, wherein, in Chemical Formula 1, at least one of R2 and R5 is a substituent of Chemical Formula 2.

3. The compound of claim 1, wherein Chemical Formula 1 is a compound of the following Chemical Formula 1-1 or 1-2:

[Chemical Formula 1-1]

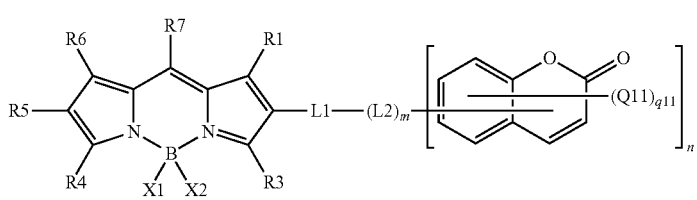

[Chemical Formula 1-2]

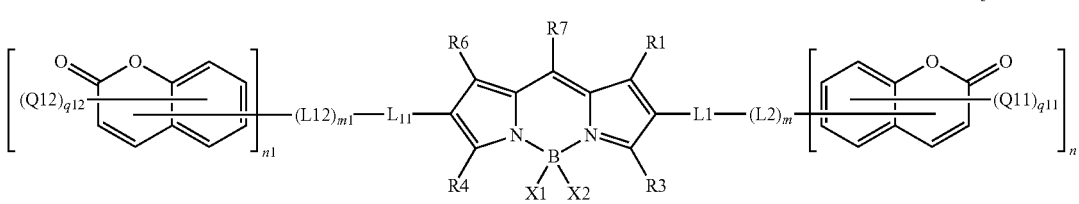

wherein, in Chemical Formulae 1-1 and 1-2,
definitions of R1 to R7, and X1 and X2 are the same as in Chemical Formula 1;
definitions of L1, L2, m and n are the same as in Chemical Formula 2;
Q11 and Q12 are the same as or different from each other, and each independently hydrogen; deuterium; a halogen group; a nitrile group; a nitro group; a hydroxyl group; a carboxyl group (—COOH); an ether group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, or adjacent groups bond to each other to form a substituted or unsubstituted ring;
L11 is a group of any one of Chemical Formulae 4 to 6;
L12 is a direct bond; —O—; —N(H)—; —OC(=O)—; a substituted or unsubstituted alkylene group; a substituted or unsubstituted arylene group; or a substituted or unsubstituted heteroarylene group;
q11, q12 and m1 are each an integer of 1 to 5;
n1 is an integer of 1 to 3; and
when q11, q12, m1 and n1 are each 2 or greater, the 2 or more structures in the parentheses are the same as or different from each other.

4. The compound of claim 1, wherein X1 and X2 are the same as or different from each other, and each independently a halogen group; a nitrile group; an alkoxy group unsubstituted or substituted with a halogen group; —O(C=O)R; an alkynyl group unsubstituted or substituted with a silyl group substituted with an alkyl group, an aryl group unsubstituted or substituted with an alkyl group, the group of Chemical Formula 3 or a heteroaryl group; or an aryl group unsubstituted or substituted with a halogen group, an alkyl group unsubstituted or substituted with a halogen group, an aryl group or a heteroaryl group; and R is a methyl group unsubstituted or substituted with a halogen group.

5. The compound of claim 1, wherein L is a direct bond; —O—; an alkylene group; an arylene group; or a heteroarylene group.

6. The compound of claim 1, wherein A is a halogen group; a nitrile group; an ester group; a carboxyl group (—COOH); an alkyl group unsubstituted or substituted with a halogen group; an alkoxy group; or the group of Chemical Formula 3.

7. The compound of claim 1, wherein at least one of R1 R2, R5, and R6 is a substituent of Chemical Formula 2, and the rest in addition to R3 and R4 are the same as or different from each other and each independently hydrogen; an alkyl group unsubstituted or substituted with a halogen group; an aryl group unsubstituted or substituted with one or more selected from the group consisting of a halogen group, an alkyl group substituted with an aryl group, an alkyl group unsubstituted or substituted with a halogen group, the group of Chemical Formula 3, an alkoxy group, an aryl group, and a heteroaryl group unsubstituted or substituted with an aryl group; a heteroaryl group unsubstituted or substituted with an aryl group; or the group of Chemical Formula 3.

8. The compound of claim 1, wherein L2 is a direct bond; —O—; —N(H)—; —OC(=O)—; an alkylene group; an arylene group; or a heteroarylene group.

9. The compound of claim 1, wherein G1 to G6 are the same as or different from each other, and each independently a direct bond; or an alkylene group.

10. The compound of claim 1, wherein any one of Q1 to Q6 is a site bonding to L2 of Chemical Formula 2, and the rest are the same as or different from each other and each independently hydrogen; a halogen group; an alkyl group unsubstituted or substituted with a halogen group; or a dialkylamine group.

11. The compound of claim 1, wherein any one of Q1 to Q6 is a site bonding to L2 of Chemical Formula 2, and adjacent two or more groups among the rest bond to each other to form a heteroring.

12. The compound of claim 1, which has a maximum light emission peak present in 500 nm to 550 nm in a film state.

13. The compound of claim 1, which has a maximum light emission peak present in 600 nm to 650 nm in a film state.

14. The compound of claim 1, which has a maximum light emission peak present in 600 nm to 650 nm in a film state, and a full width at half maximum of the light emission peak is 60 nm or less.

15. The compound of claim 1, which has quantum efficiency of 0.8 or greater.

16. The compound of claim 1, wherein Chemical Formula 1 is selected from among the following compounds:

compound 1-1

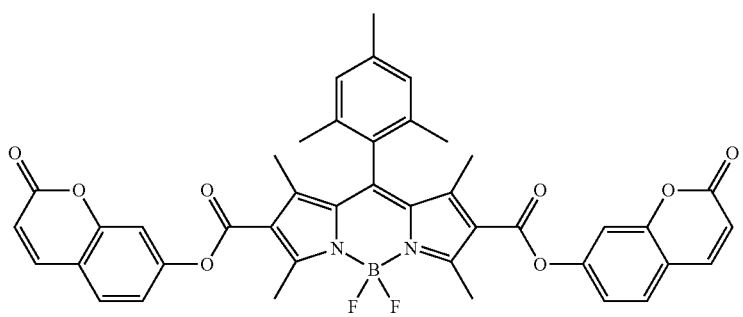

-continued
compound 1-2
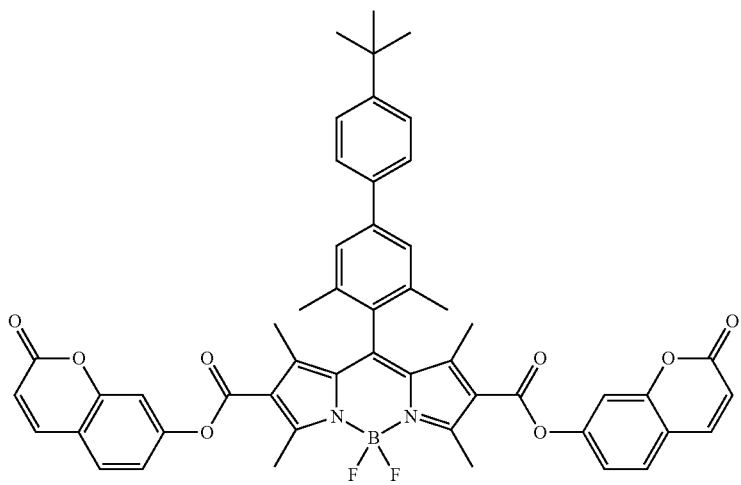
compound 1-3
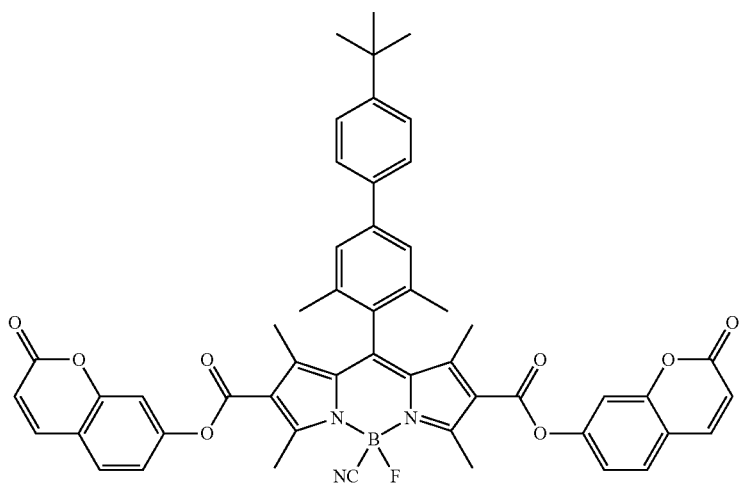
compound 1-4
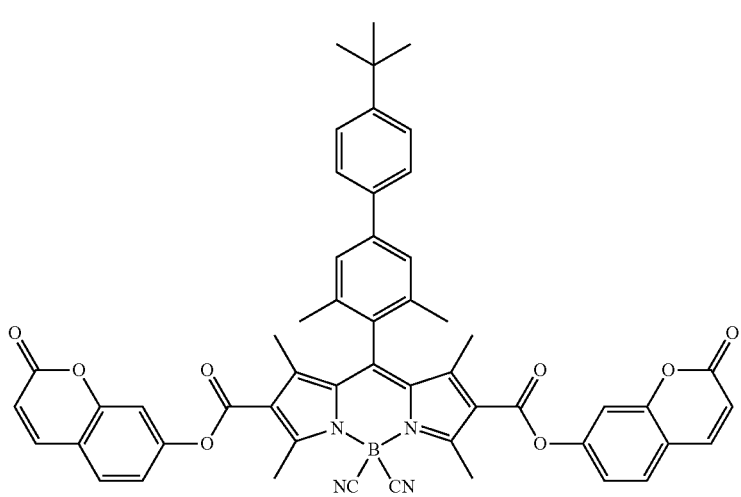

-continued
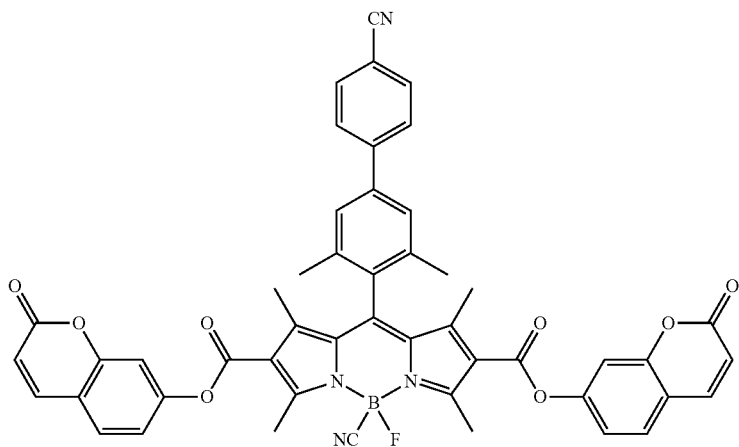
compound 1-5
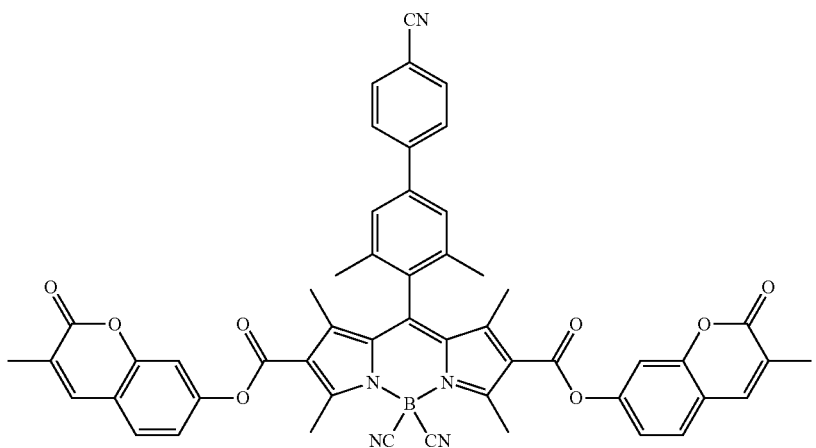
compound 1-6
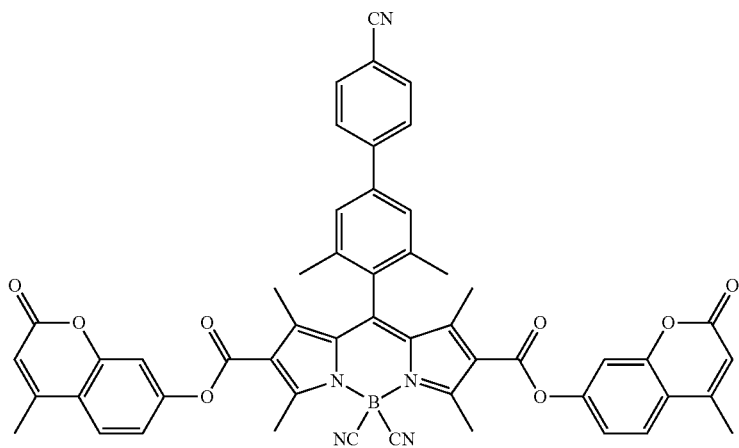
compound 1-7
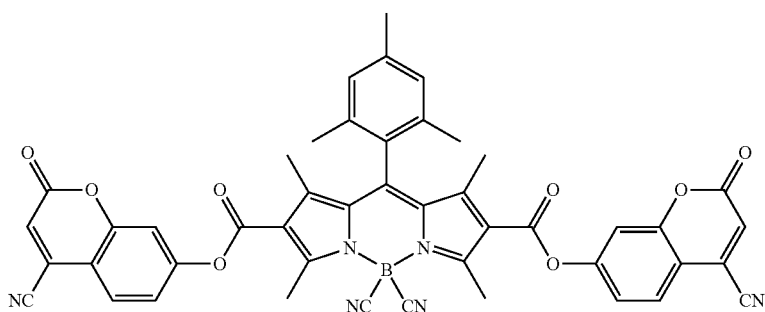
compound 1-8 compound 1-9
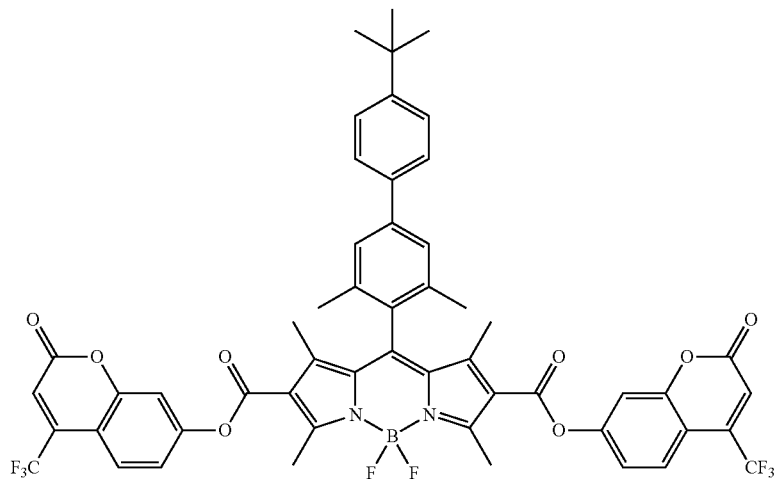
compound 1-10
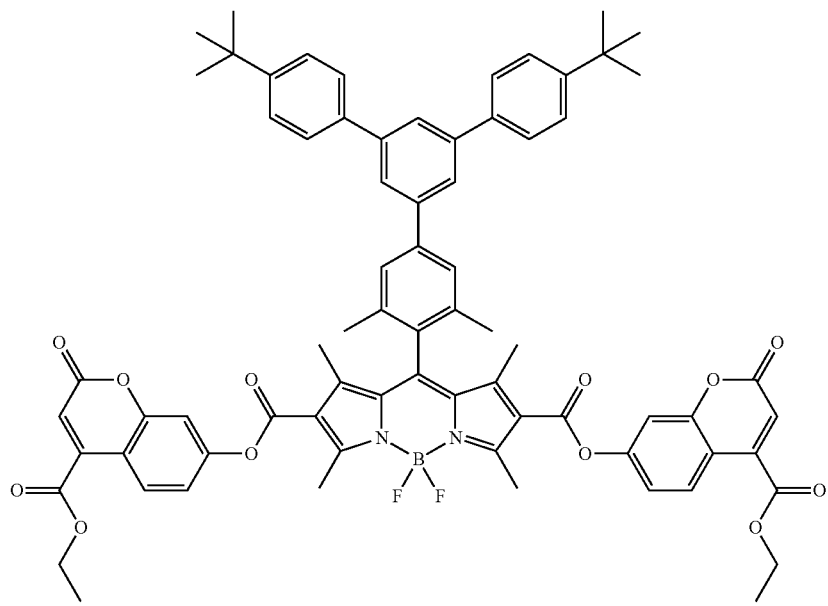
compound 1-11
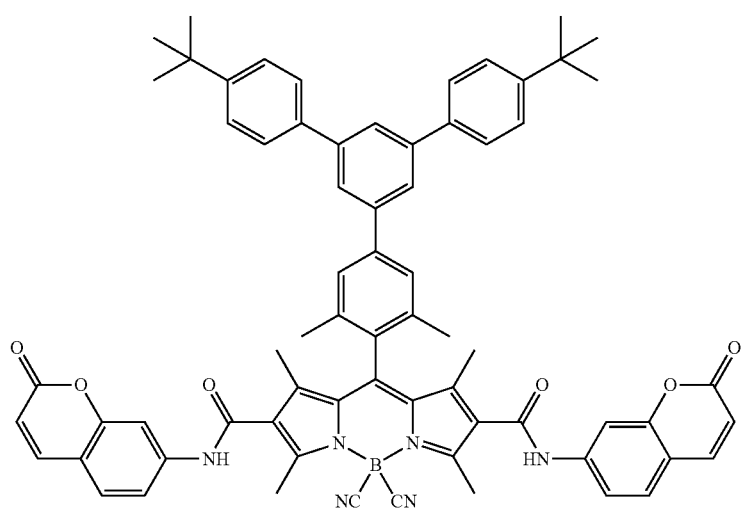

-continued
compound 1-12
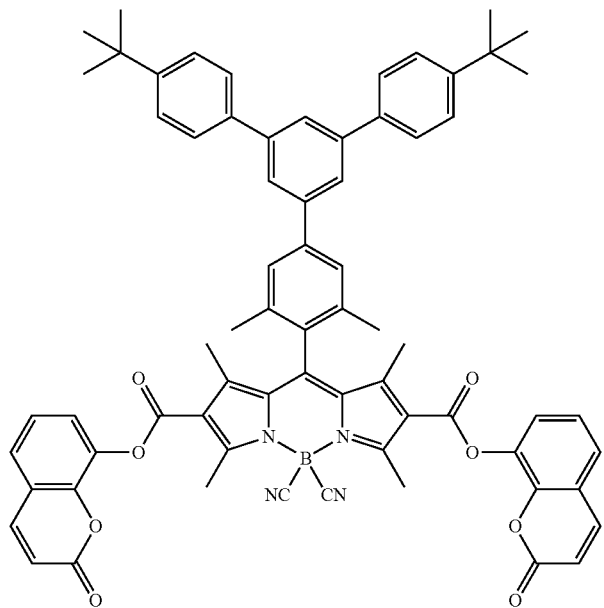
compound 1-13
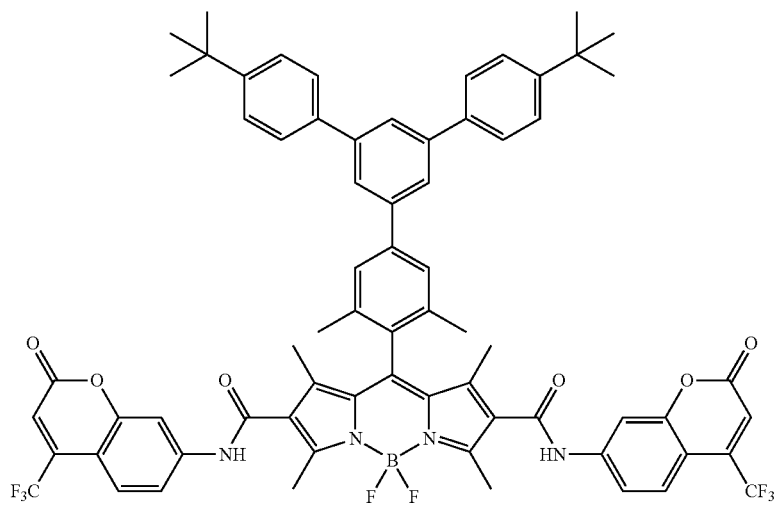
compound 1-14
compound 1-15
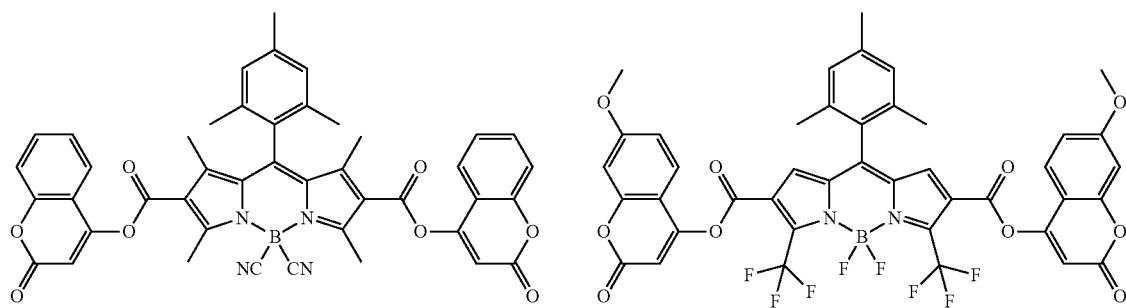

-continued
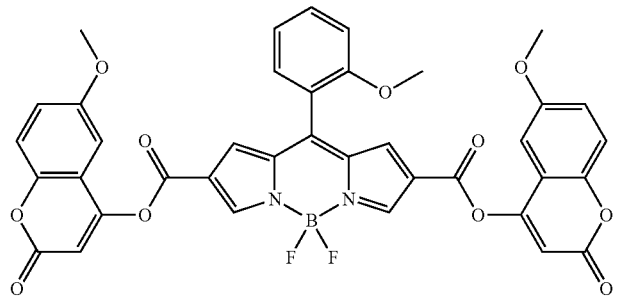
compound 1-16
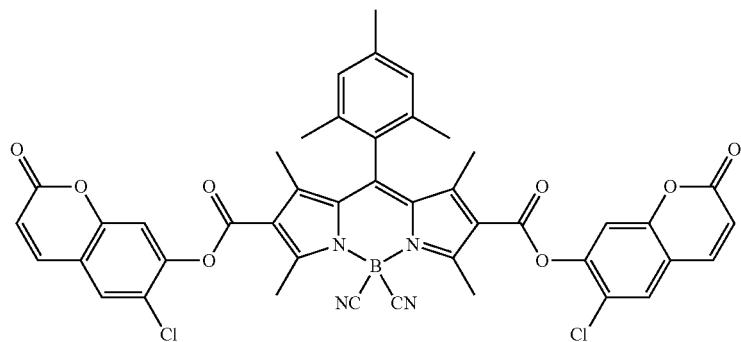
compound 1-17
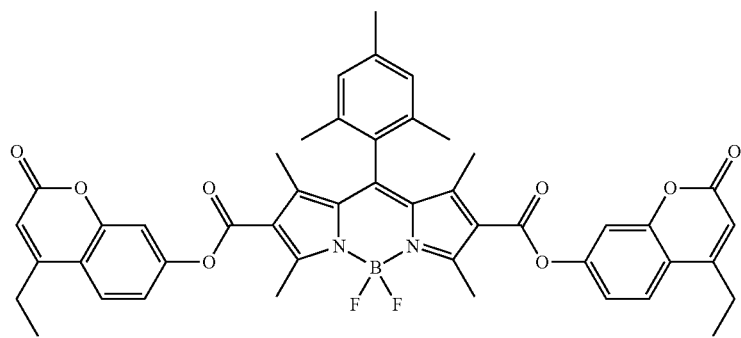
compound 1-18
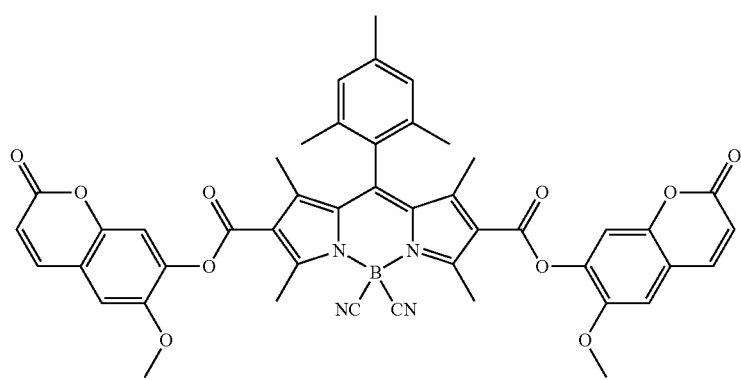
compound 1-19

-continued
compound 1-20
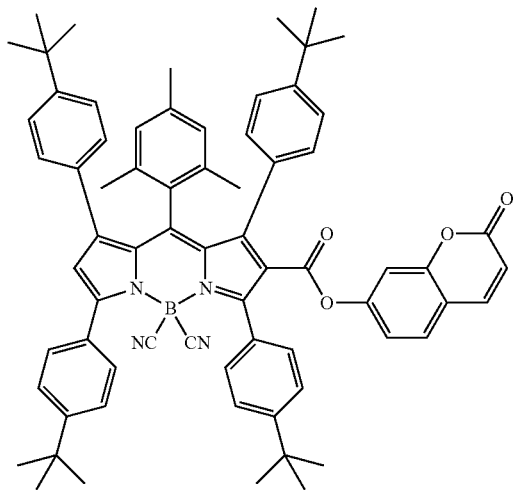
compound 1-21
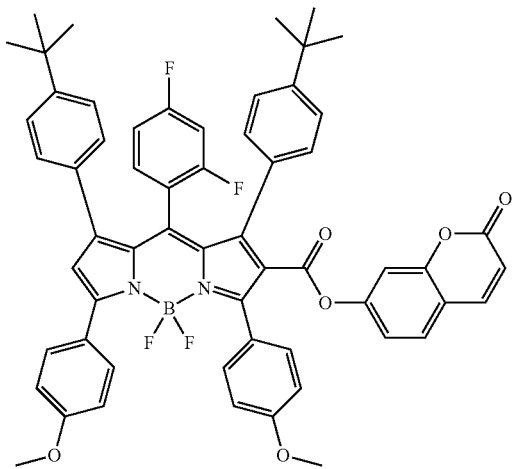
compound 1-22
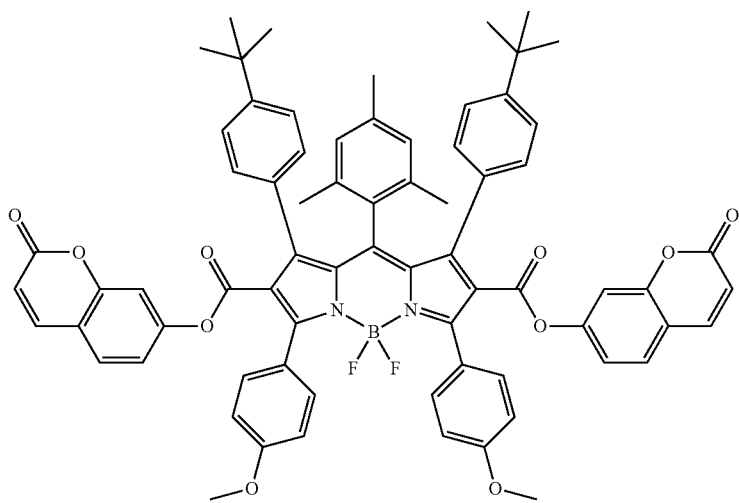
compound 1-23
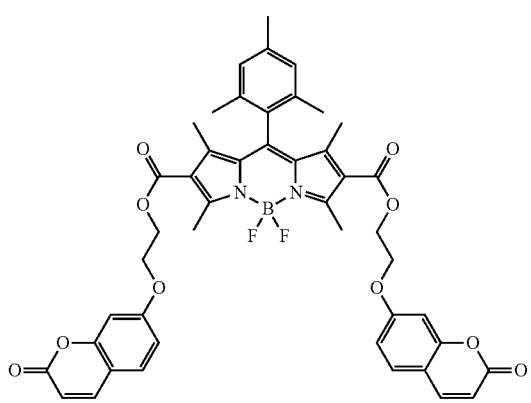
compound 1-24
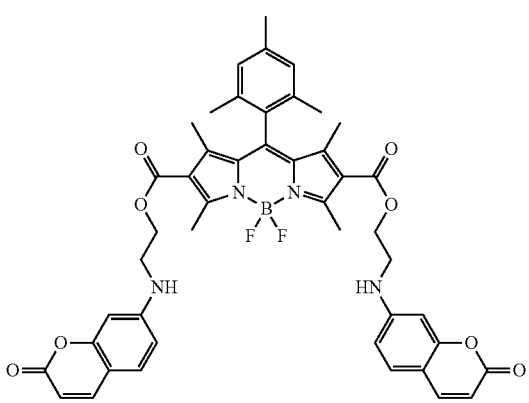

-continued
compound 1-25
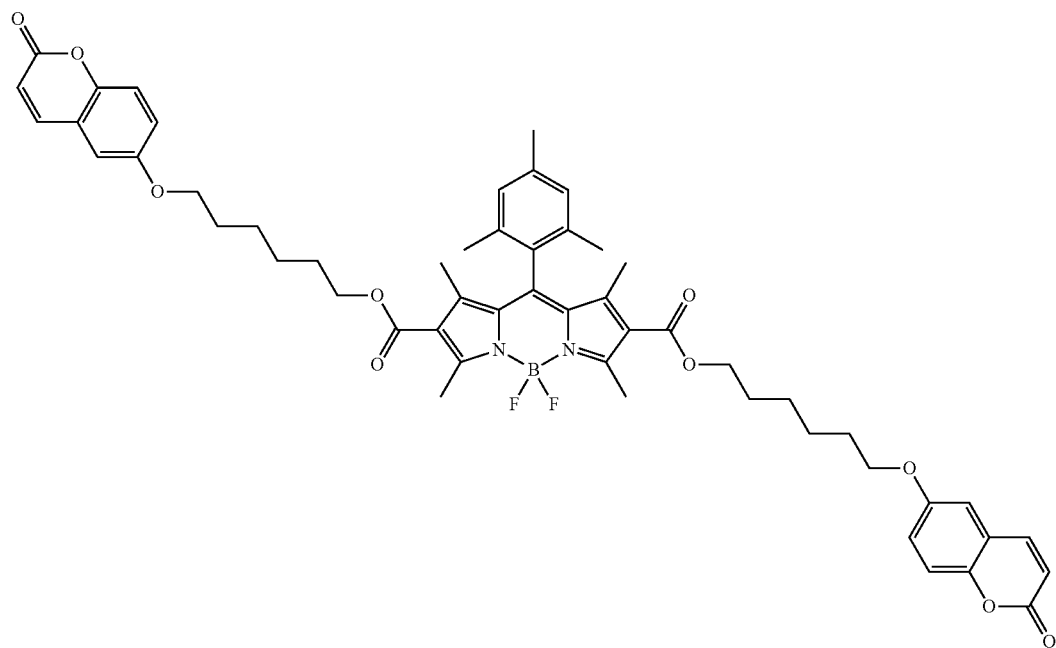
compound 1-26
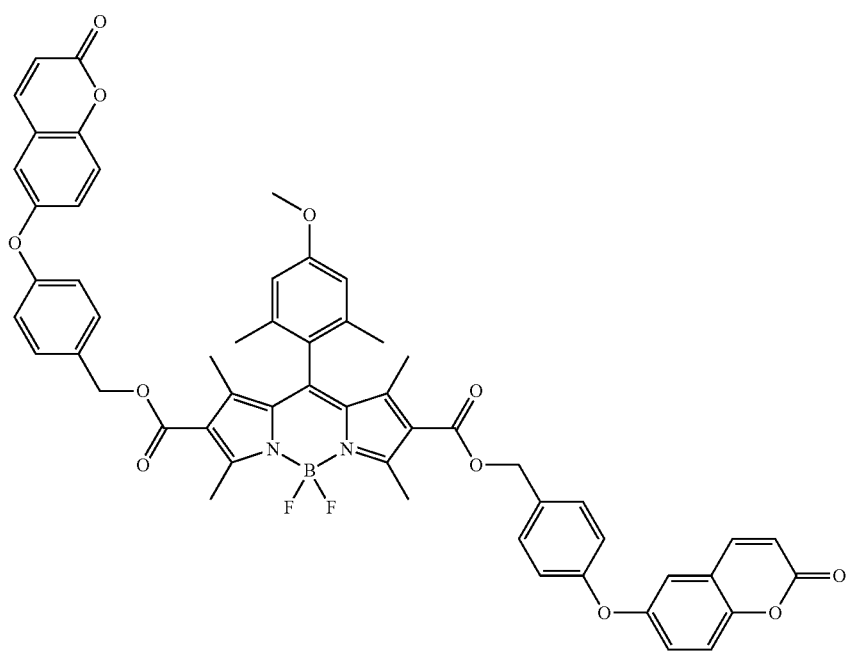

-continued
compound 1-27
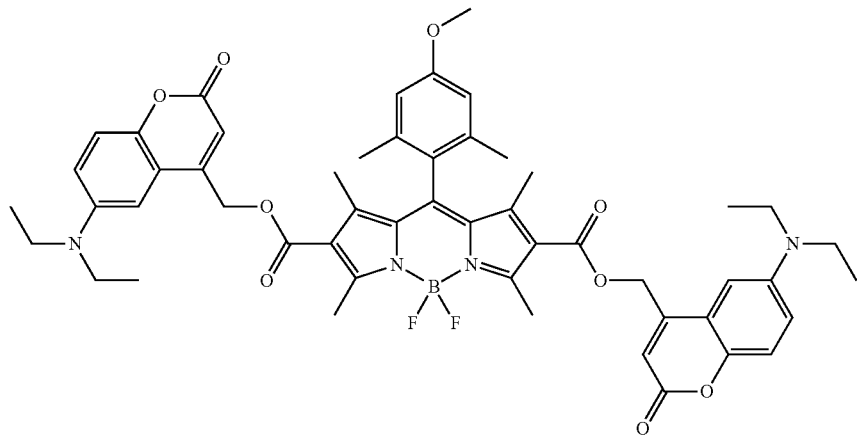
compound 1-28
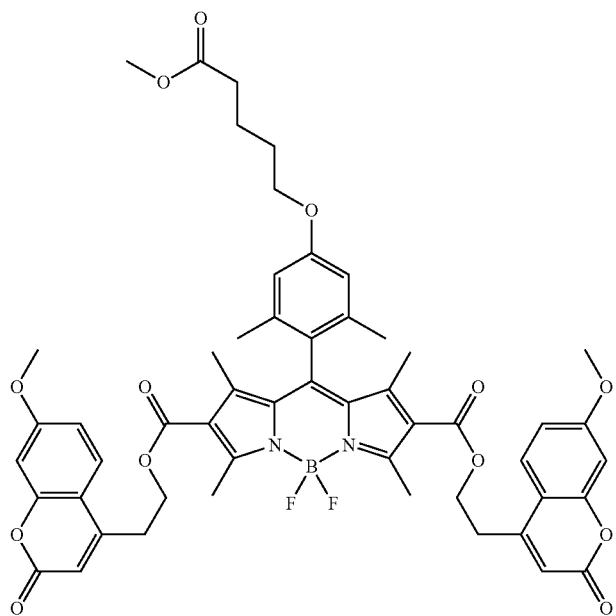
compound 1-29
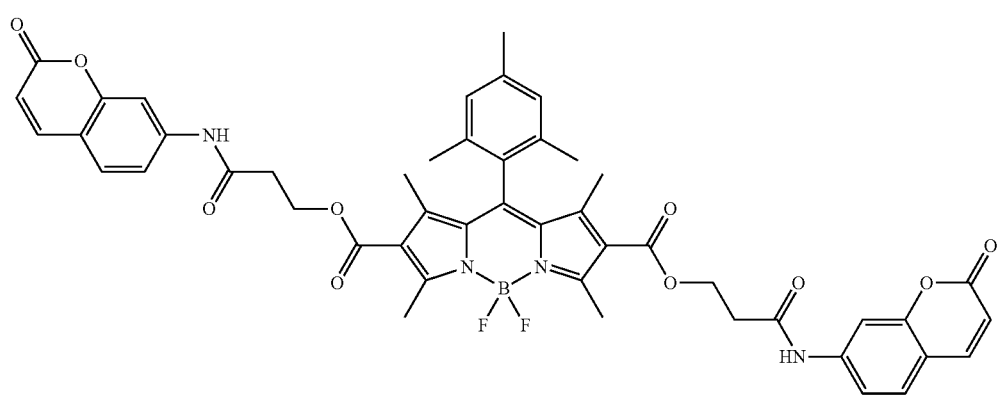

compound 1-30
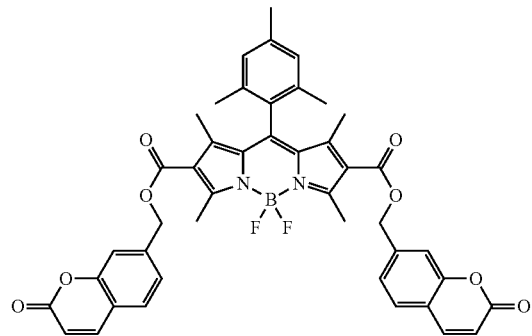
compound 1-31
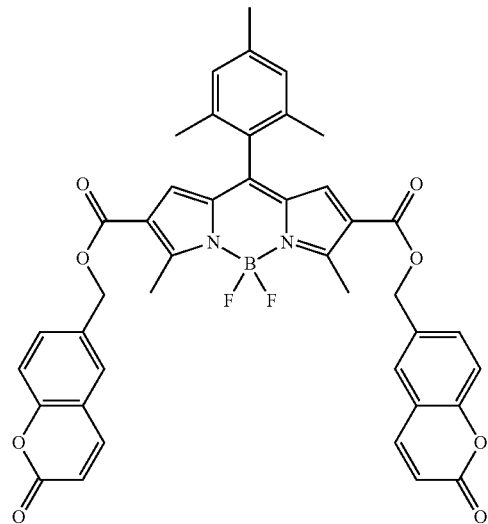
compound 1-32
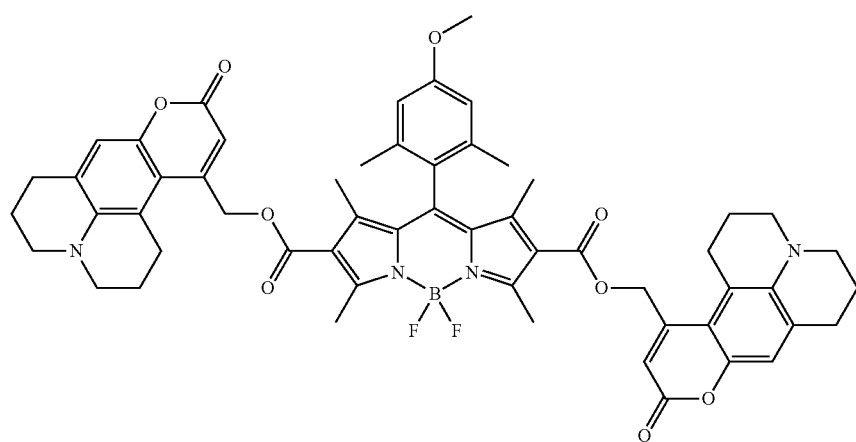
compound 1-33
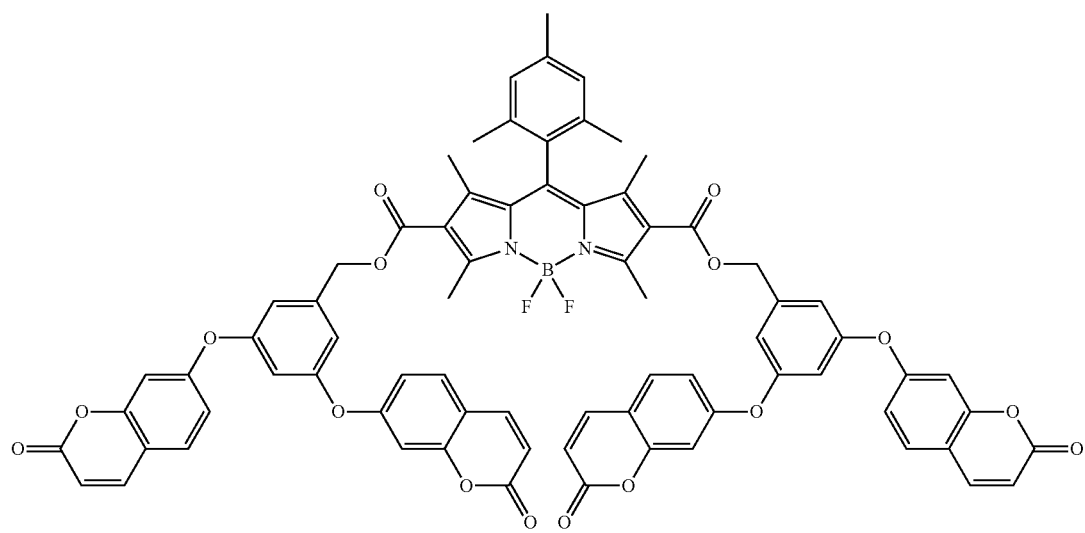

-continued
compound 1-34
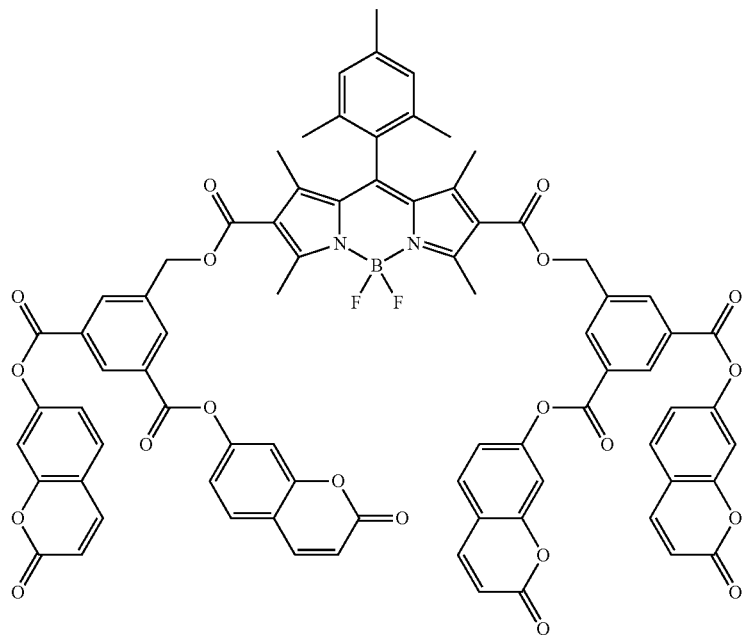
compound 1-35
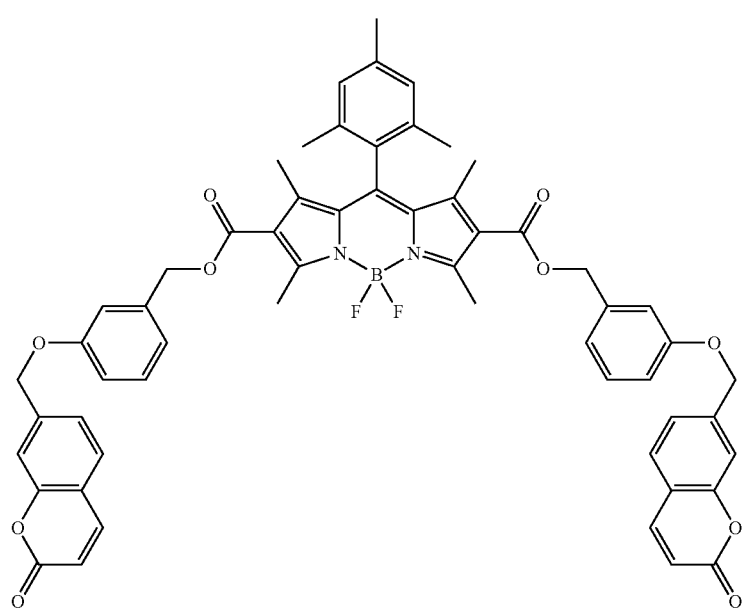

-continued
compound 1-36
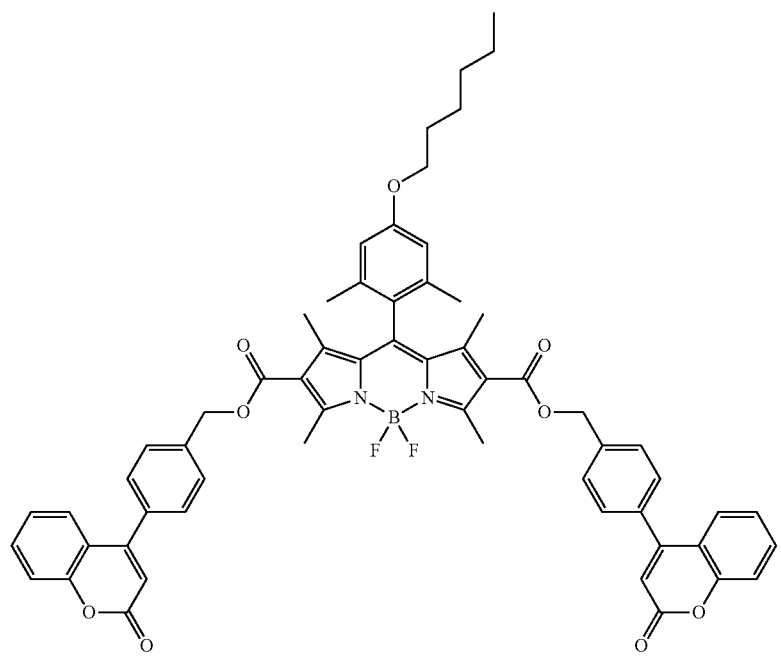
compound 1-37
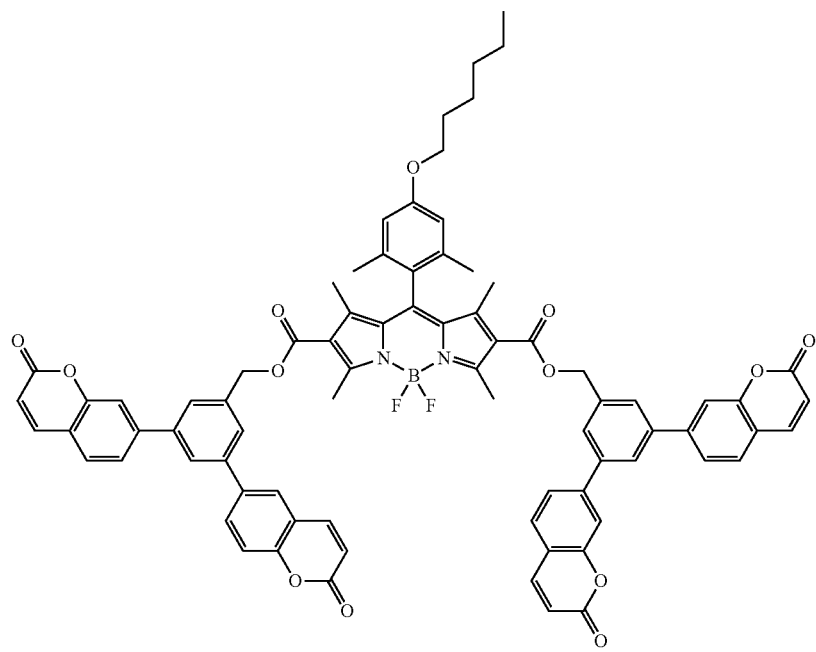

compound 1-38
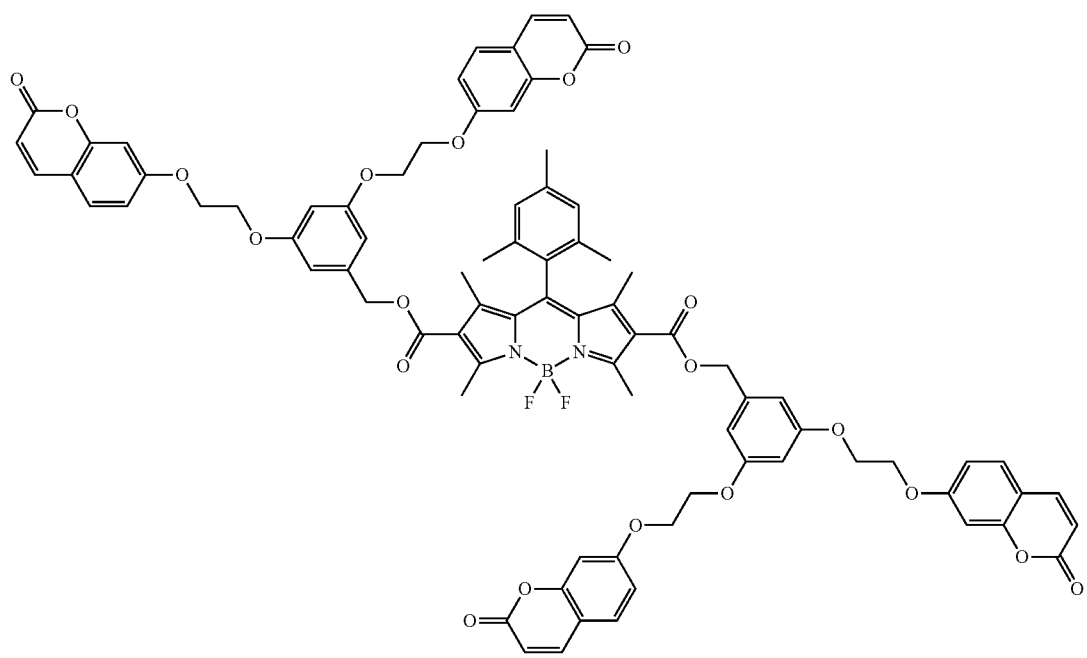
compound 1-39
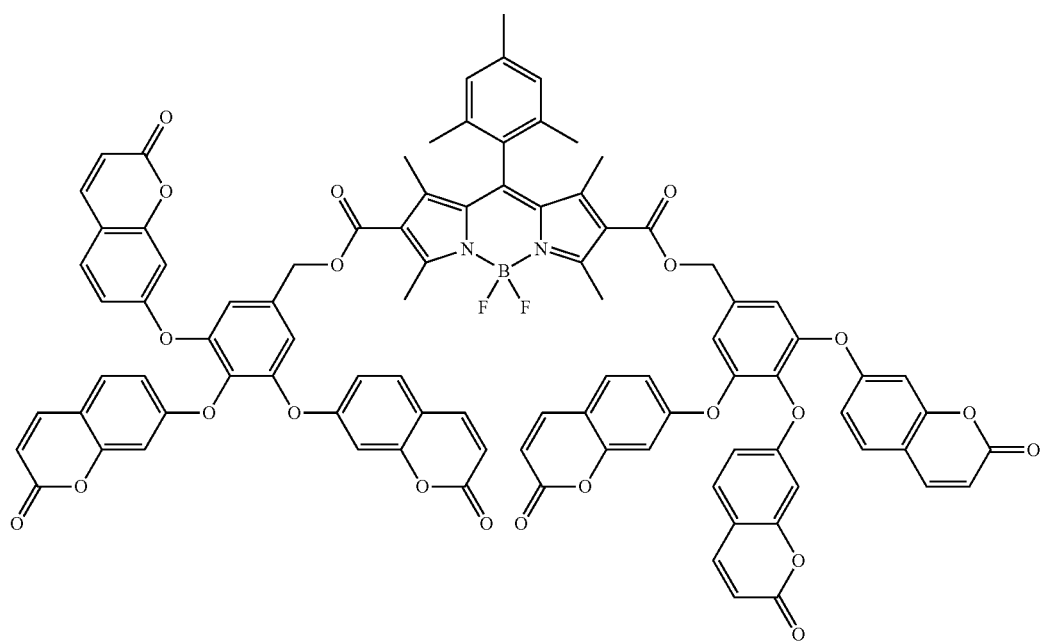

-continued
compound 1-40
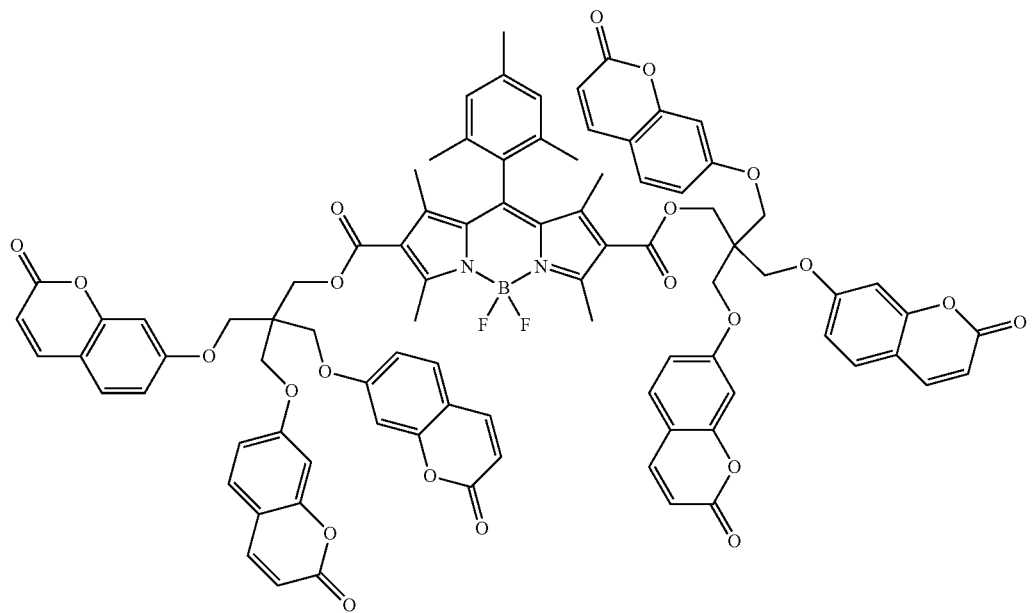
compound 1-41
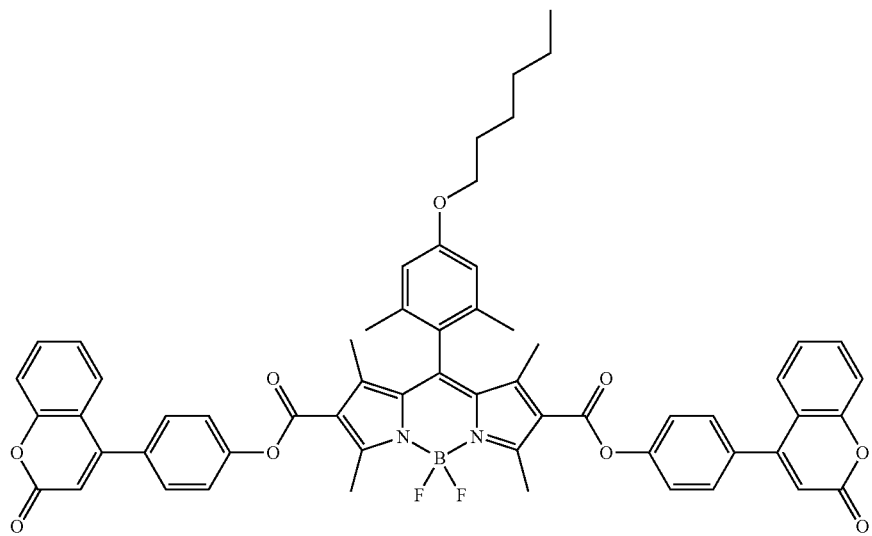
compound 1-42
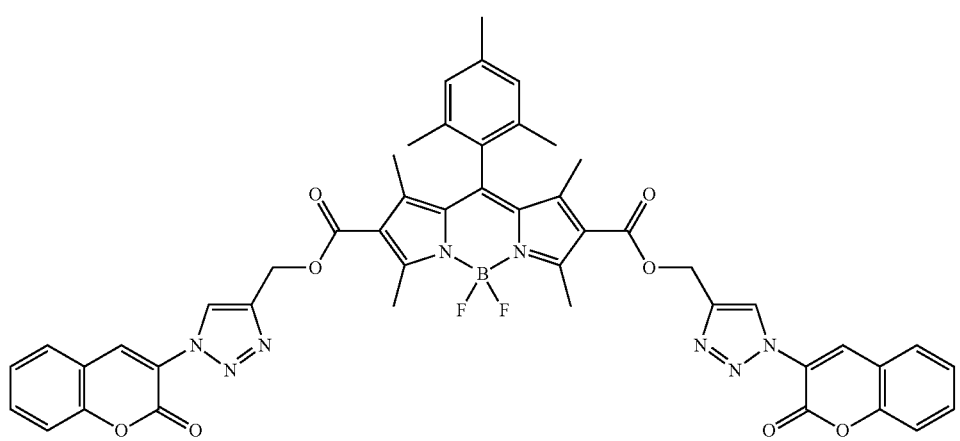

compound 1-43
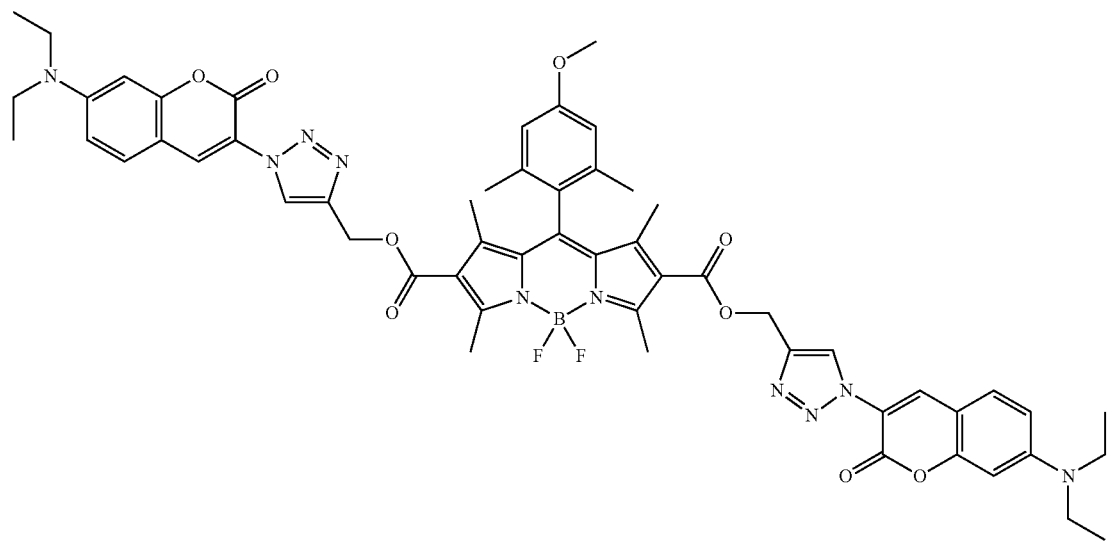
compound 1-44
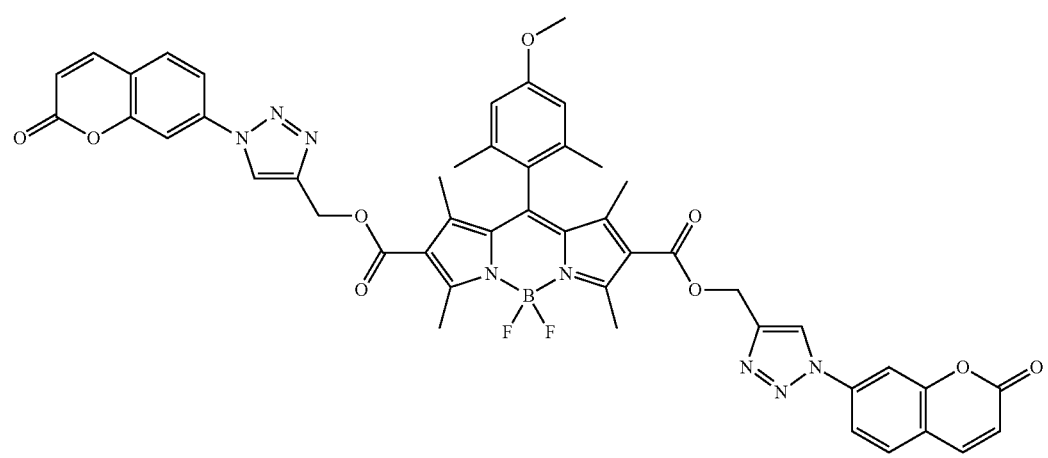
compound 1-45
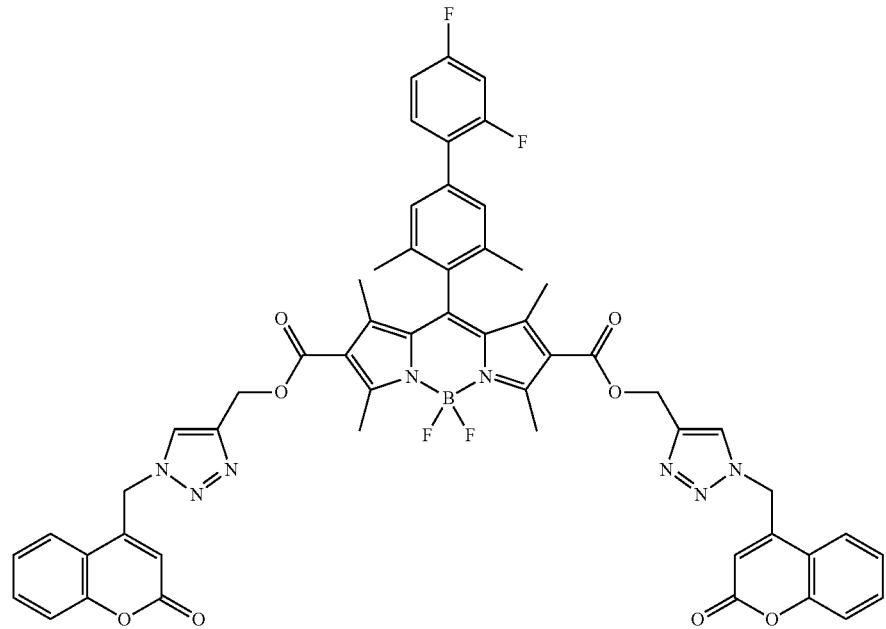

compound 1-46
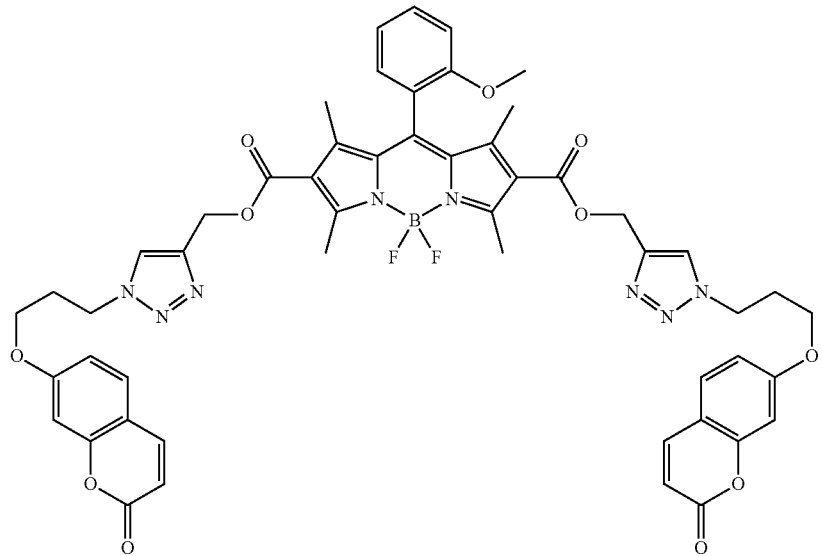
compound 1-47
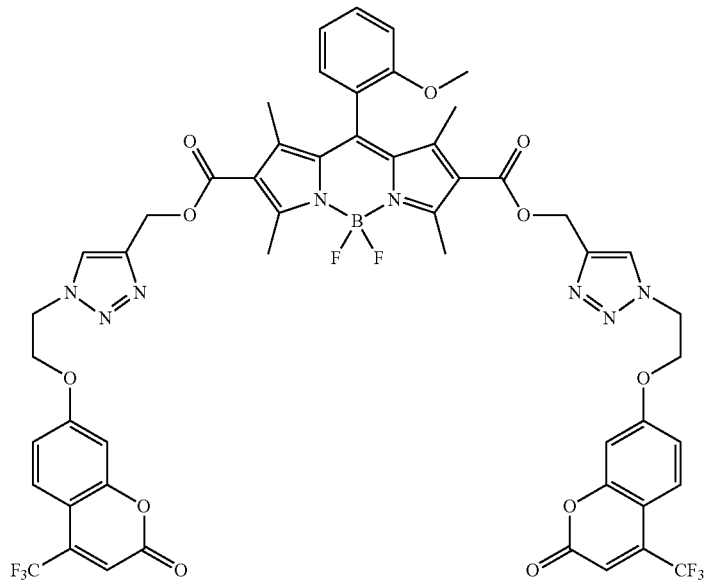
compound 1-48
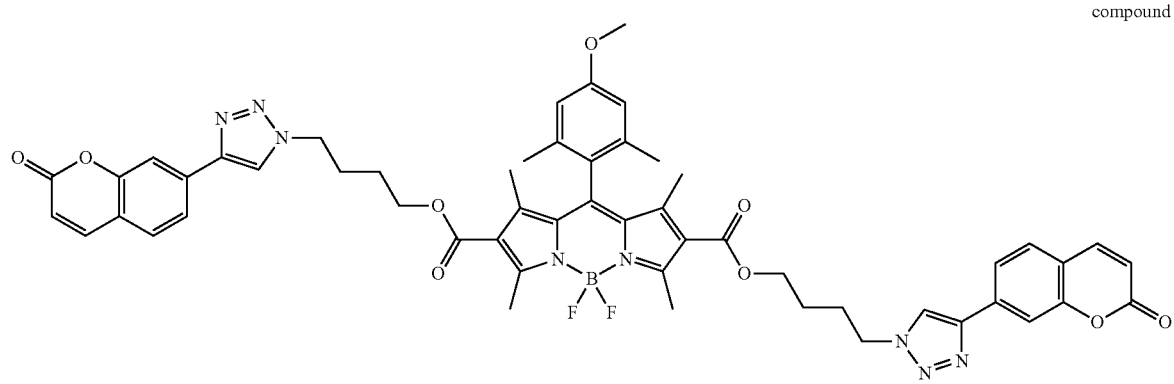

-continued
compound 1-49
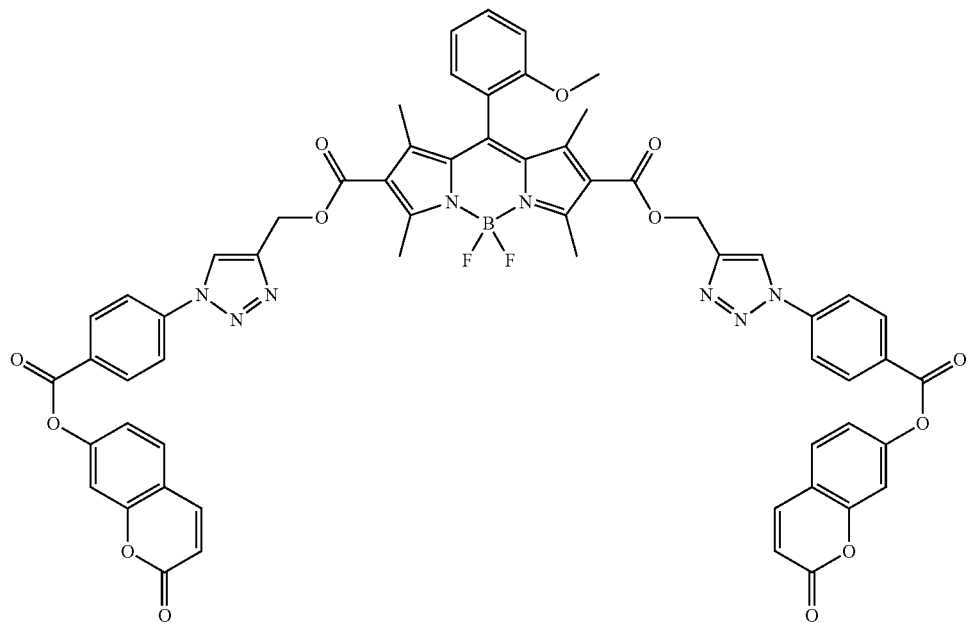
compound 1-50
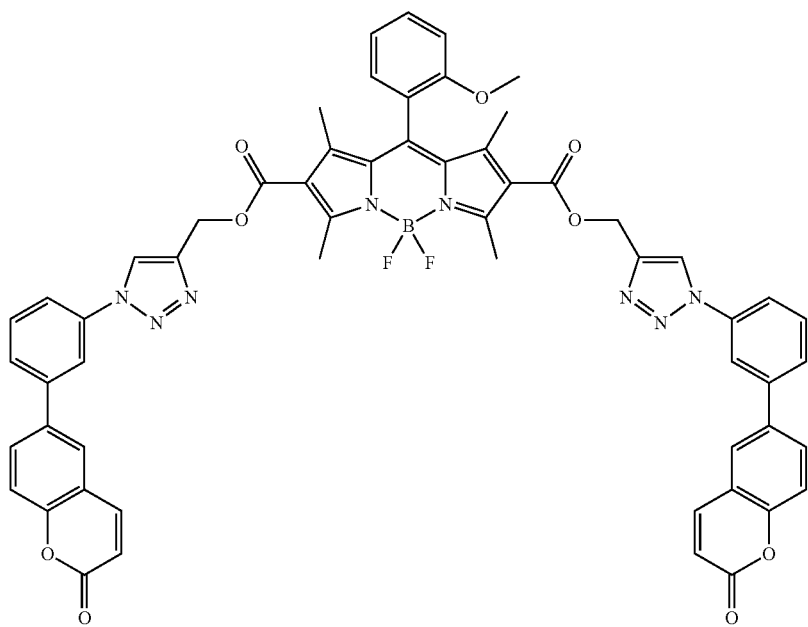

compound 1-51
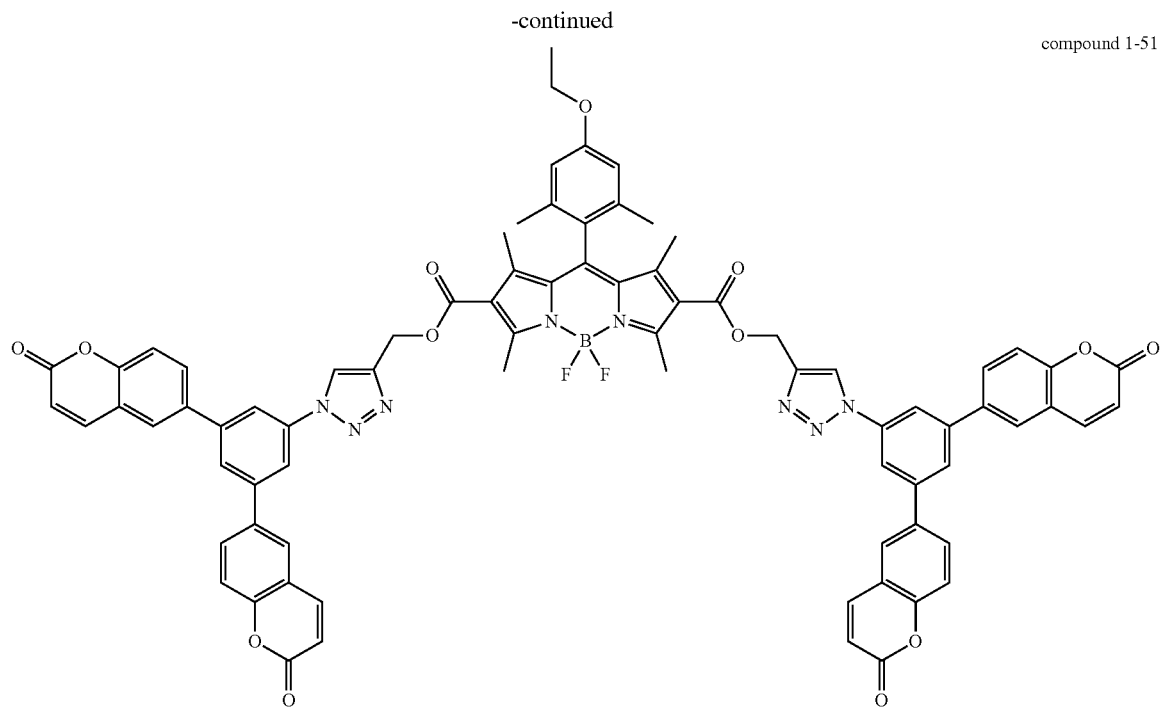
compound 1-52
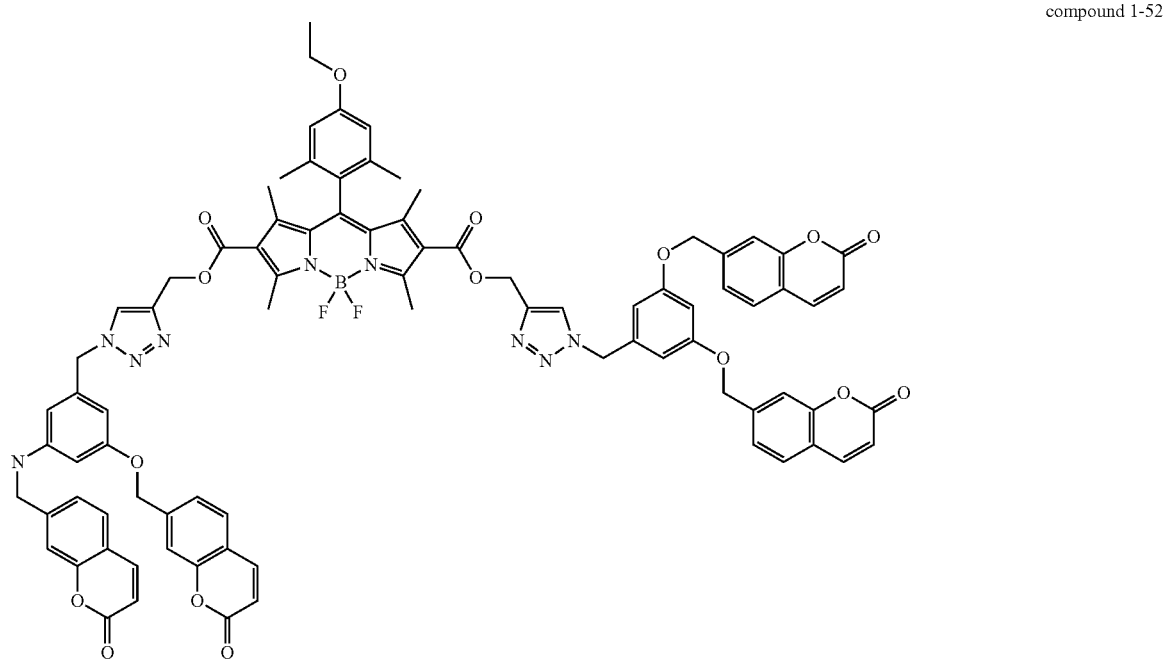

compound 1-53
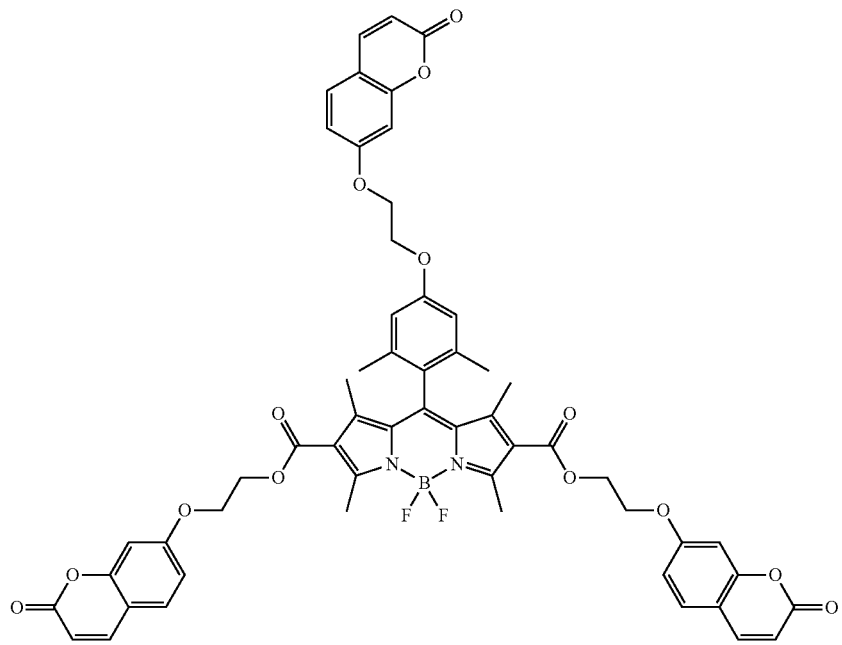
compound 1-54
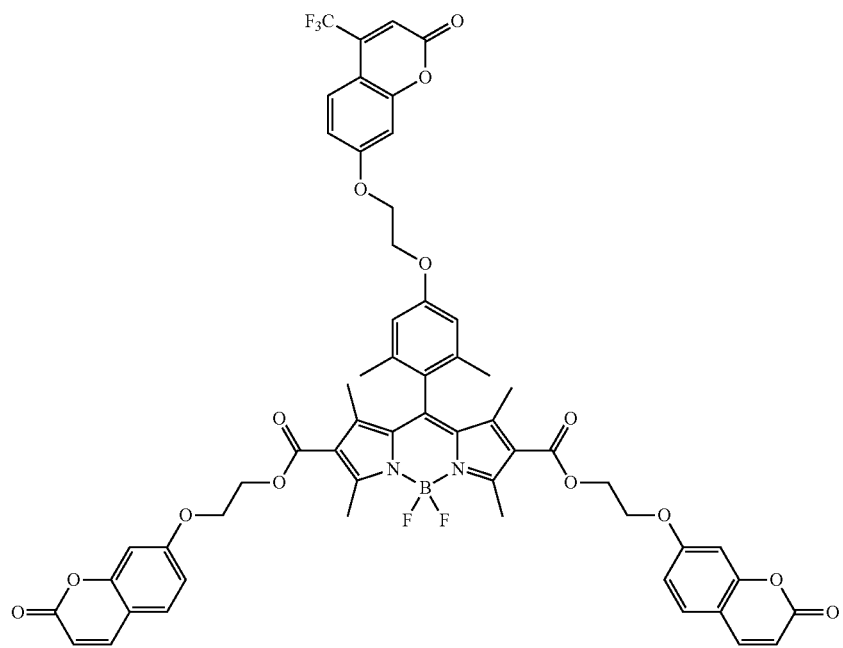

compound 1-55
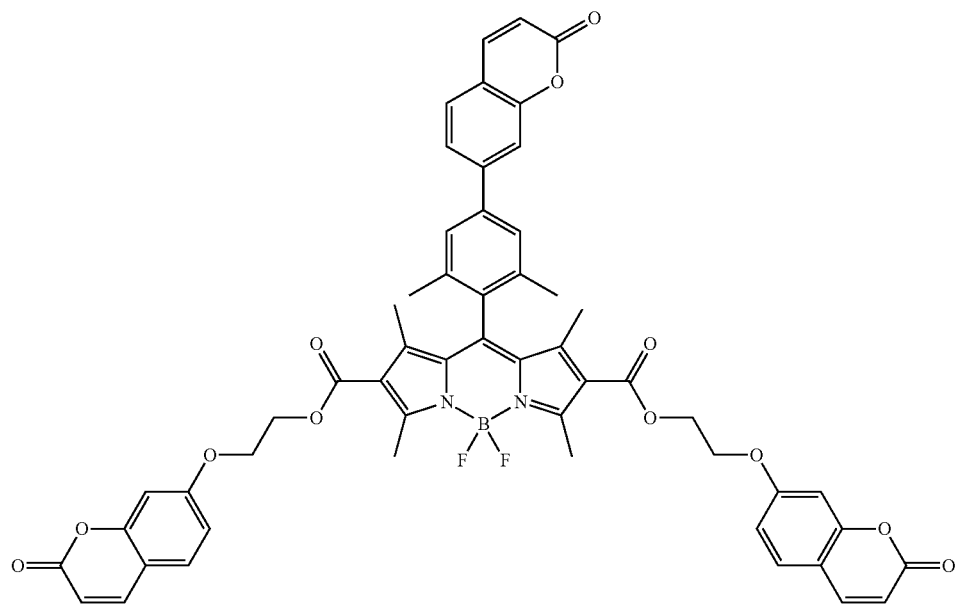
compound 1-56
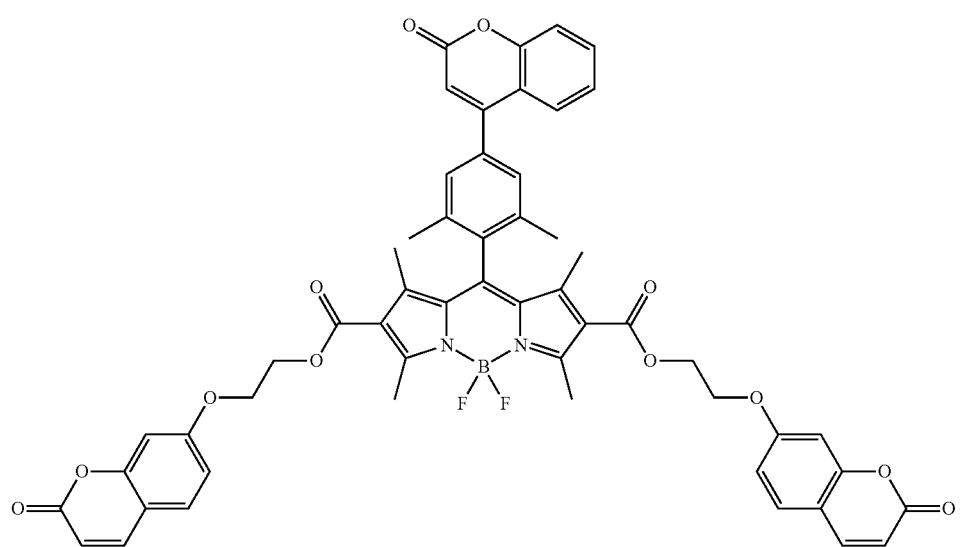

compound 1-57
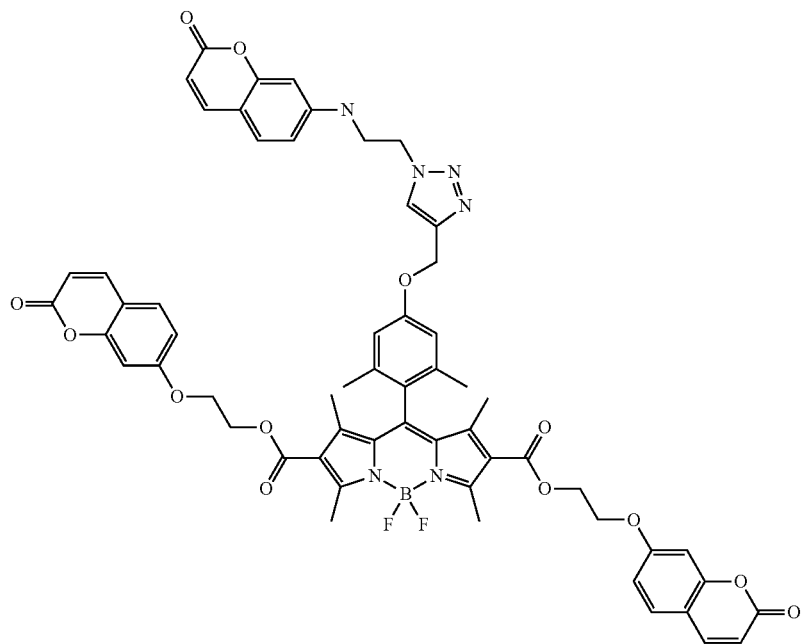
compound 1-58
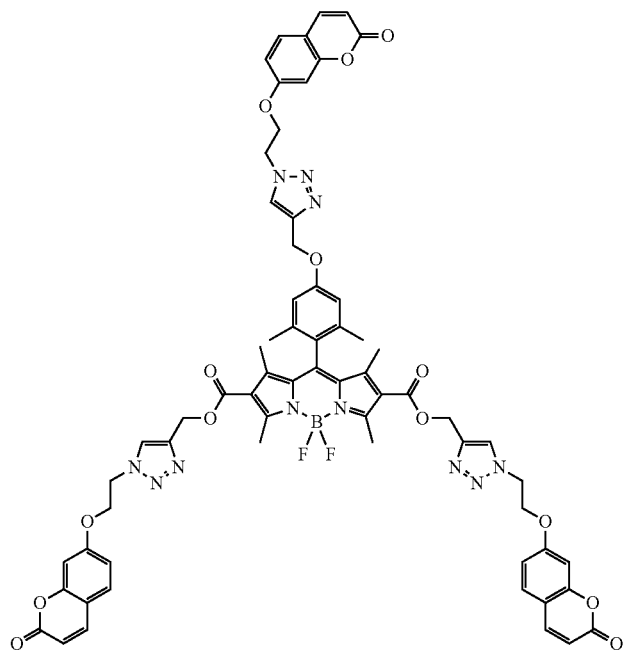

-continued
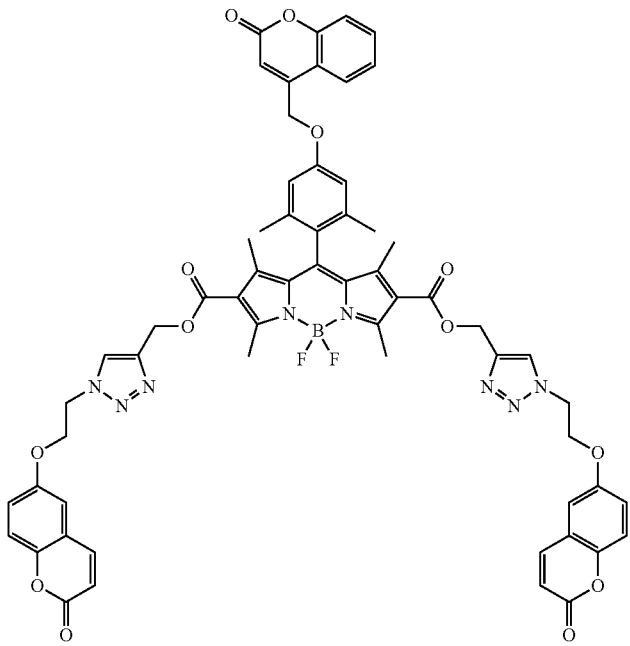
compound 1-59
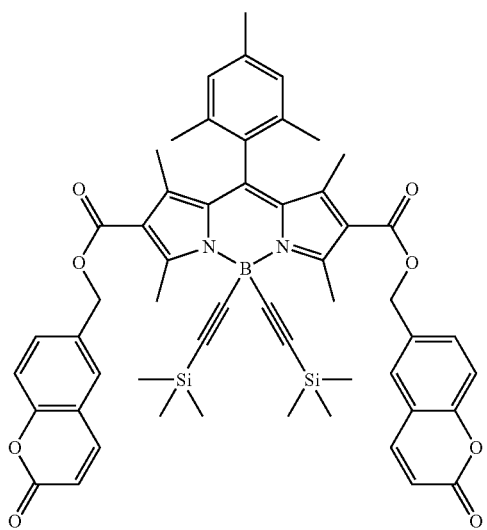
compound 1-60
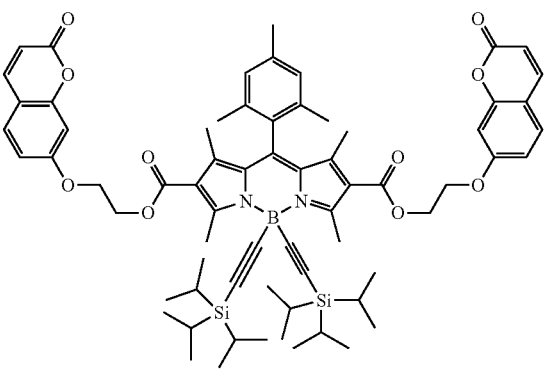
compound 1-61
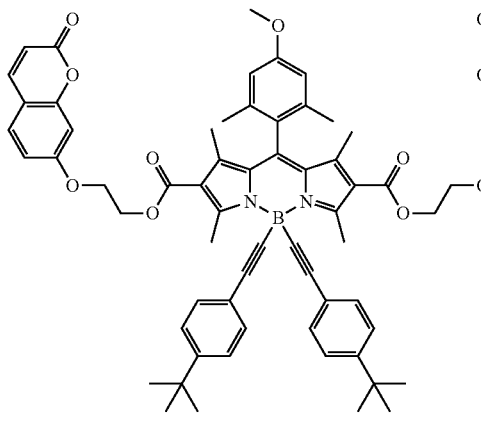
compound 1-62
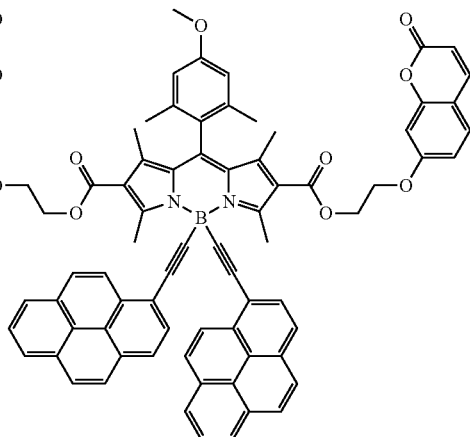
compound 1-63 compound 1-64
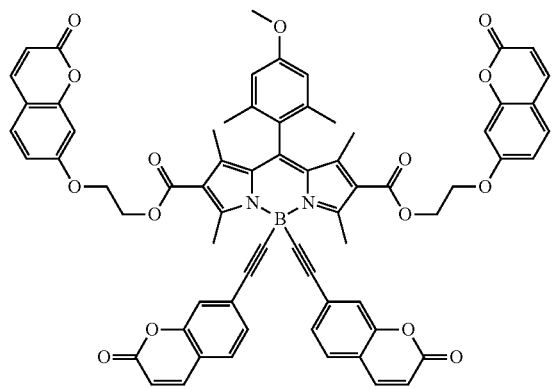
compound 1-65
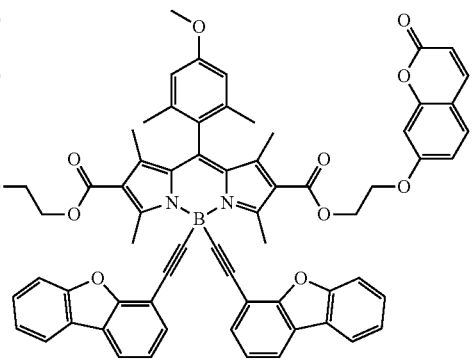
compound 1-66
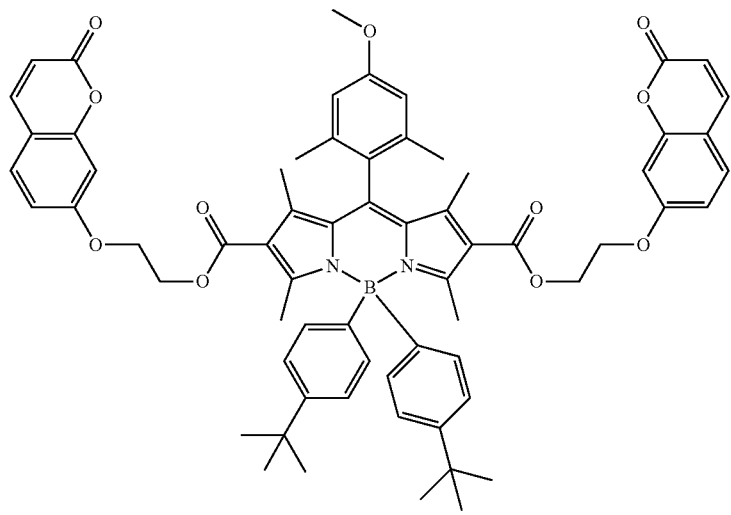
compound 1-67
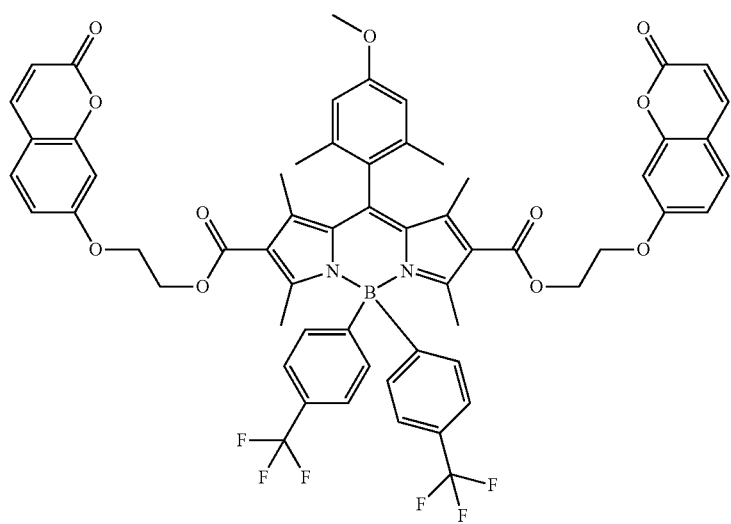

-continued
compound 1-68
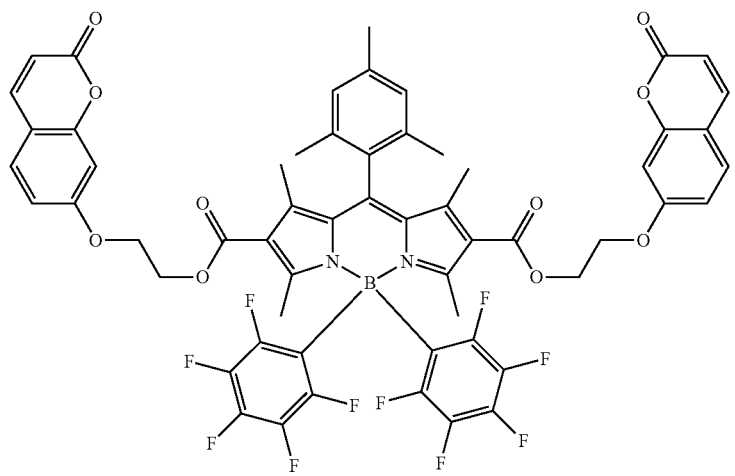
compound 1-69
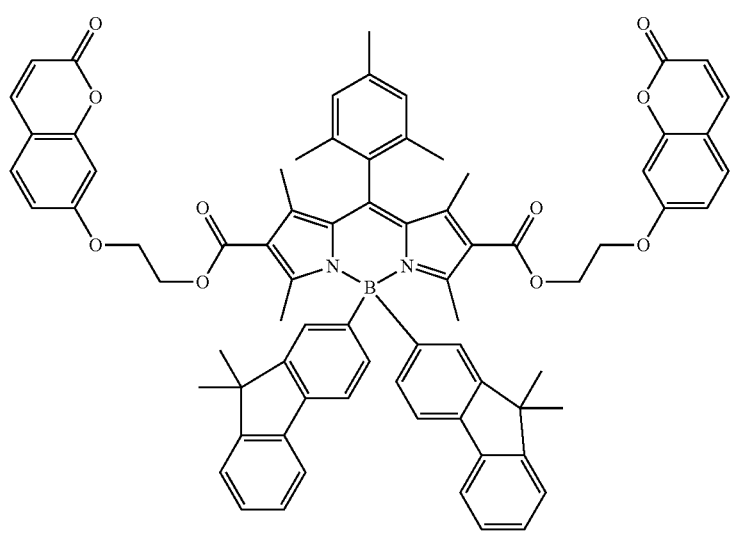
compound 1-70
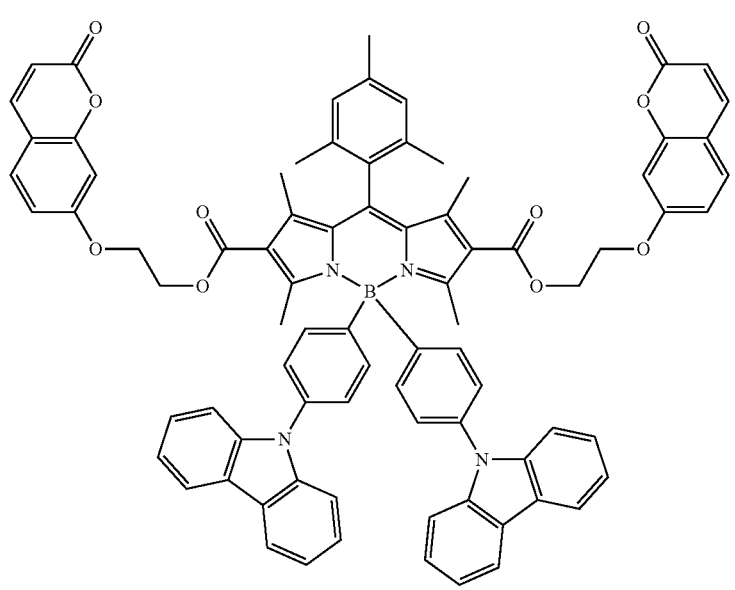

compound 1-71
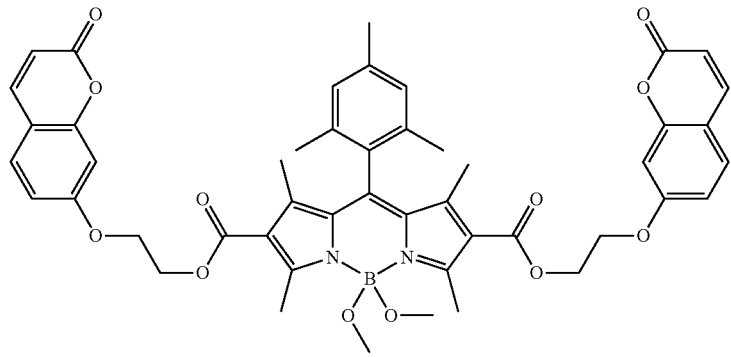
compound 1-72
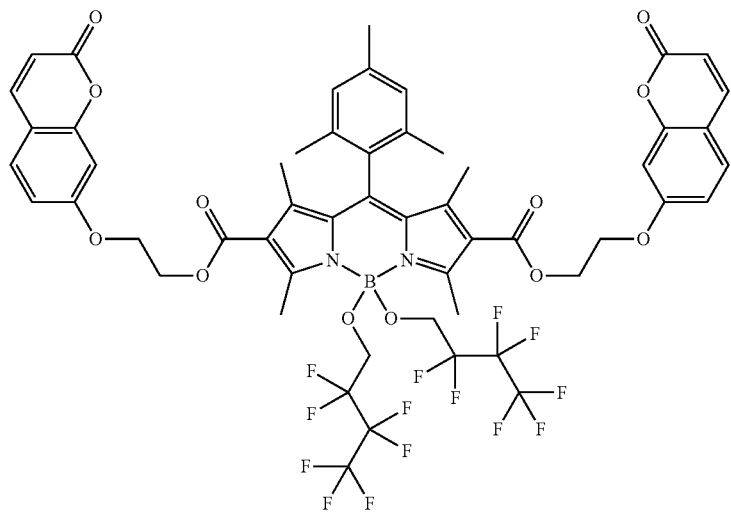
compound 1-73
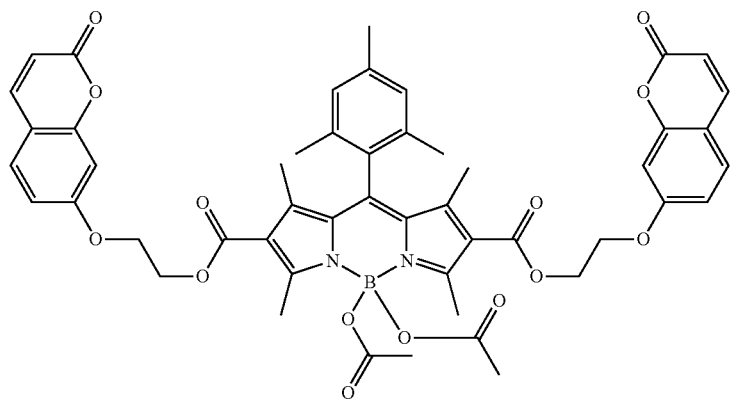

-continued
compound 1-74
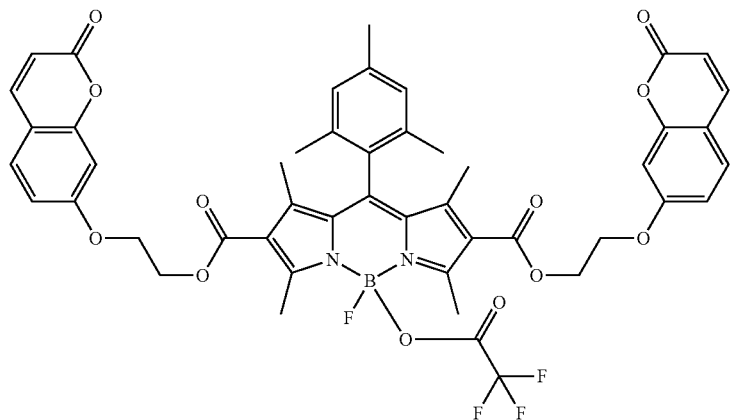
compound 1-75
compound 1-76
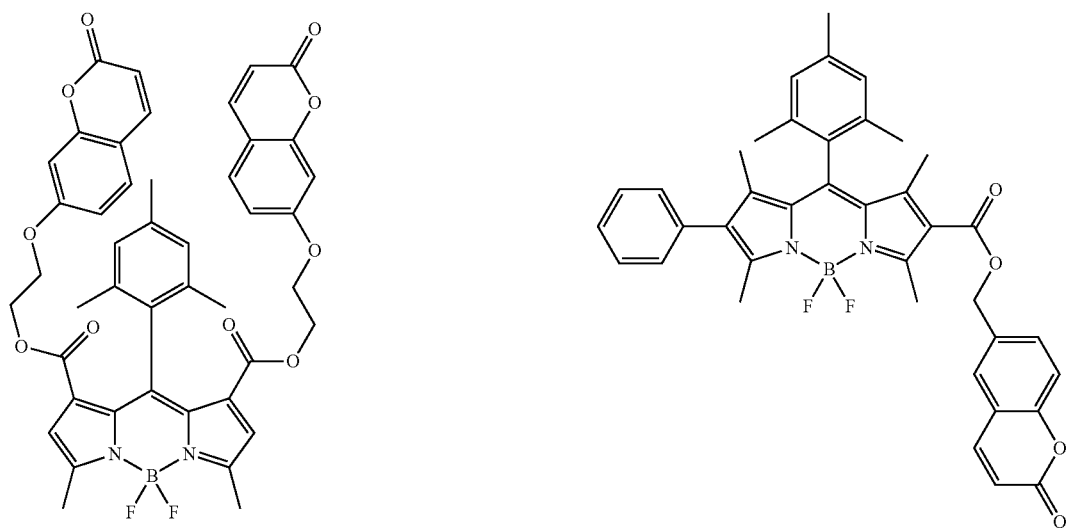
compound 1-77
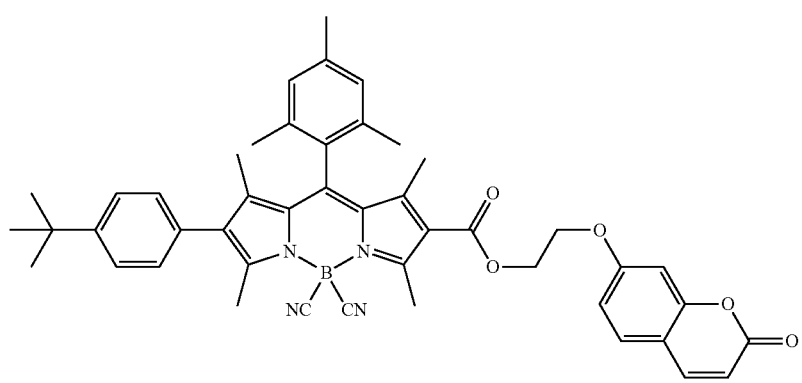

-continued
compound 1-78
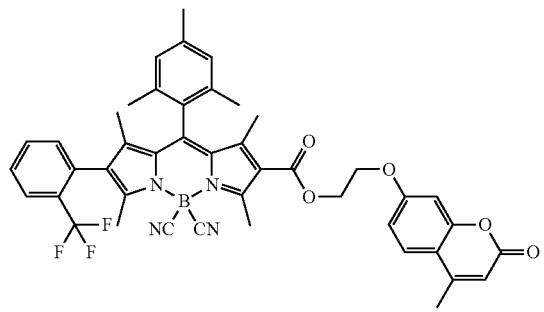
compound 1-79
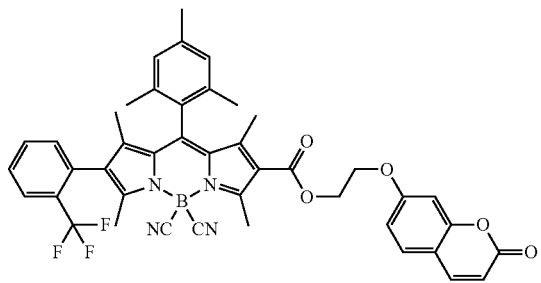
compound 1-80
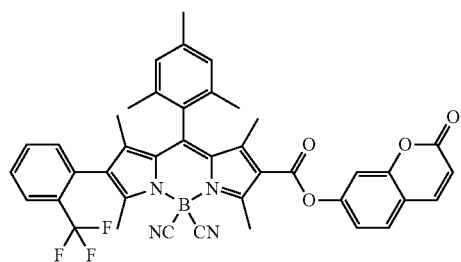
compound 1-81
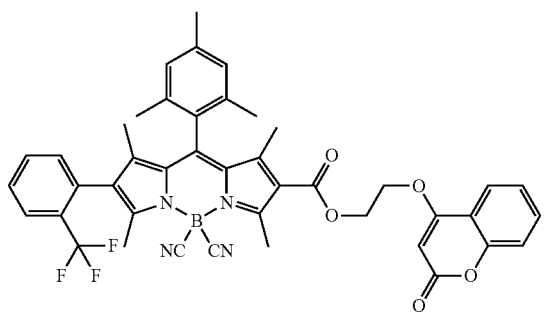
compound 1-82
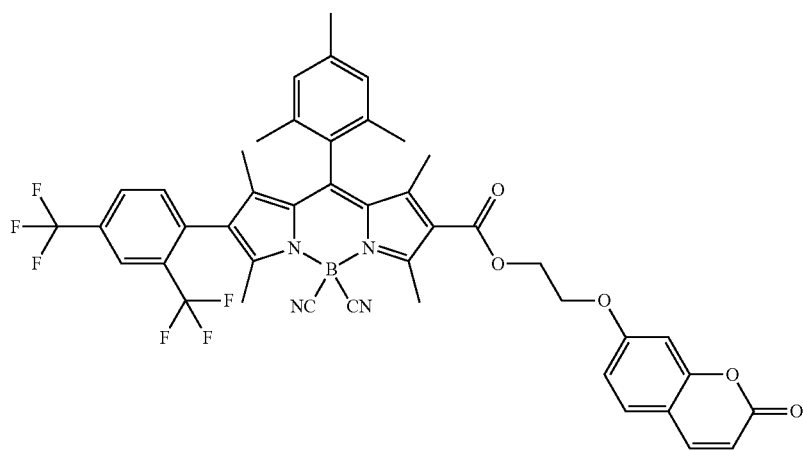
compound 1-83
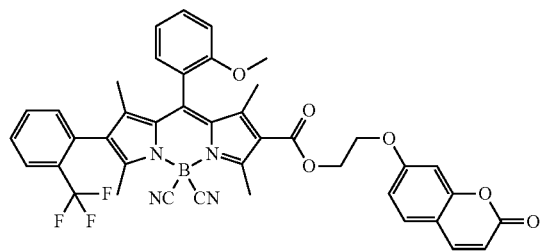
compound 1-84
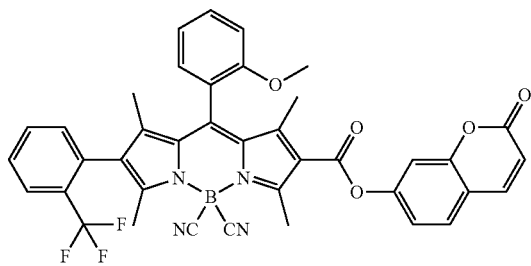

-continued
compound 1-85
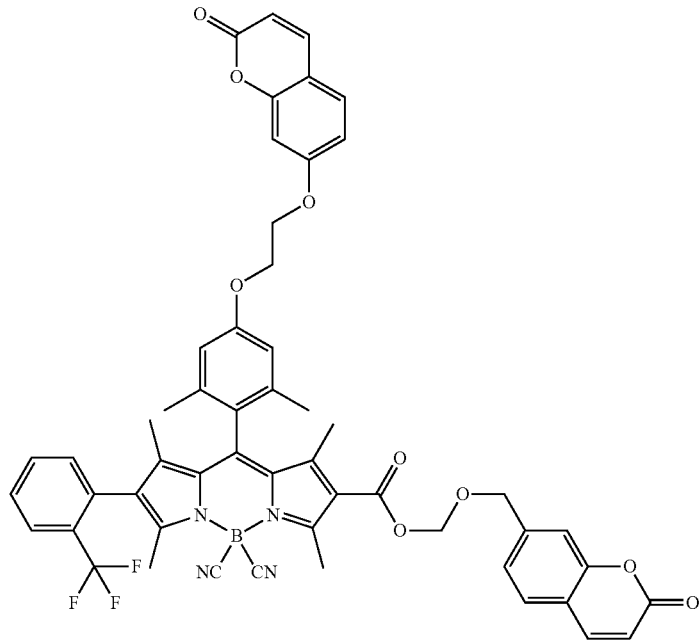
compound 1-86
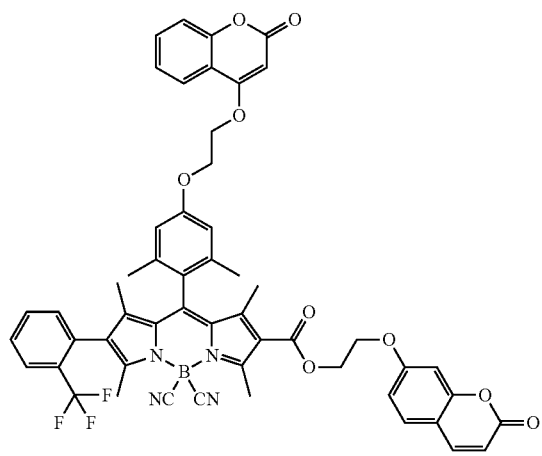
compound 1-87
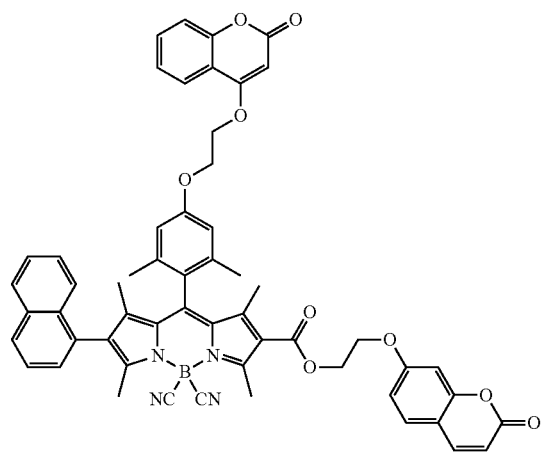
compound 1-88
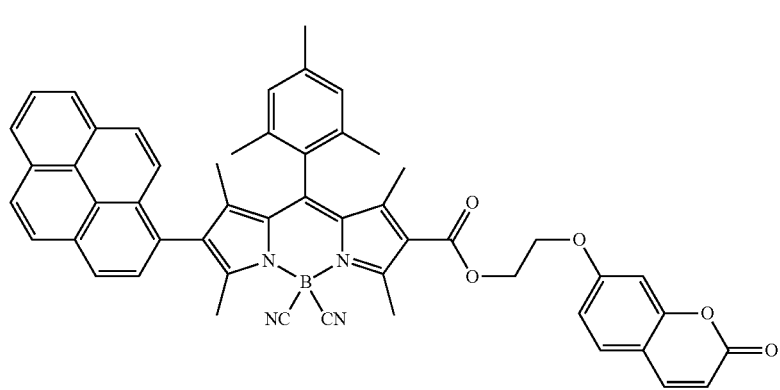

-continued
compound 1-89
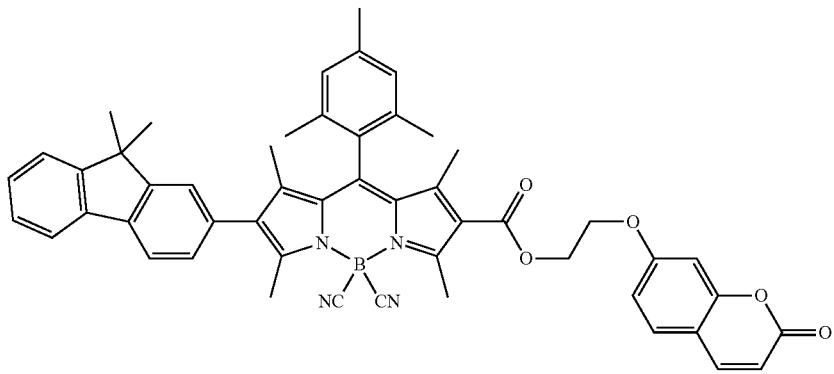
compound 1-90
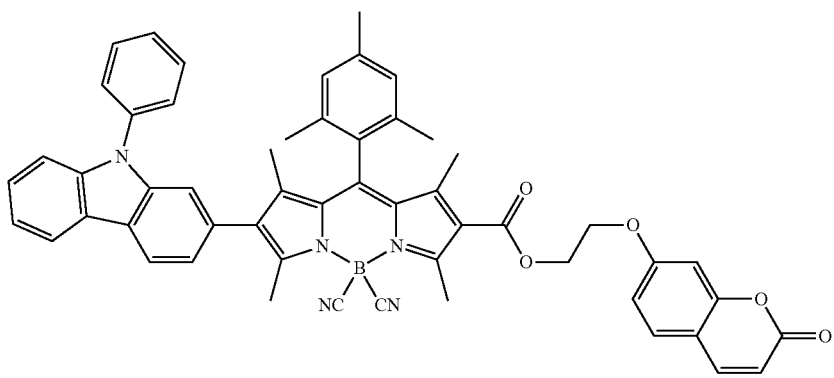
compound 1-91
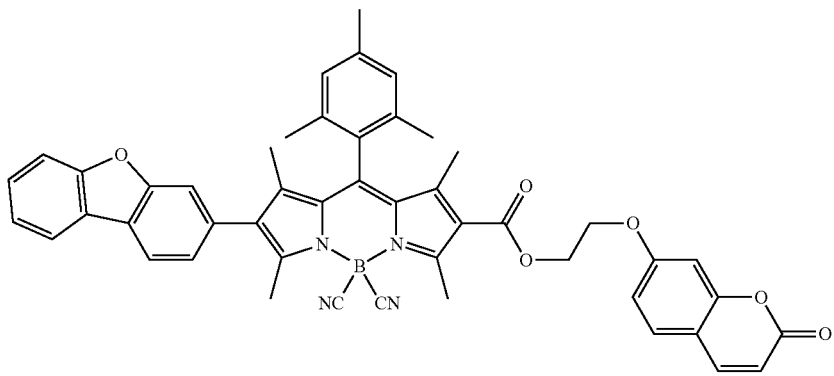
compound 1-92
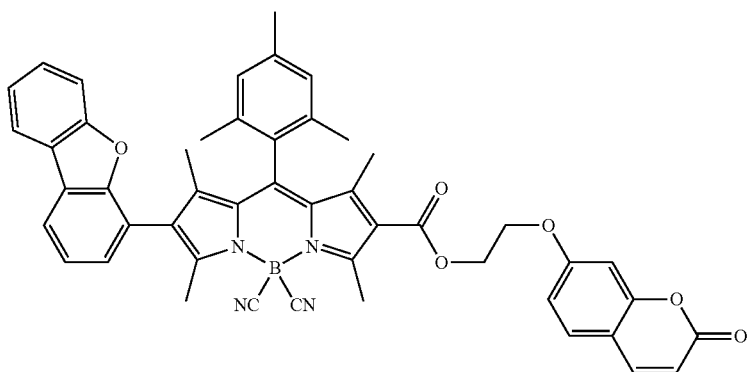

-continued
compound 1-93
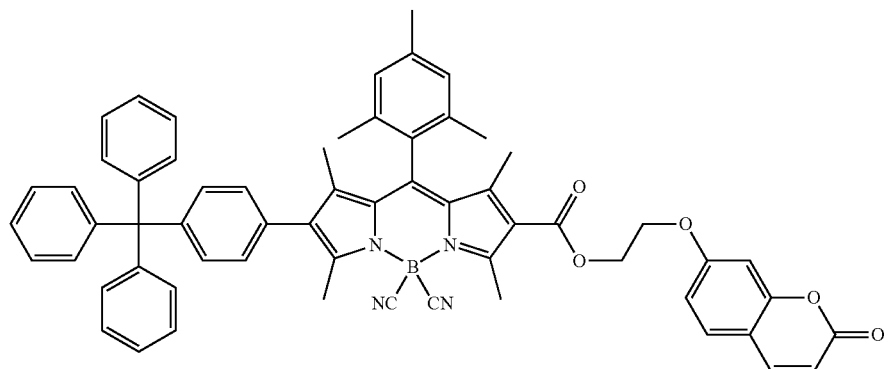
compound 1-94
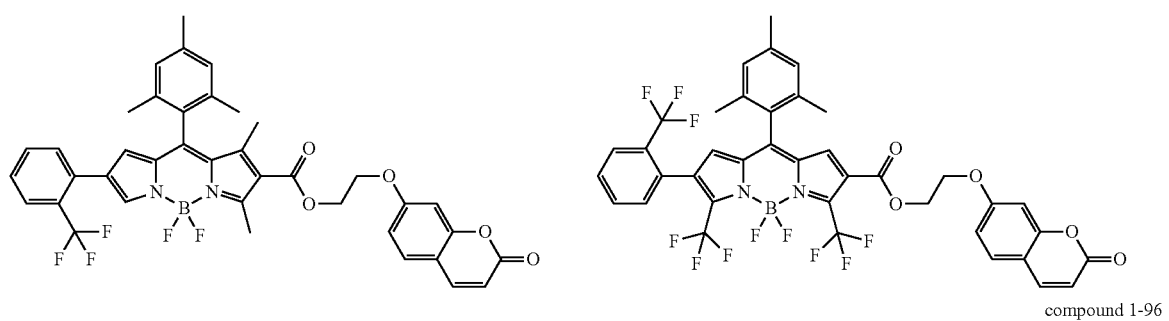
compound 1-95
compound 1-96
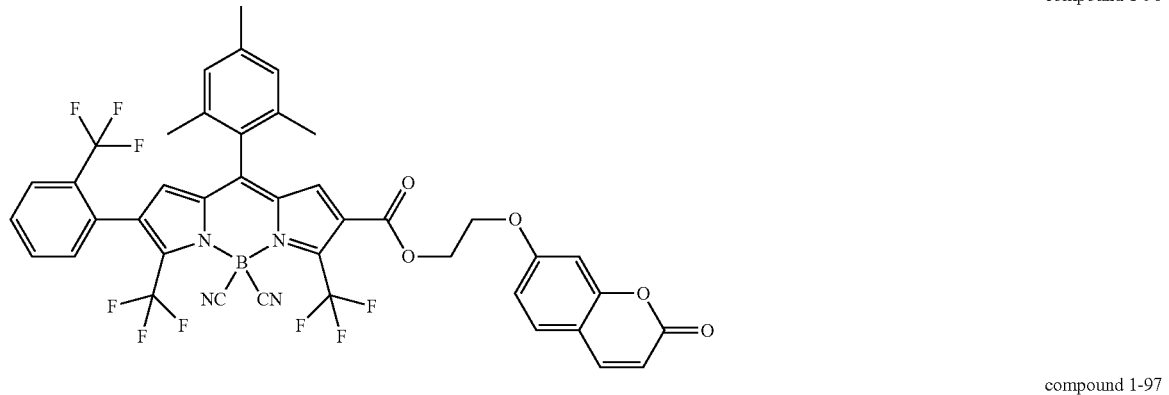
compound 1-97
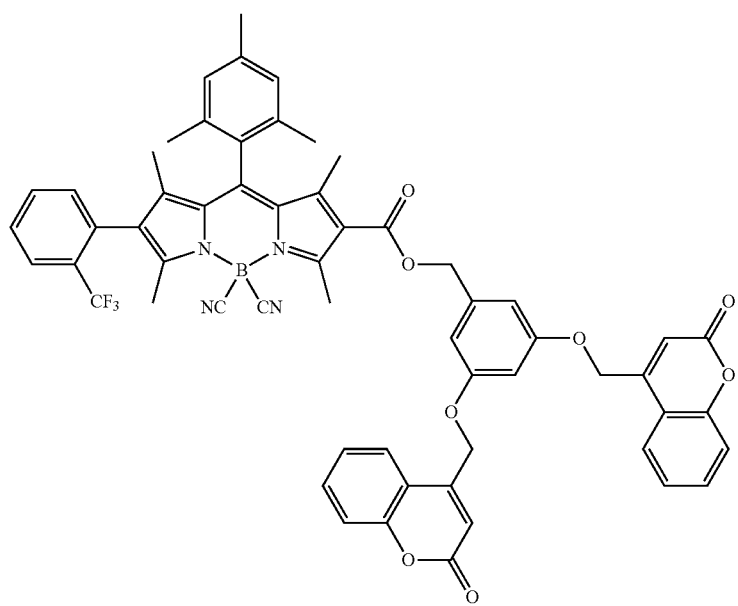

compound 1-98
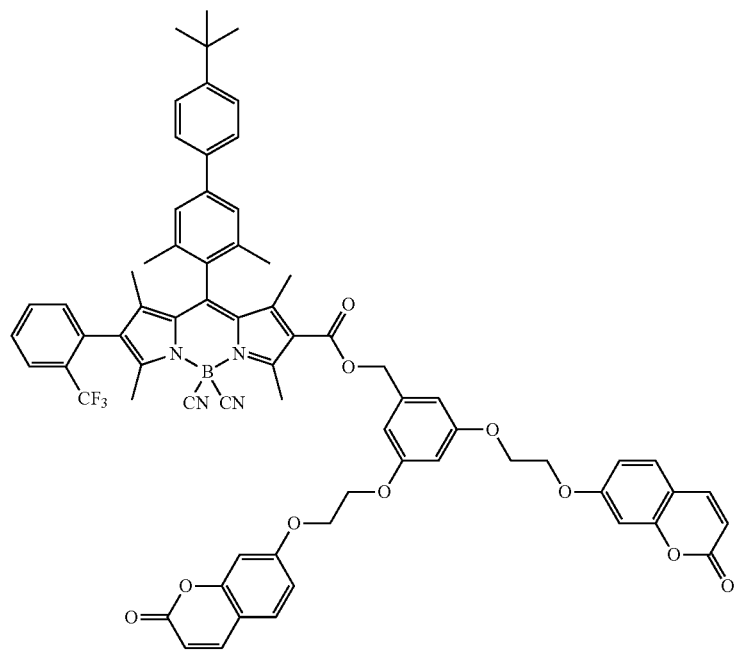
compound 1-99
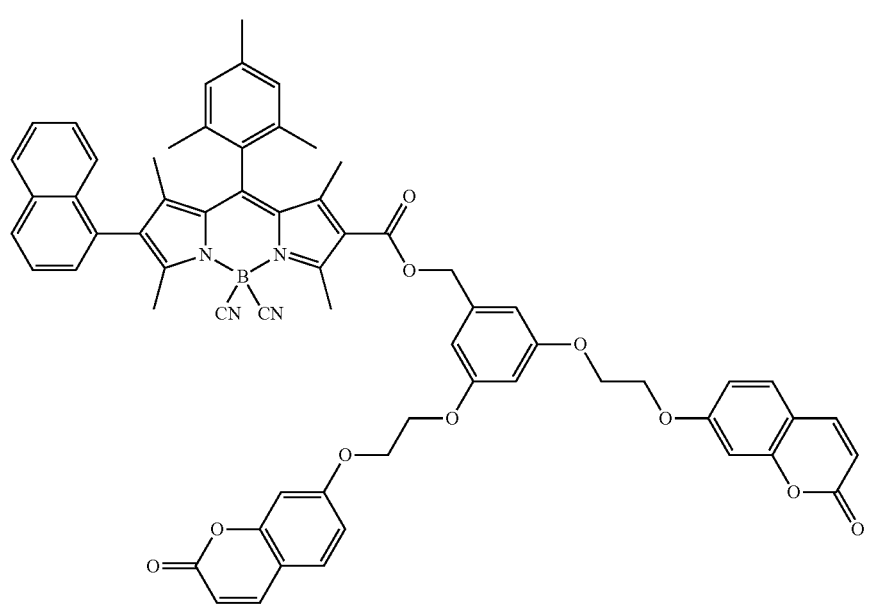

compound 1-100
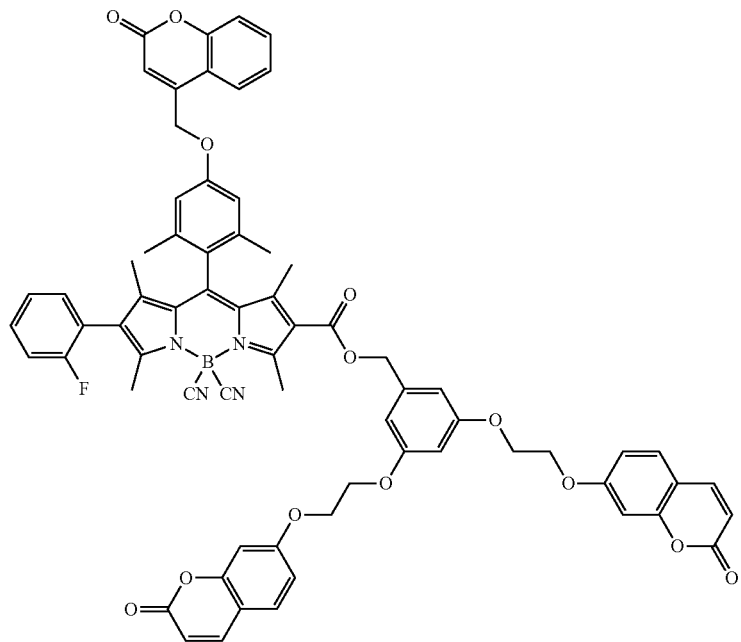
compound 1-101
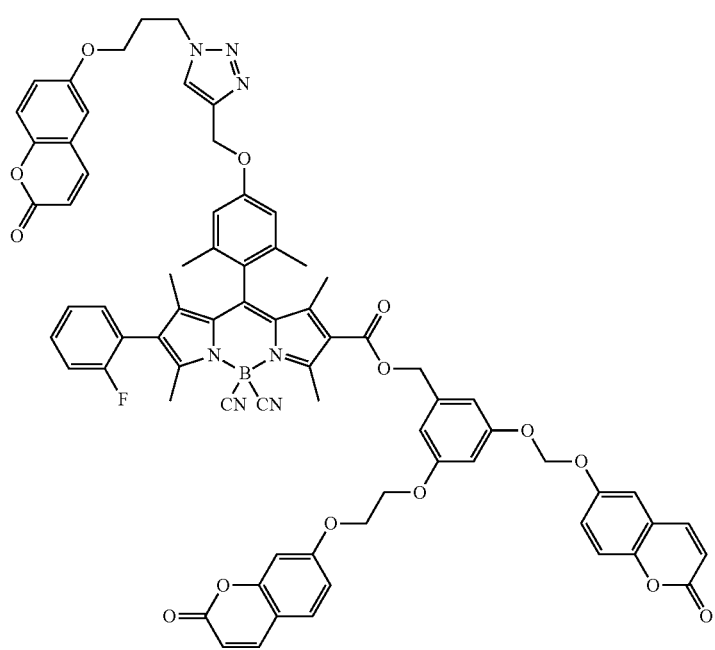

-continued
compound 1-102
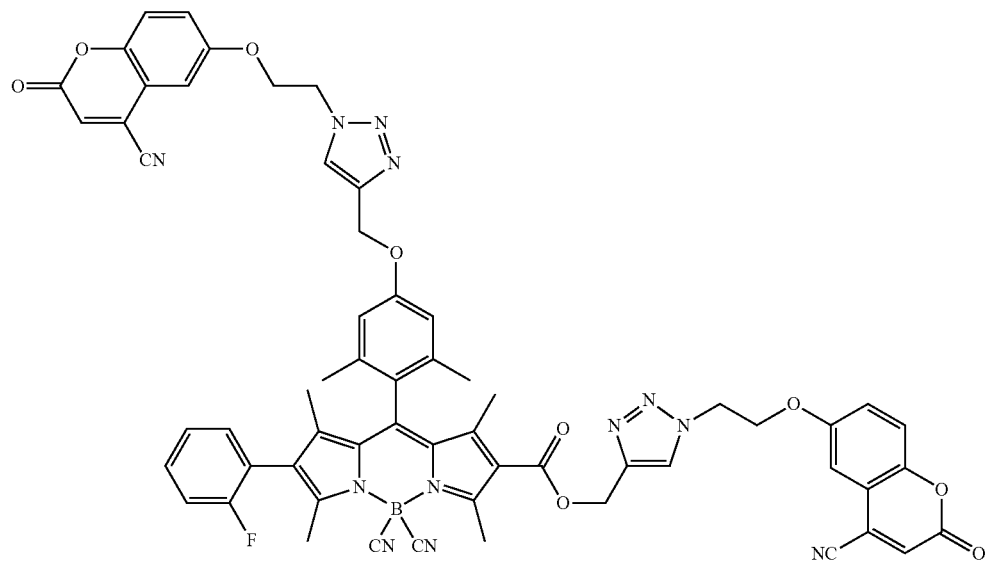
compound 1-103
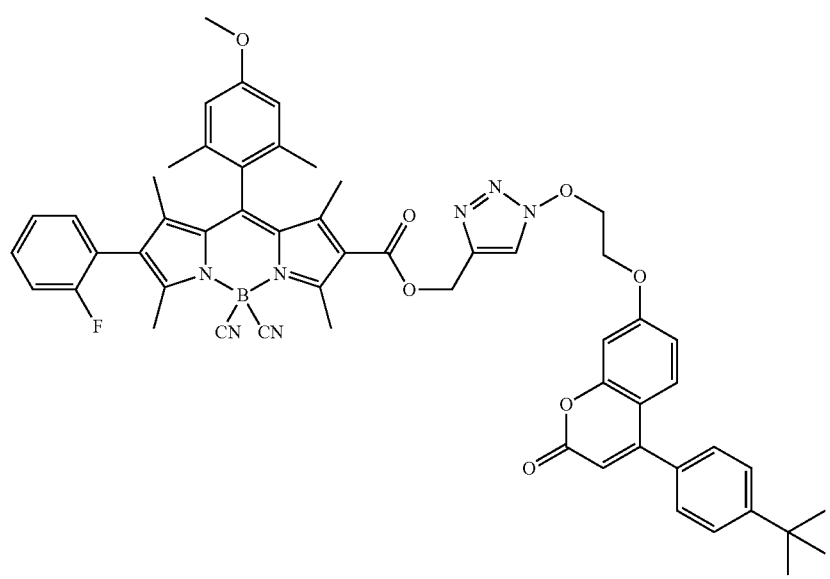
compound 1-104
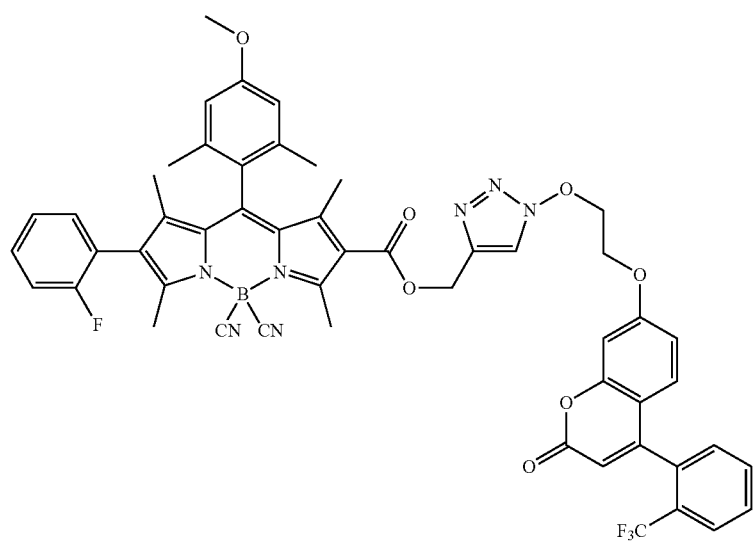

-continued
compound 1-105
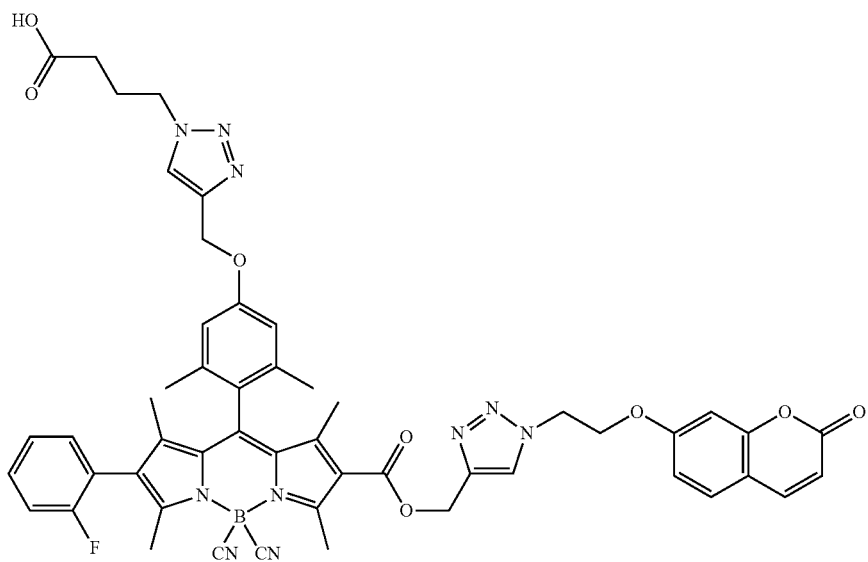
compound 1-106
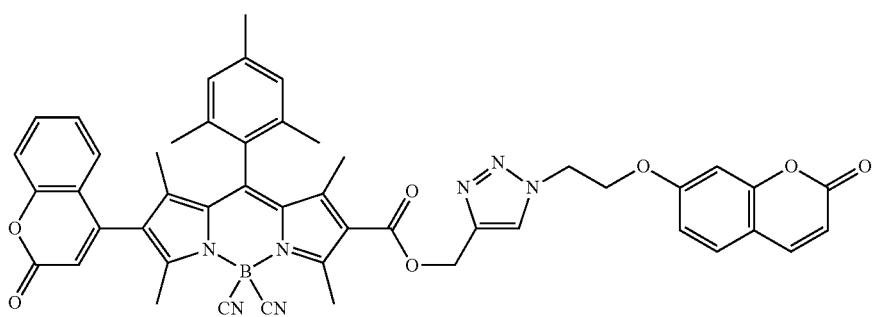
compound 1-107
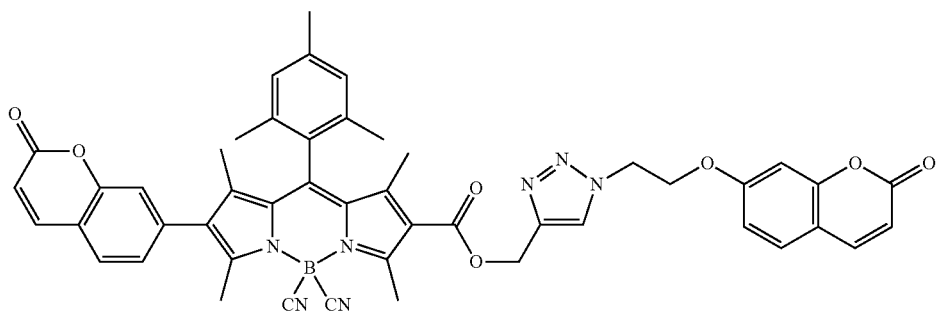
compound 1-108
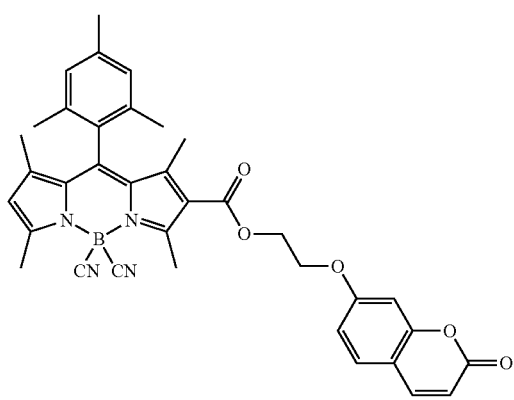
compound 1-109
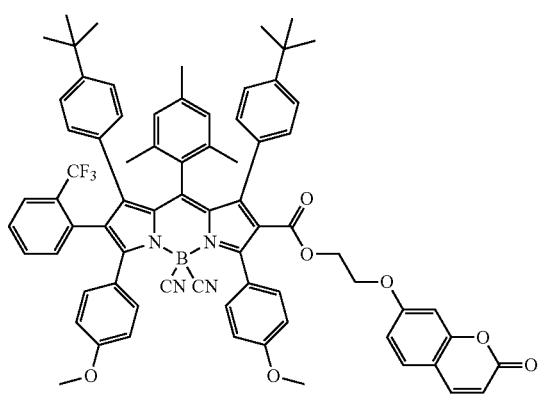

-continued
compound 1-110
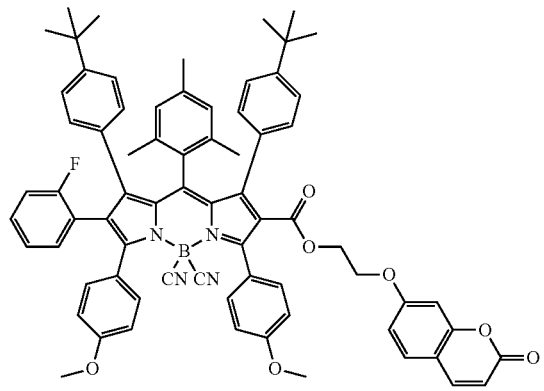
compound 1-111
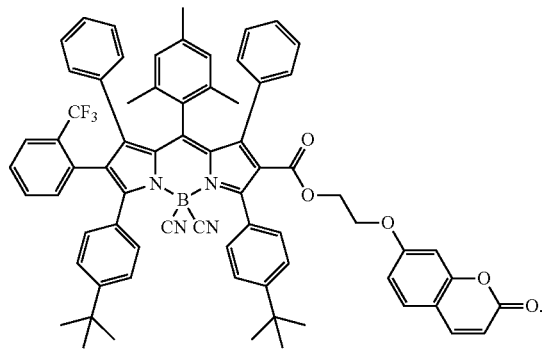
17. A color conversion film comprising:
a resin matrix; and
the compound of Chemical Formula 1 of claim 1 dispersed into the resin matrix.
18. A backlight unit comprising the color conversion film of claim 17.
19. A display apparatus comprising the backlight unit of claim 18.
* * * * *